United States Patent [19]
Shturman et al.

[11] Patent Number: 6,024,749
[45] Date of Patent: Feb. 15, 2000

[54] ROTATIONAL ATHERECTOMY DEVICE WITH IMPROVED EXCHANGEABLE DRIVE SHAFT CARTRIDGE

[75] Inventors: Leonid Shturman, Minnetonka, Minn.; Georgiy Morov, Moscow, Russian Federation

[73] Assignee: Shturman Cardiology Systems, Inc., Minneapolis, Minn.

[21] Appl. No.: 09/039,732

[22] Filed: Mar. 16, 1998

Related U.S. Application Data

[63] Continuation-in-part of application No. 08/988,493, Dec. 10, 1997, which is a continuation-in-part of application No. 08/957,942, Oct. 27, 1997.

[51] Int. Cl.⁷ .................................................. A61B 17/22
[52] U.S. Cl. .......................................... 606/159; 606/180
[58] Field of Search .............................. 606/1, 107, 159, 606/166, 167, 170, 171, 185; 604/19, 22

[56] References Cited

U.S. PATENT DOCUMENTS

| | | |
|---|---|---|
| 1,851,146 | 3/1932 | Banker . |
| 3,712,438 | 1/1973 | Roddy et al. . |
| 3,937,222 | 2/1976 | Banko . |
| 4,445,509 | 5/1984 | Auth . |
| 4,679,557 | 7/1987 | Opie et al. . |
| 4,771,774 | 9/1988 | Simpson et al. . |
| 4,857,046 | 8/1989 | Stevens et al. ............................ 604/22 |
| 4,926,986 | 5/1990 | Noel . |
| 4,990,134 | 2/1991 | Auth . |
| 5,217,474 | 6/1993 | Zacca et al. ............................ 606/159 |
| 5,312,427 | 5/1994 | Shturman ................................ 606/159 |
| 5,314,407 | 5/1994 | Auth et al. ................................ 604/22 |

(List continued on next page.)

FOREIGN PATENT DOCUMENTS

| | | |
|---|---|---|
| 0 244 058 | 11/1987 | European Pat. Off. . |
| 0 321 319 | 6/1989 | European Pat. Off. . |
| 761 398 | 9/1933 | France . |
| 1000163 | 10/1996 | Netherlands . |
| 2080454 | 5/1997 | Russian Federation . |
| 1350393 | 11/1987 | U.S.S.R. . |
| WO 94/12132 | 6/1994 | WIPO . |
| WO 96/37153 | 11/1996 | WIPO . |
| WO 97/14470 | 4/1997 | WIPO . |

OTHER PUBLICATIONS

Brochure: "Rotalink—Sizing Up is a Snap," SCIMED Boston Scientific Corporation, Maple Grove, MN 55311–1566, seven pages, Feb. 1997.

*Primary Examiner*—Glenn K. Dawson
*Attorney, Agent, or Firm*—Fredrikson & Byron, P.A.

[57] ABSTRACT

A rotational atherectomy device which includes a handle housing and an exchangeable drive shaft cartridge removably attachable to the handle housing. A rotatable prime mover is carried by a prime mover carriage disposed within the handle housing, the prime mover carriage being longitudinally movable with respect to the handle housing. The exchangeable cartridge includes a cartridge housing which is removably attachable to the handle housing, a longitudinally movable tube which is removably attachable to the prime mover carriage, and a rotatable flexible drive shaft which is removably attachable to the prime mover. The rotational atherectomy device includes a cartridge latch, which removably locks the cartridge housing to the handle housing, and a tube latch which selectively locks the longitudinally movable tube against longitudinal movement with respect to the cartridge housing. The exchangeable cartridge also includes a slide which is longitudinally movable with respect to the cartridge housing among at least three positions: a working position where the slide causes the tube latch to unlock the longitudinally movable tube, a neutral position where the slide causes the tube latch to lock the tube against longitudinal movement with respect to the cartridge housing, and a cartridge unlocked position where the slide causes the tube latch to maintain the longitudinally movable tube in its locked position and unlocks the cartridge latch, thereby permitting the cartridge housing to be removed from the handle housing.

167 Claims, 47 Drawing Sheets

U.S. PATENT DOCUMENTS

| | | | |
|---|---|---|---|
| 5,314,438 | 5/1994 | Shturman | 606/159 |
| 5,356,418 | 10/1994 | Shturman | 606/159 |
| 5,360,432 | 11/1994 | Shturman | 606/159 |
| 5,501,694 | 3/1996 | Ressemann et al. | 606/159 |
| 5,634,933 | 6/1997 | McCombs et al. | 606/180 |
| 5,681,336 | 10/1997 | Clement et al. | 606/159 |
| 5,766,192 | 6/1998 | Zacca | 606/159 |
| 5,779,722 | 7/1998 | Shturman et al. | 606/159 |
| 5,833,246 | 11/1998 | Trott . | |
| 5,836,868 | 11/1998 | Ressemann et al. | 606/159 |
| 5,849,023 | 12/1998 | Mericle | 606/180 |

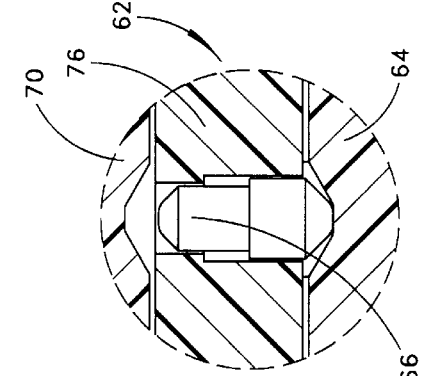
FIG. 22
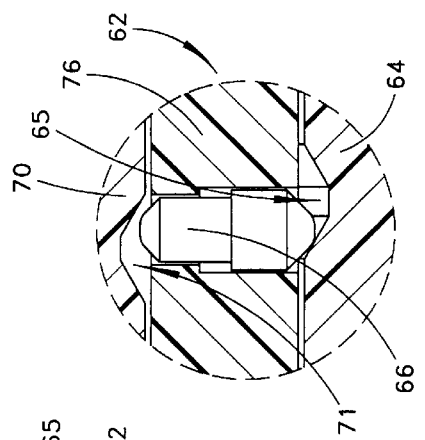
FIG. 23
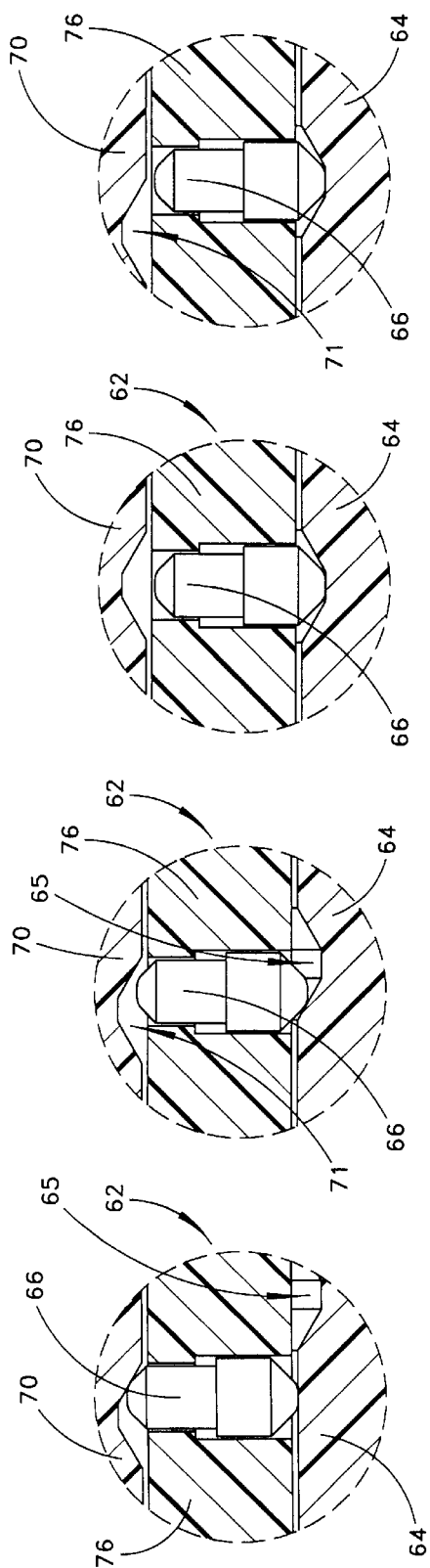
FIG. 24
FIG. 25
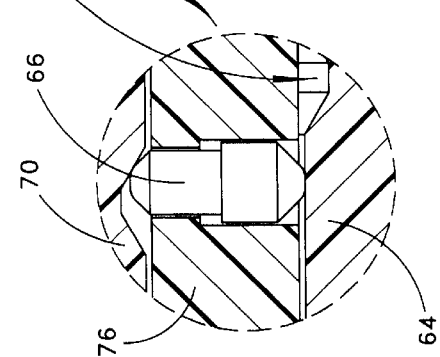
FIG. 26
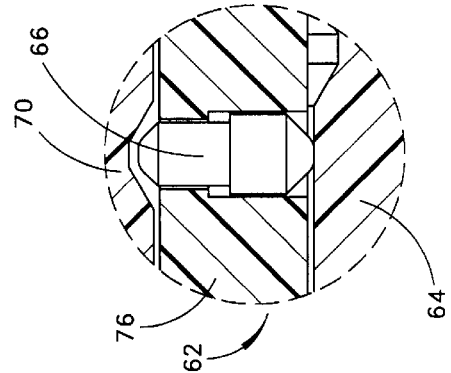
FIG. 27
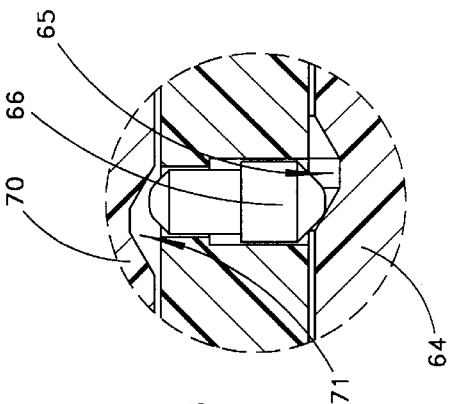
FIG. 28
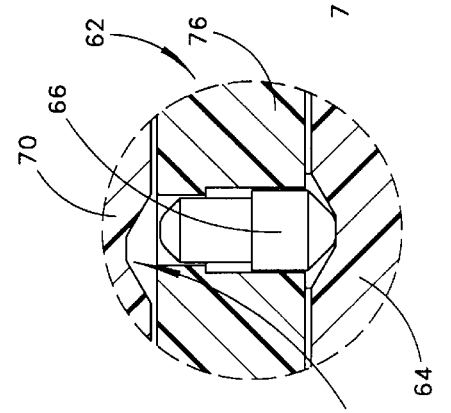
FIG. 29
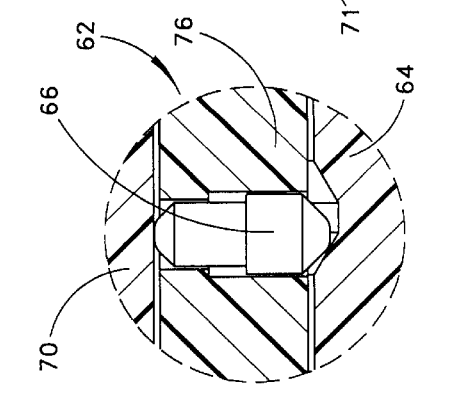

ROTATIONAL ATHERECTOMY DEVICE WITH IMPROVED EXCHANGEABLE DRIVE SHAFT CARTRIDGE

CROSS REFERENCE TO RELATED APPLICATIONS

This application is a continuation in part of application Ser. No. 08/988,493, filed Dec. 10, 1997, (the contents of which are hereby incorporated by reference) which is a continuation in part of application Ser. No. 08/957,942, filed Oct. 27, 1997 (the contents of which are also hereby incorporated by reference).

TECHNICAL FIELD

The invention relates to devices and methods for removing tissue from body passageways, such as removal of atherosclerotic plaque from arteries, utilizing a rotational atherectomy device. In particular, the invention relates to improvements in an exchangeable drive shaft cartridge of a rotational atherectomy device.

BACKGROUND OF THE INVENTION

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®. The handle of the Rotablator® device includes a variety of components, including a compressed gas driven turbine, a mechanism for clamping a guide wire extending through the drive shaft, portions of a fiber optic tachometer, and a pump for pumping saline through the drive shaft.

The connection between the drive shaft (with its associated burr) and the turbine in the Rotablator® device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameter is sometimes referred to as a "step up technique" and is recommended by the manufacturer of the Rotablator® device. In the multiple burr technique it is necessary to use a new Rotablator® device for each such successive size burr. Accordingly, there is a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design.

A subsequent version of the Rotablator® device has been introduced with the ability to exchange a flexible distal portion of the drive shaft together with a burr for another distal portion of a drive shaft having a different size burr. Technical details of such a system are contained in international patent application No. WO 96/37153. This system utilizes a flexible drive shaft having a connect/disconnect feature allowing the physician to disconnect the exchangeable distal portion of the flexible drive shaft, together with the burr, from the flexible proximal portion of the drive shaft which is connected to the turbine of the handle, thus permitting the burr size to be changed without discarding the entire atherectomy unit. Each exchangeable drive shaft portion is disposed within its own exchangeable catheter and catheter housing. The flexible proximal portion of the drive shaft in this system is permanently attached to the turbine and is not exchanged. This system has been commercialized by Boston Scientific under the trademark Rotablator® RotaLink™ System. While the Rotablator® RotaLink™ System does permit one to change the burr size, the steps required to actually disconnect the exchangeable portion of the drive shaft and replace it with another exchangeable portion of the drive shaft are quite involved and require relatively intricate manipulation of very small components.

First, a catheter housing must be disconnected from the handle and moved distally away from the handle to expose portions of both the proximal and distal sections of the flexible drive shaft which contain a disconnectable coupling. This coupling is disconnected by sliding a lock tube distally, permitting complementary lock teeth on the proximal and distal portions of the flexible drive shaft to be disengaged from each other. A similar flexible distal drive shaft portion with a different burr may then be connected to the flexible proximal portion of the drive shaft. To accomplish such assembly, the lock tooth on the proximal end of the distal replacement portion of the drive shaft must first be both longitudinally and rotationally aligned with the complementary lock tooth at the distal end of the proximal portion of the drive shaft. Since the flexible drive shaft typically is less than 1 mm in diameter, the lock teeth are similarly quite small in size, requiring not insignificant manual dexterity and visual acuity to properly align and interlock the lock teeth. Once the lock teeth have been properly interlocked with each other, the lock tube (also having a very small diameter) is slid proximally to secure the coupling. The catheter housing must then be connected to the handle housing.

While this system does permit one to exchange one size burr (together with a portion of the drive shaft) for a burr of another size, the exchange procedure is not an easy one and must be performed with considerable care. The individual performing the exchange procedure must do so while wearing surgical gloves to protect the individual from the blood of the patient and to maintain the sterility of the elements of the system. Surgical gloves diminish the tactile sensations of the individual performing the exchange procedure and therefore make such exchange procedure even more difficult.

Accordingly, it would be desirable to have an atherectomy device permitting easier attachment and/or exchange of the drive shaft and its tissue removing implement.

SUMMARY OF THE INVENTION

The invention provides a rotational atherectomy device designed to facilitate easy attachment, detachment and exchange of the drive shaft and its tissue removing implement. The rotational atherectomy device includes a handle housing and an exchangeable drive shaft cartridge which is removably attachable to the handle housing. A rotatable prime mover is carried by a prime mover carriage disposed within the handle housing, the prime mover carriage being longitudinally movable with respect to the handle housing. The exchangeable drive shaft cartridge includes a cartridge housing which is removably attachable to the handle housing, a longitudinally movable tube disposed within the cartridge housing, the tube having a proximal end portion that is removably attachable to the prime mover carriage, and a rotatable flexible drive shaft. The drive shaft has a proximal portion which is disposed within the longitudinally movable tube and a distal portion which includes a tissue removal implement. A drive shaft attachment mechanism is provided to removably attach the proximal portion of the drive shaft to the prime mover.

The rotational atherectomy device also includes a cartridge latch, which removably locks the cartridge housing to the handle housing, and a tube latch which selectively locks the longitudinally movable tube against longitudinal movement with respect to the cartridge housing. The exchangeable cartridge also includes a slide which is longitudinally movable with respect to the cartridge housing among at least three positions: a working position where the slide causes the tube latch to unlock the longitudinally movable tube, a neutral position where the slide causes the tube latch to lock the tube against longitudinal movement with respect to the cartridge housing, and a cartridge unlocked position where the slide causes the tube latch to maintain the longitudinally movable tube in its locked position and unlocks the cartridge latch, thereby permitting the cartridge housing to be removed from the handle housing.

In a preferred embodiment of the invention the cartridge latch includes a radially resilient element which carries a catch, the catch restricting free movement of the slide between its neutral position and its working position.

In a particularly preferred embodiment of the invention, the exchangeable drive shaft cartridge also includes a spring which biases the slide towards its working position. In this embodiment the catch of the radially resilient element of the cartridge latch and the catch engaging structure of the slide are sized and positioned with respect to each other so that insertion of the cartridge housing into the handle housing releases the slide from the catch, thereby allowing the spring to move the slide from its neutral position to its working position.

BRIEF DESCRIPTION OF THE DRAWINGS

FIGS. 22–29 are enlarged views of a portion of FIG. 21, illustrating the tube latch in its various positions during attachment, use, and detachment of the exchangeable drive shaft cartridge;

DETAILED DESCRIPTION OF THE INVENTION

Figure 1:
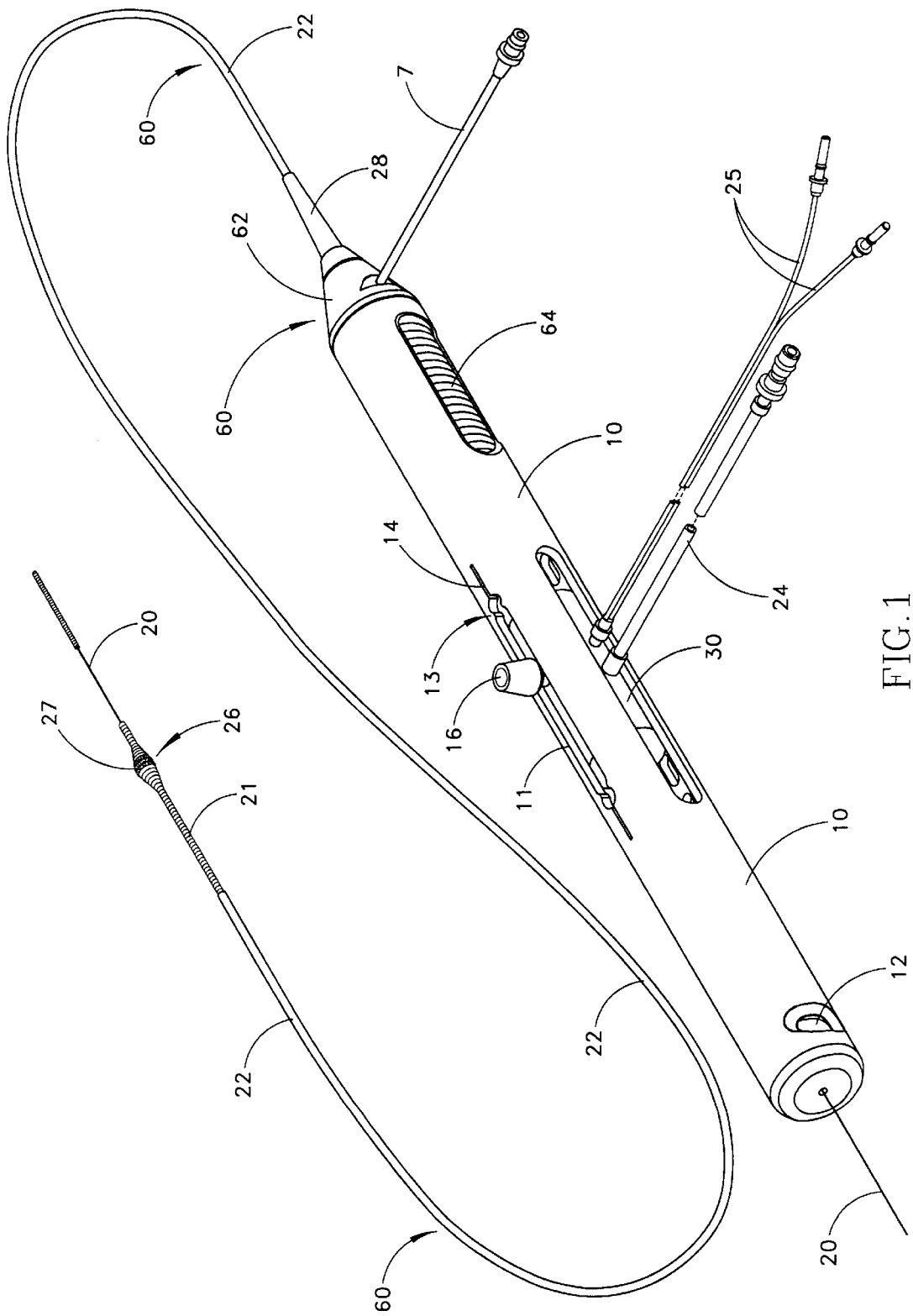
FIG. 1 is a perspective view of a rotational atherectomy device of the invention.

FIG. 1 illustrates one embodiment of a rotational atherectomy device of the invention. The device desirably includes a tubular handle housing 10. The handle housing 10 has a proximal portion which carries a guide wire clamp mechanism 12, an intermediate portion which carries a prime mover carriage 30, and a distal portion which is adapted to releasably interlock with an exchangeable drive shaft cartridge 60. Details of a preferred guide wire clamp mechanism used to clamp the guide wire 20 are contained in copending U.S. patent application Ser. No. 08/792,101, filed Jan. 31, 1997, the contents of which are hereby incorporated by reference.

The prime mover carriage 30 can be moved longitudinally within the handle housing 10 through a limited range of motion. A control knob 16 (operatively secured to the prime mover carriage 30) is provided to facilitate advancing and retracting the prime mover carriage 30 with respect to the handle housing 10.

The prime mover carriage 30 carries a prime mover. Preferably the prime mover is a compressed gas driven turbine. The turbine may be powered by, e.g., compressed nitrogen or compressed air. For this purpose a compressed gas supply line 24 may be provided, the supply line 24 being connected to the prime mover carriage 30. A pair of fiber optic cables 25 may also be provided for monitoring the speed of rotation of the turbine (e.g., as described in the Auth '407 patent and implemented in the Rotablator® device).

The exchangeable drive shaft cartridge 60 includes a cartridge housing 62, an elongated catheter 22 extending distally from the cartridge housing 62, a rotatable flexible drive shaft 21 disposed within the catheter 22, a longitudinally movable slide 64, and a longitudinally movable tube 70 carried within the cartridge housing 62. The longitudinally movable tube 70 is not seen in FIG. 1, but is discussed below in connection with, e.g., FIGS. 2–4. The elongated catheter 22 is carried by the cartridge housing 62 and has a proximal end portion which is disposed within a short rigid tube 23. The rigid tube 23 is secured within a generally tubular end piece 88 of the cartridge housing 62. Preferably a strain relief element 28 is disposed around the distal portion of the rigid tube 23 and the proximal portion of the catheter 22. The strain relief element 28 also is secured to the cartridge housing 62.

The exchangeable drive shaft cartridge 60 includes a flexible fluid supply tube 7. One end of the fluid supply tube 7 communicates with an external fluid supply (not shown) while the other end of the tube 7 is attached to a rigid fitting 61 of the cartridge housing 62. The flexible fluid supply tube 7 is in fluid communication with the inner lumen of the catheter 22 (see, e.g., FIG. 4), supplying fluid to help reduce friction between the rotating drive shaft 21 and non-rotating elements disposed within (i.e., the guide wire 20) and around the drive shaft 21.

The flexible drive shaft 21 is rotatable over a guide wire 20 and includes a proximal portion, an intermediate portion, and a distal portion. The proximal portion of the drive shaft 21 is removably attachable to the prime mover. This portion of the drive shaft is not visible in FIG. 1. The intermediate portion of the drive shaft 21 is disposed primarily within the catheter 22 and therefore also is not visible in FIG. 1. The distal portion of the drive shaft 21 extends distally from the catheter 22 and includes a tissue removal implement 26. The tissue removal implement 26 in the illustrated embodiment comprises an eccentric enlarged diameter section of the drive shaft 21. A portion of the eccentric enlarged diameter section is covered with an abrasive material to define an abrasive segment 27 of the drive shaft 21. The eccentric tissue removal implement of such design is described, e.g., in U.S. patent application Ser. No. 08/911,586, filed Aug. 14, 1997, the contents of which are hereby incorporated by reference. It should be understood that any suitable tissue removal implement may be used, including the tissue removal implement described in U.S. patent application Ser. No. 08/679,470, filed Jul. 15, 1996, or the diamond-coated burr proposed by Auth in U.S. Pat. No. 4,990,134.

Figure 2:
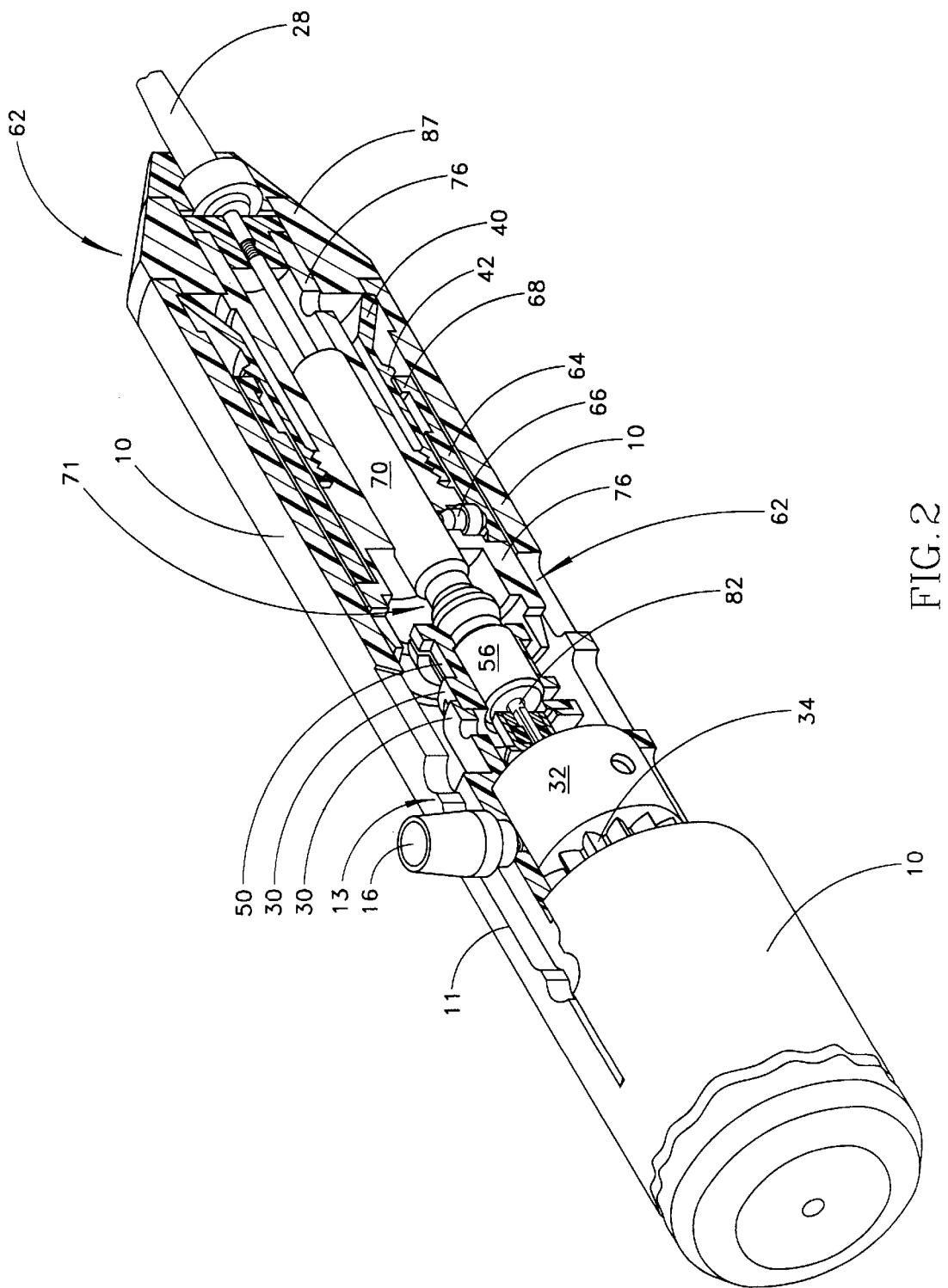
FIG. 2 is an enlarged perspective, partially broken-away view of a portion of the device shown in FIG. 1, illustrating the exchangeable drive shaft cartridge connected to the handle housing.

By comparing FIG. 1 with FIG. 2 one can see that the structure in FIG. 2 is not quite to scale with respect to FIG. 1. For example, the slot 11 is considerably shortened in FIG. 2 with respect to FIG. 1. In many other drawings (particularly longitudinal cross-sections) the diameter of the device and its components, as well as wall thicknesses, have been exaggerated so that the structural details of the device can be more clearly depicted and understood. The atherectomy device depicted in FIG. 1 is generally to scale, except for the length of the catheter 22 and drive shaft 21, which are actually substantially longer. Deviations from scale in the drawings should be readily apparent to one of ordinary skill in the art.

Figure 3:
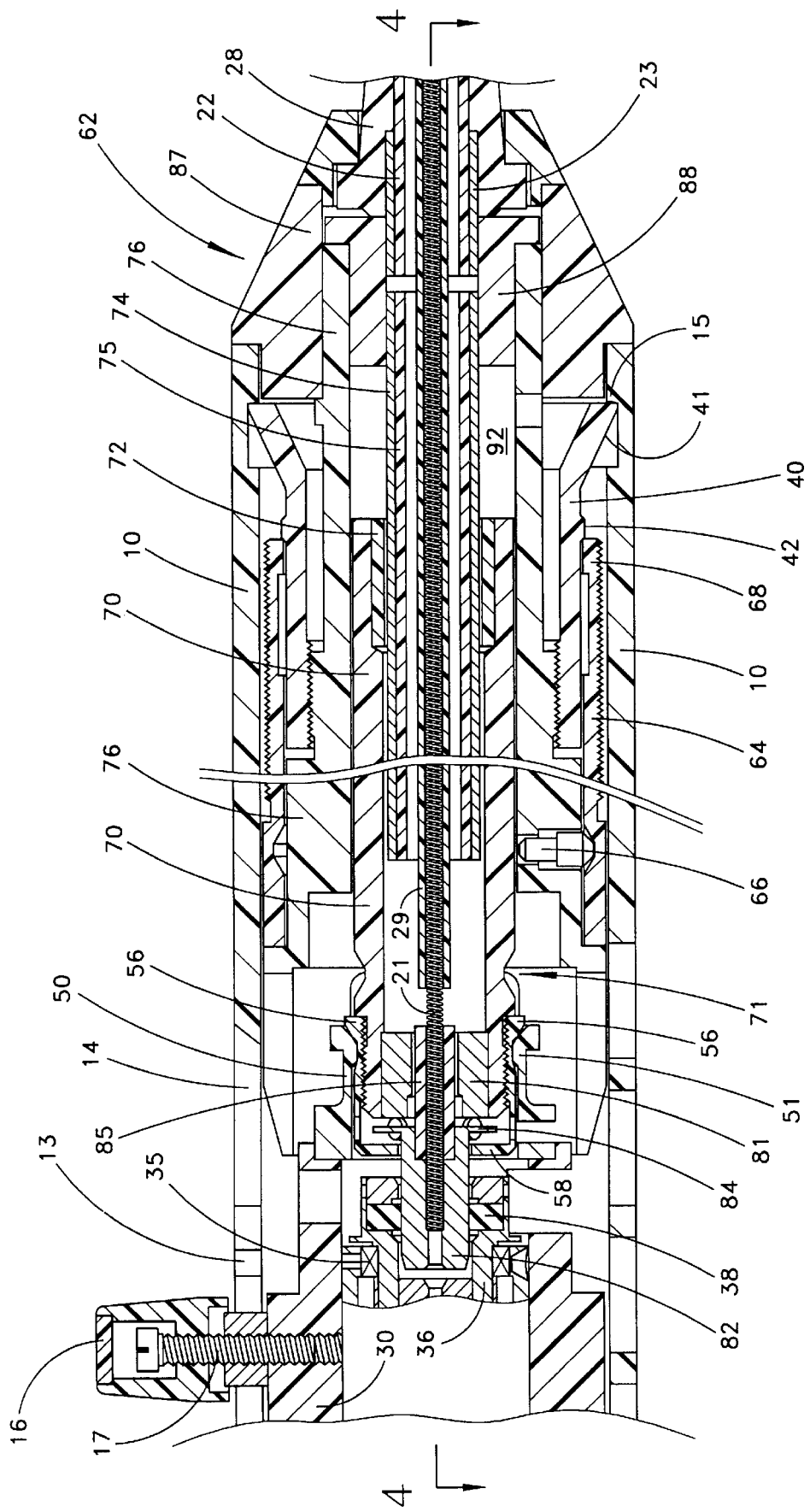
FIG. 3 is a broken away, longitudinal cross-section of the atherectomy device shown in FIG. 2.
Figure 4:
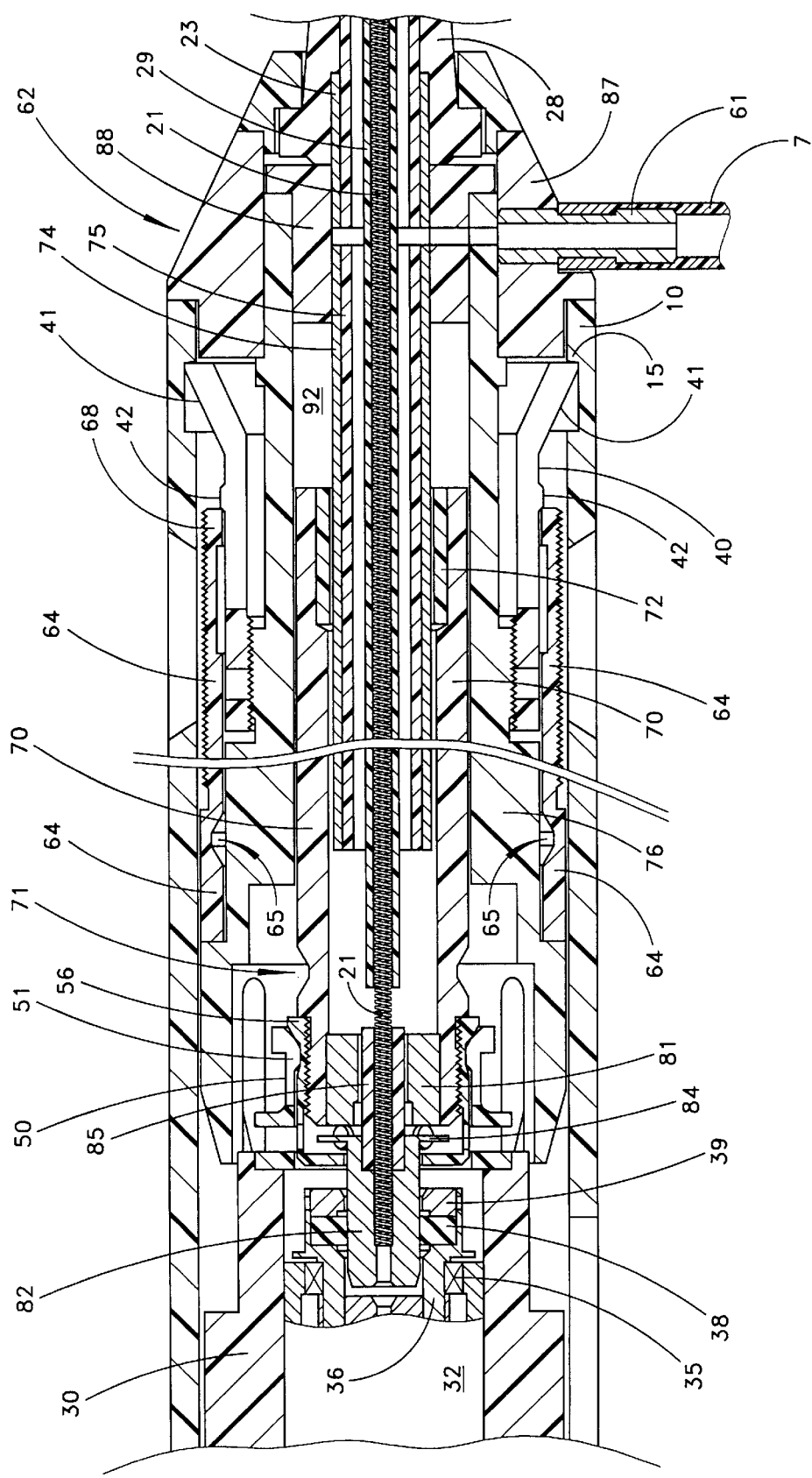
FIG. 4 is a longitudinal cross-sectional view of FIG. 3, taken along lines 4—4 thereof, and illustrating a flexible fluid supply tube attached to the exchangeable drive shaft cartridge.

FIGS. 2–4 illustrate further details regarding the components of the exchangeable drive shaft cartridge 60 and how they are removably attached to the handle housing, the prime mover carriage and the prime mover. A rotatable prime mover (such as a compressed gas driven turbine or similar supply of rotational motion) is removably attachable (as will be described below) to the flexible drive shaft 21. The prime mover can be any device which can rotate the flexible drive shaft 21 at a sufficiently high speed. In the preferred embodiment illustrated in the drawings the prime mover is carried by a prime mover carriage 30 which is disposed within the handle housing 10. The prime mover carriage 30 can be moved longitudinally within the handle housing 10 through a limited range of motion. A control knob 16, secured to the prime mover carriage 30 by a shaft 17, is provided to facilitate advancement and retraction of the prime mover carriage 30 with respect to the handle housing 10. The shaft 17 extends out of the handle housing 10 through a slot 11 in the handle housing 10, the length of the slot 11 defining the limits of the range of motion of the prime mover carriage 30. The distal end portion of the slot 11 includes a narrowed segment 13 which divides the range of motion of the control knob 16 and the prime mover carriage 30 into a range of working positions (located proximally of the narrowed segment 13) and a cartridge exchange position (located distally of the narrowed segment 13). The narrowed segment 13 of the slot 11 provides a positive tactile feeling and an audible click when the control knob 16 and its shaft 17 pass through the narrowed segment 13 and either enter the cartridge exchange position or return back to the range of working positions. A relief slot 14 is provided distally of the distal end of the slot 11.

In the embodiment shown in the drawings, a compressed gas driven turbine is utilized. The turbine can be constructed in a variety of suitable ways. In the embodiment depicted in the drawings, the turbine includes a turbine wheel 34 carried on a hollow turbine shaft 36 which passes through a turbine housing 32. The hollow turbine shaft 36 is supported by a pair of conventional bearings 35, only one of which is shown in the drawings.

A drive shaft attachment mechanism is provided to removably attach the drive shaft 21 to the prime mover. The drive shaft attachment mechanism comprises a prime mover socket 38 carried by the prime mover, and an elongated shank 82 carried by the proximal end portion of the drive shaft 21. The drive shaft shank 82 is removably insertable into the prime mover socket 38. Preferably at least one of the drive shaft shank 82 and the prime mover socket 38 is radially resilient. In the preferred embodiment shown in the drawings, the prime mover socket 38 is resilient. The prime mover socket 38 may be made to be radially resilient in a variety of ways. In the drawings the prime mover socket 38 consists of a resilient collar secured inside a recess in the hollow turbine shaft 36 by a cap 39. A variety of other suitable ways may also be utilized to secure a prime mover socket 38 to the turbine shaft 36.

The inner diameter of the prime mover socket 38 is selected to provide a sufficiently tight interference fit with the drive shaft shank 82 so that, when the drive shaft 21 is attached to the prime mover, the shank 82 and the drive shaft 21 will both rotate and move longitudinally together with the prime mover socket 38 and the prime mover when the prime mover is rotated or moved longitudinally with respect to the handle housing 10.

The elongated shank 82 is secured, either directly or indirectly, to the proximal end portion of the flexible drive shaft 21. Suitable adhesives or other conventional attachment methods may be utilized to attach the shank 82 to the flexible drive shaft 21. Moreover, the proximal end portion of the drive shaft 21 can itself constitute the shank if it is constructed in such a fashion as to be removably insertable into the prime mover socket 38.

The elongated shank 82 preferably includes proximal and distal portions. A substantial length of the proximal portion is removably insertable into the prime mover socket 38, while the distal portion preferably includes a radially outwardly extending flange 84. As is shown in FIGS. 3–4, the flange 84 is positioned between (and spaced away from) proximal and distal abutment surfaces associated with the proximal end portion of the longitudinally movable tube 70. The flange 84 abuts the distal abutment surface associated with the longitudinally movable tube 70 when the shank 82 is inserted into the prime mover socket 38. The flange 84 abuts the proximal abutment surface associated with the longitudinally movable tube 70 when the shank 82 is pulled out of the prime mover socket 38. The distal abutment surface associated with the tube 70 in this embodiment is formed by bushing 81 and/or the tube 70 itself. The proximal abutment surface associated with the tube 70 is formed by a flange 58 of the collar 56 carried by (and forming a distal end of) the longitudinally movable tube 70.

The longitudinal lumen of the elongated shank 82 has a slightly larger diameter near its distal end so that a short section of low friction tubing 85 may be received within the lumen of the shank 82 together with the proximal portion of the drive shaft 21. Such low friction tubing 85 may be heat shrunk onto a proximal portion of the drive shaft 21 in order to reduce friction between the drive shaft 21 and the elements of the bushing 81 which forms the distal abutment surface associated with the longitudinally movable tube 70.

The longitudinally movable tube 70 is carried within the tubular core 76 of the cartridge housing 62 and has a proximal end portion which is removably attachable to the prime mover carriage 30 for longitudinal movement therewith. The longitudinally movable tube 70 surrounds a length of the flexible drive shaft 21 and facilitates longitudinal movement of the drive shaft 21 (together with the prime mover) with respect to the handle housing 10, the cartridge housing 62 and the catheter 22.

An additional stationary tube 74 is also provided. The distal end portion of the stationary tube 74 is secured within the generally tubular end piece 88 of the cartridge housing 62. A length of the proximal portion of the drive shaft 21 is disposed within the stationary tube 74. Desirably a thin-walled low friction tube 29 is heat shrunk onto a proximal portion of the drive shaft 21 to reduce friction between the drive shaft 21 and surrounding components (e.g., the longitudinally movable tube 70, the stationary tube 74, and the proximal portion of the catheter 22). Preferably the inner surface of the stationary tube 74 is provided with a thin low friction lining 75 (the thickness of this lining 75 is exaggerated in the drawings—preferably it is substantially thinner than the wall of the catheter 22).

The longitudinally movable tube 70 is slidably received in an elongated annular space 92 defined between the stationary tube 74 and the tubular core 76 of the cartridge housing 62. The movable tube 70 is longitudinally moveable within that annular space 92 with respect to both the cartridge housing 62 and the stationary tube 74. Desirably at least a portion of the inner surface of the longitudinally movable tube 70 is provided with a low-friction lining 72. The lining 72 helps minimize friction between the movable tube 70 and the stationary tube 74 as the longitudinally movable tube 70 is moved proximally and distally. The lining 72 may be made from any suitable material, such as polytetrafluoroethylene tubing. If so desired, the lining may be omitted and the movable tube 70 itself may be made of a low friction material.

The atherectomy device also includes a tube attachment mechanism positioned to removably attach the longitudinally movable tube 70 to the prime mover carriage 30. Preferably the tube attachment mechanism includes a resilient positioning mechanism for moving the prime mover carriage 30 and the shank 82 proximally with respect to the longitudinally movable tube 70 after the longitudinally movable tube 70 has been attached to the prime mover carriage 30 and after the prime mover carriage 30 has been moved to its range of working positions (i.e., the control knob 16 and its shaft 17 have been moved proximally through the narrowed segment 13). The resilient positioning mechanism spaces the flange 84 of the shank 82 away from both distal and proximal abutment surfaces associated with the longitudinally movable tube 70 to permit free rotation of the shank 82 with respect to the longitudinally movable tube 70.

In the preferred embodiment illustrated in FIGS. 2–4, the resilient positioning mechanism is comprised of at least one resilient positioning member and two sets of camming surfaces: one set associated with the resilient positioning member and another set associated with the longitudinally movable tube 70.

In the preferred embodiment shown FIGS. 2–4, the resilient positioning member is comprised of six distally extending radially resilient fingers 50 carried by the prime mover carriage 30. Each resilient finger 50 carries a radially inwardly extending detent 51 which defines the distal and proximal camming surfaces associated with the prime mover carriage 30. Preferably each of the distal camming surfaces is beveled distally outwardly, and each of the proximal camming surfaces is beveled proximally outwardly.

As illustrated in FIGS. 2–4, the longitudinally movable tube 70 has a radially inwardly extending groove 57 (better seen in FIGS. 8–11) formed in the collar 56(which forms the proximal end of the longitudinally movable tube 70). The distal portion of the surface of the groove 57 defines the distal camming surface associated with the longitudinally movable tube. The proximal camming surface associated with the longitudinally movable tube 70 is defined by the proximal portion of the annular groove 57. Preferably the tube's distal camming surface is beveled distally outwardly, and the tube's proximal camming surface is beveled proximally outwardly. The camming surfaces of the resilient fingers 50 and the camming surfaces of the longitudinally movable tube 70 are constructed so that they are stable with respect to one another (i.e., they do not slide longitudinally with respect to one another) when the prime mover carriage 30 of the assembled atherectomy device is moved back and forth with respect to the handle housing along the range of working positions.

Figure 9:
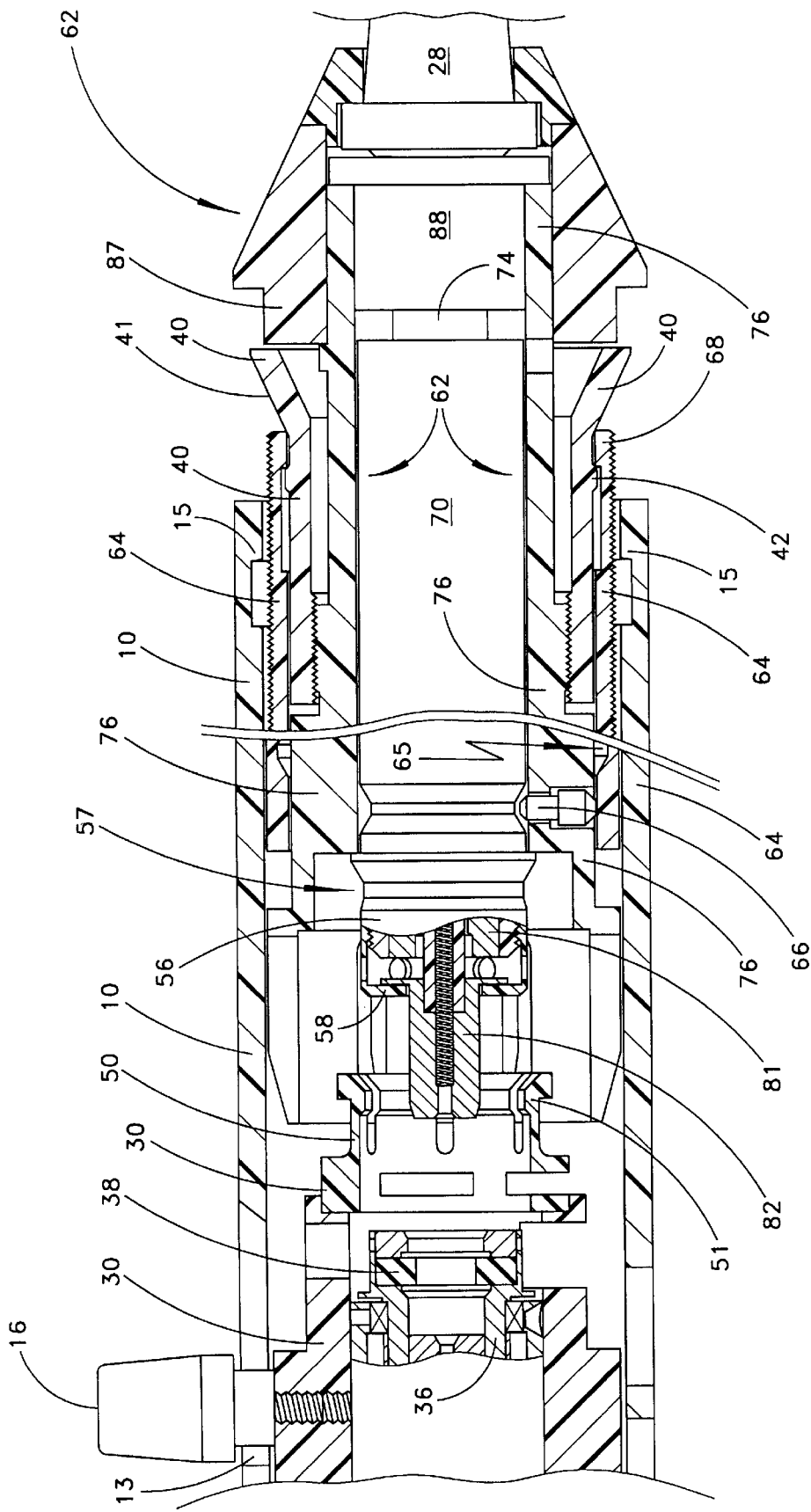
Figure 10:
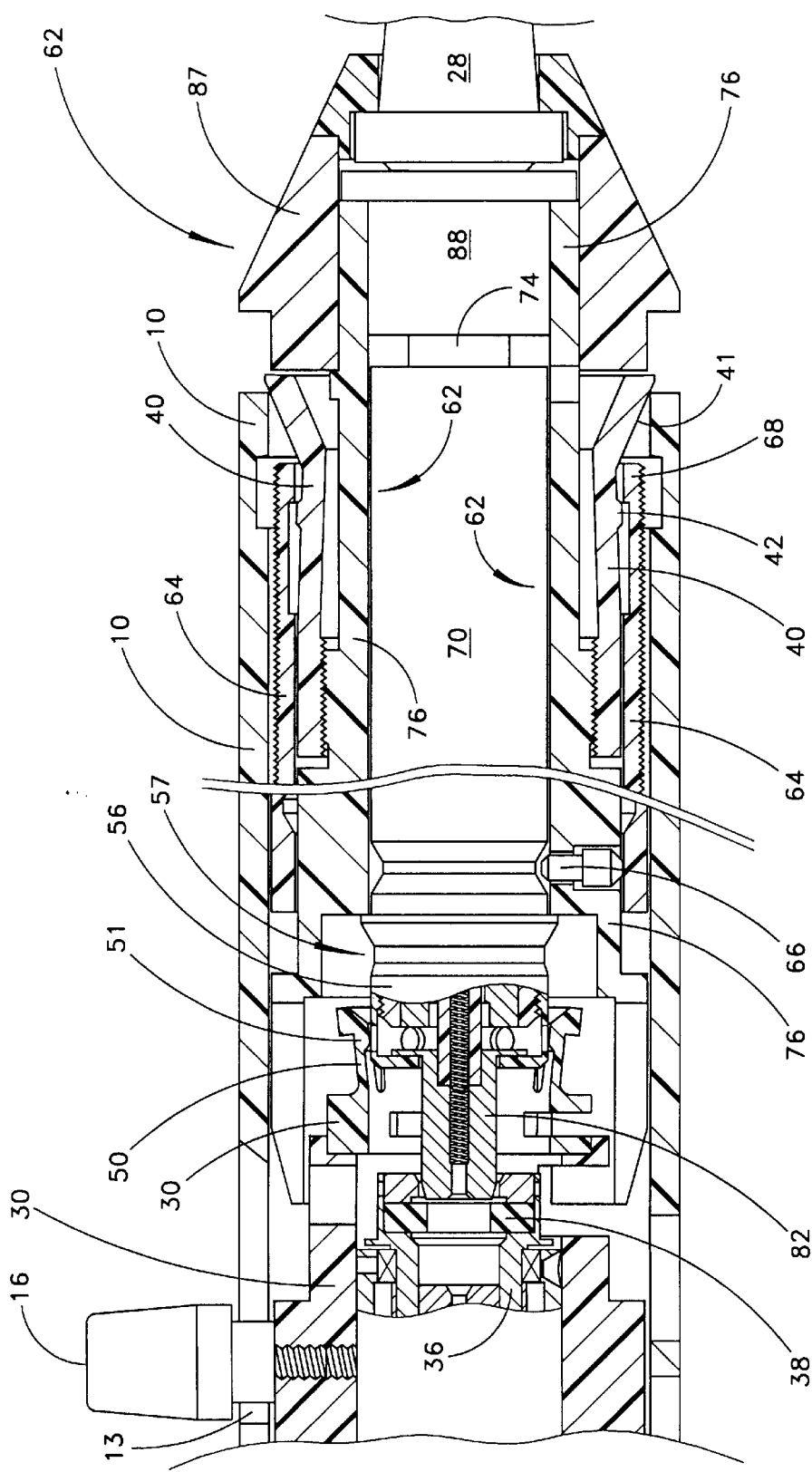
Figure 11:
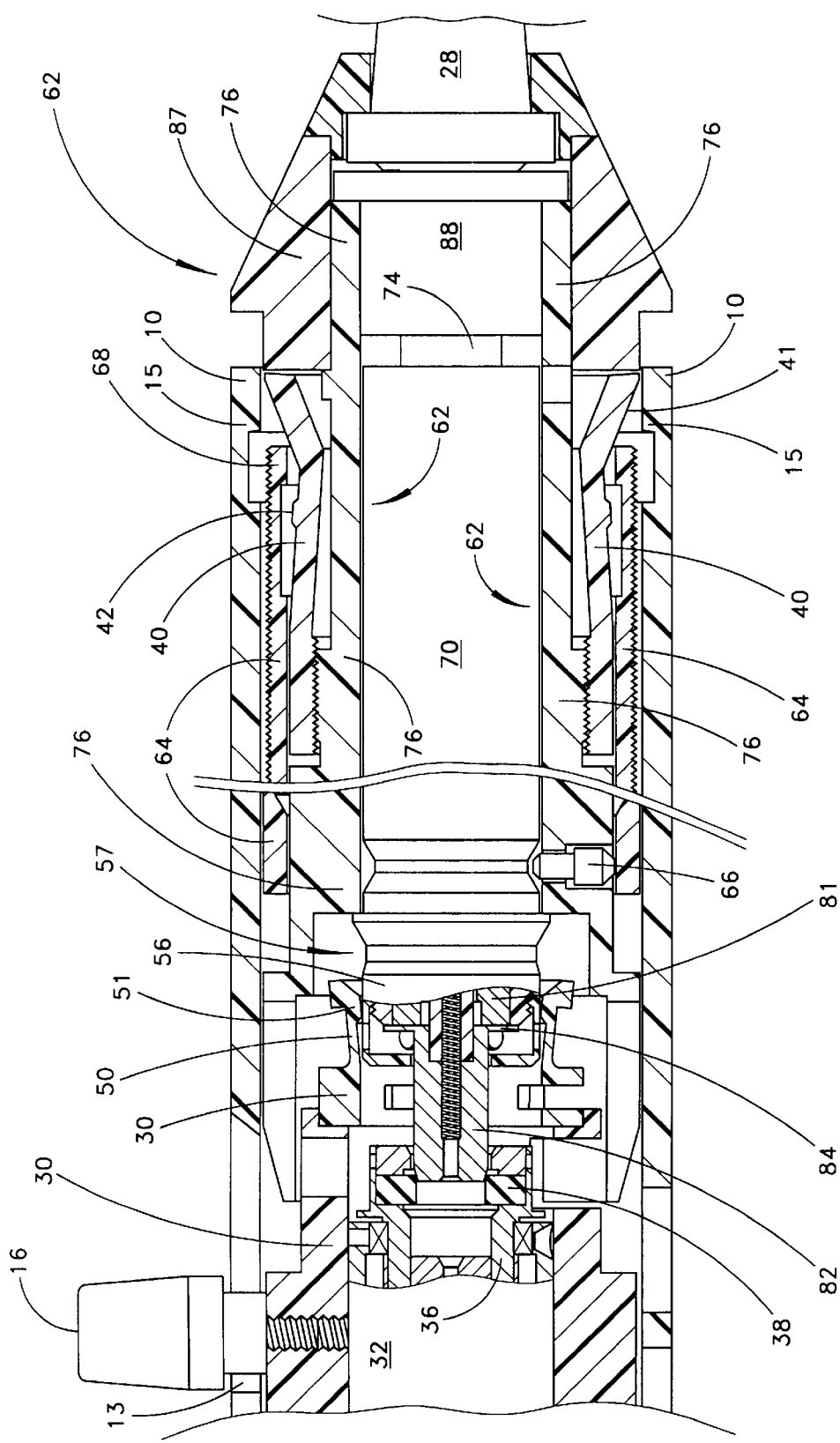
Figure 12:
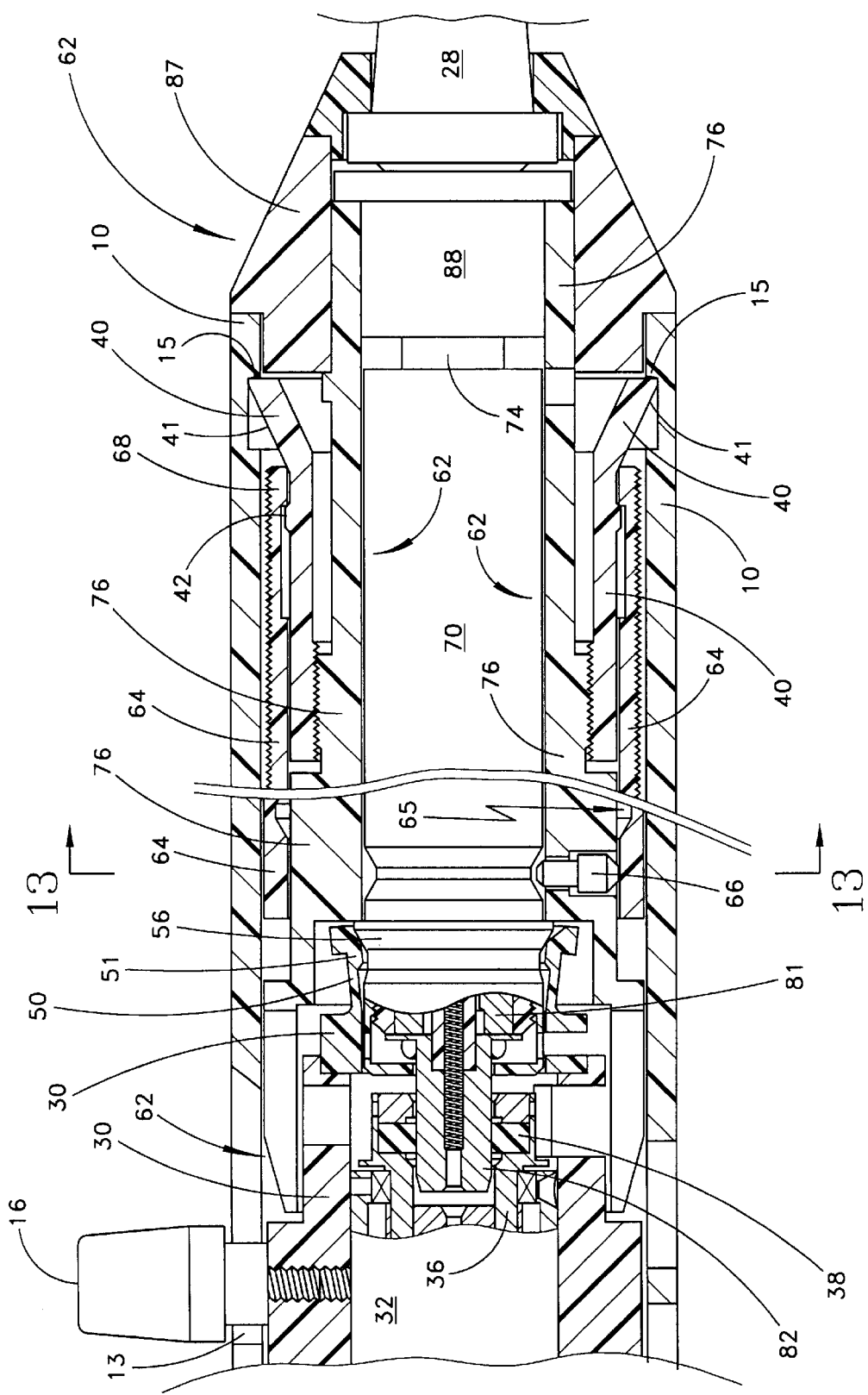

The radially resilient fingers 50 of the prime mover carriage 30 are sized and positioned to removably attach the longitudinally movable tube 70 to the prime mover carriage 30. As will be described in more detail below, during this attachment process typically the entire drive shaft cartridge 60, including the longitudinally movable tube 70, is moved proximally toward the prime mover carriage 30 as the cartridge housing 62 is inserted into the handle housing 10. When, as shown in FIGS. 9–11, the cartridge housing 62 is inserted into the handle housing 10, the collar 56 (which forms the proximal end of the longitudinally movable tube 70) engages the radially resilient fingers 50, causing the fingers 50 and their detents 51 to deflect radially outwardly. As is shown in FIG. 12, further proximal movement of the cartridge housing 62 permits the detents 51 to engage the annular groove 57, thereby removably attaching the longitudinally movable tube 70 to the prime mover carriage 30. When pressure urging the longitudinally moveable tube 70 and the prime mover carriage 30 toward each other is released (typically when the prime mover carriage 30 is moved proximally to its range of working positions), the radially resilient fingers 50 regain their non-deflected configuration, causing their distal camming surfaces to slide back to their stable position with respect to the distal camming surface associated with the longitudinally movable tube 70 (i.e., collar 56), thereby moving the prime mover carriage 30 and the drive shaft shank 82 proximally with respect to the longitudinally movable tube 70. In this position, illustrated in FIG. 3, the flange 84 of the shank 82 is spaced away from both the distal and proximal abutment surfaces associated with the longitudinally movable tube 70 to permit free rotation of the shank 82 with respect to the longitudinally movable tube 70.

During detachment of the exchangeable drive shaft cartridge 60 from the handle housing 10, relative movement of the prime mover carriage 30 away from the longitudinally movable tube 70 (see FIGS. 47–49) will cause the proximal camming surfaces of the radially resilient fingers 50 and the collar 56 to slide and move longitudinally with respect to each other, disengaging them from each other and permitting the prime mover carriage 30 to be detached from the longitudinally movable tube 70.

FIGS. 5–20 illustrate the process of attaching the exchangeable drive shaft cartridge 60 to the handle housing 10. Two key structures of the atherectomy device of the invention—the cartridge latch and the tube latch—will be described in detail in the course of reviewing the attachment process shown in these drawings.

Figure 5:
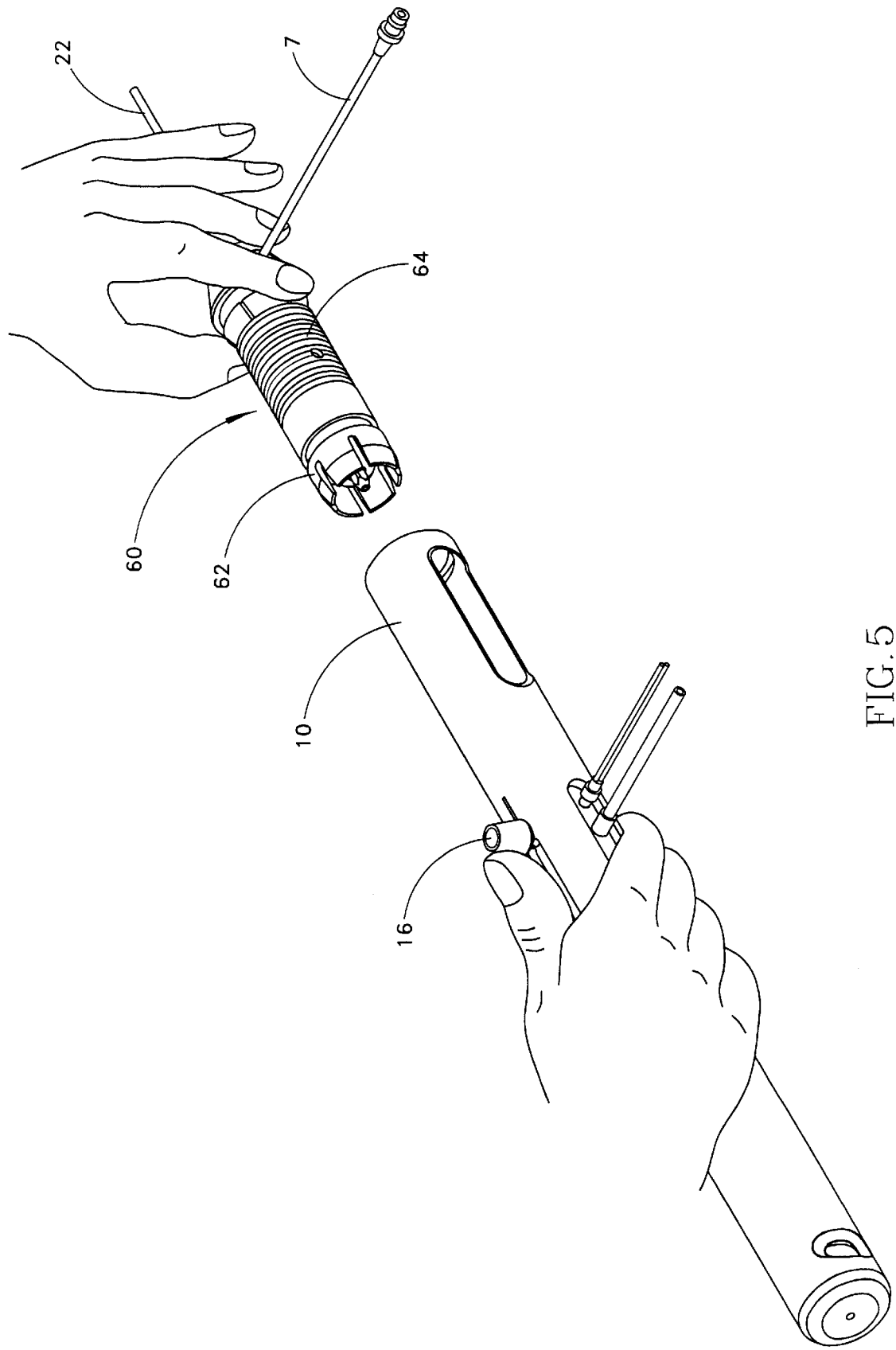
FIGS. 5–7 are perspective views illustrating the process of attaching the exchangeable drive shaft cartridge to the handle housing.
Figure 6:
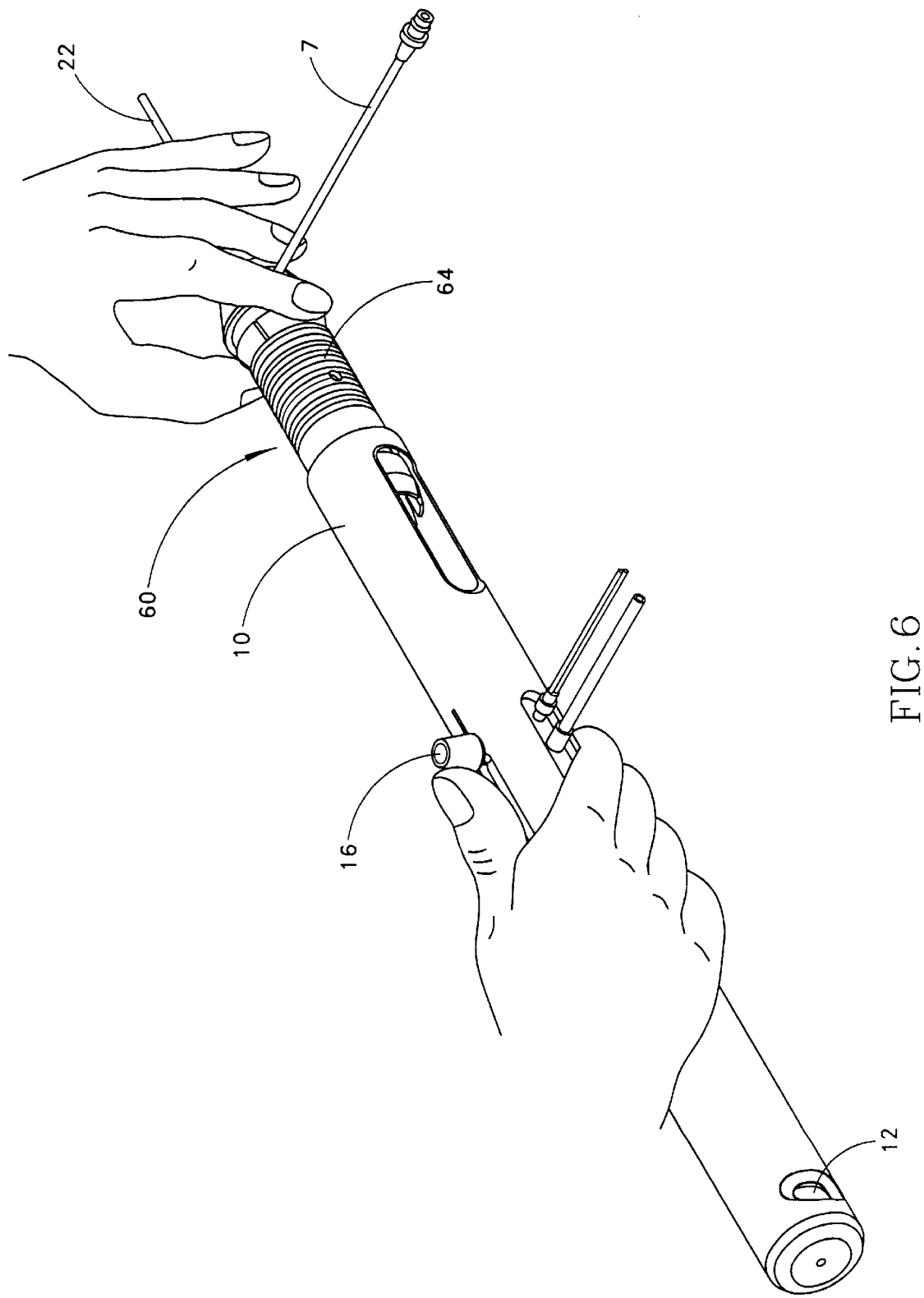
Figure 7:
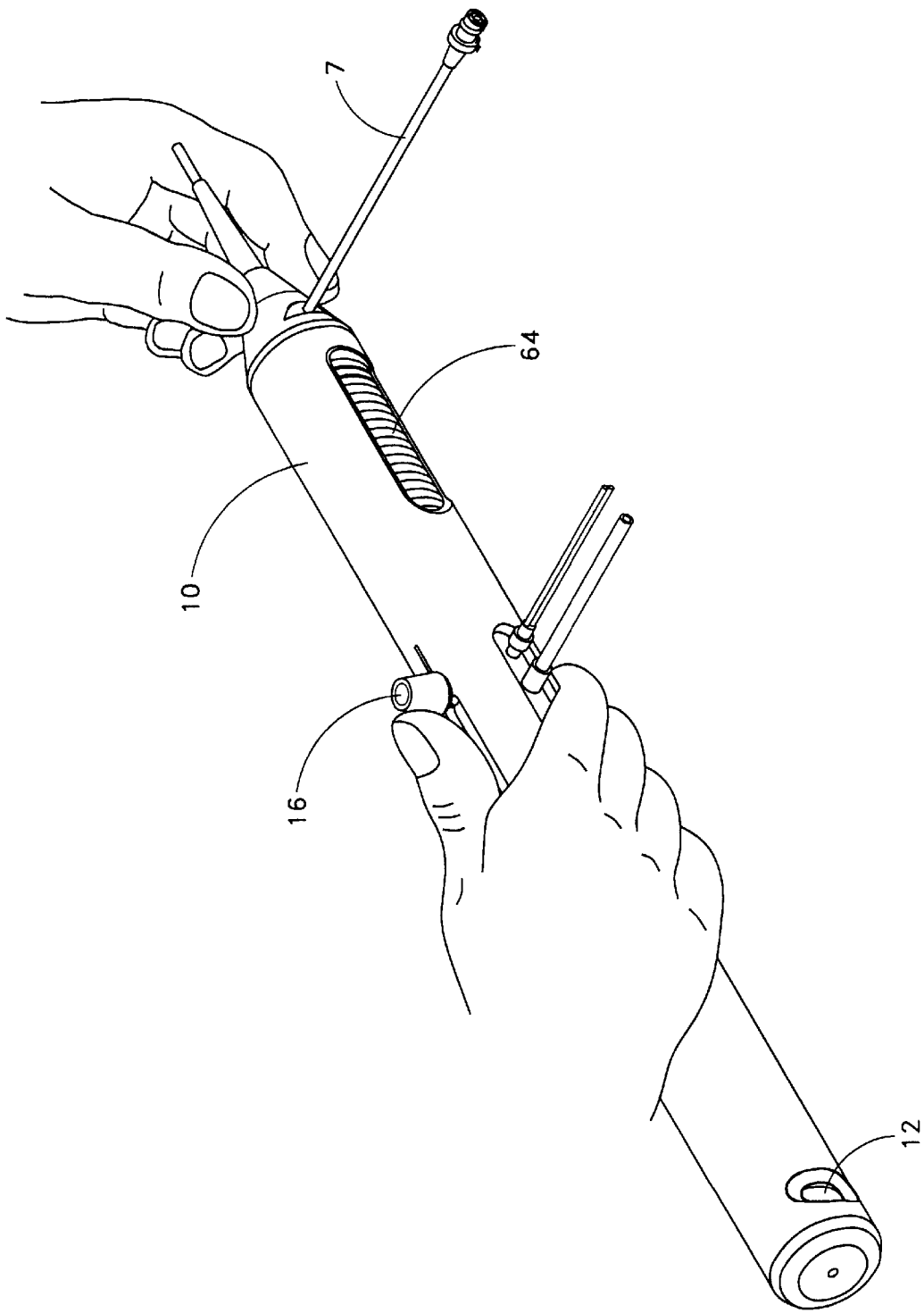

In FIG. 5 the user has manually aligned the proximal end of the exchangeable drive shaft cartridge 60 with the distal end of the handle housing 10. In FIG. 6 the user is inserting the cartridge 60 into the handle housing 10. In FIG. 7 the user has completed insertion of the cartridge 60 into the handle housing 10.

In FIGS. 5–7 the control knob 16 and the prime mover carriage 30 are shown in the cartridge exchange position and the user is pushing distally on the knob 16. FIGS. 8–12 and 15–16 illustrate the positions of key internal components with the user pushing distally on the control knob 16 while attaching the exchangeable drive shaft cartridge 60 to the handle housing 10. It should be noted, however, that it is not necessary to continuously push distally on the control knob 16 while attaching the exchangeable drive shaft cartridge 60 to the handle housing 10. In fact, if desired, the cartridge housing 62 can be attached to the handle housing 10 even when the control knob 16 is in its range of working positions—in this case, to complete the attachment of the exchangeable drive shaft cartridge 60 to the handle housing 10 (i.e., to insert the shank 82 into the socket 38 and to attach the tube 70 to the prime mover carriage 30), the user only needs to push the control knob 16 to its most distal position (i.e., enter the cartridge exchange position) and then retract it again to the range of working positions.

Figure 8:
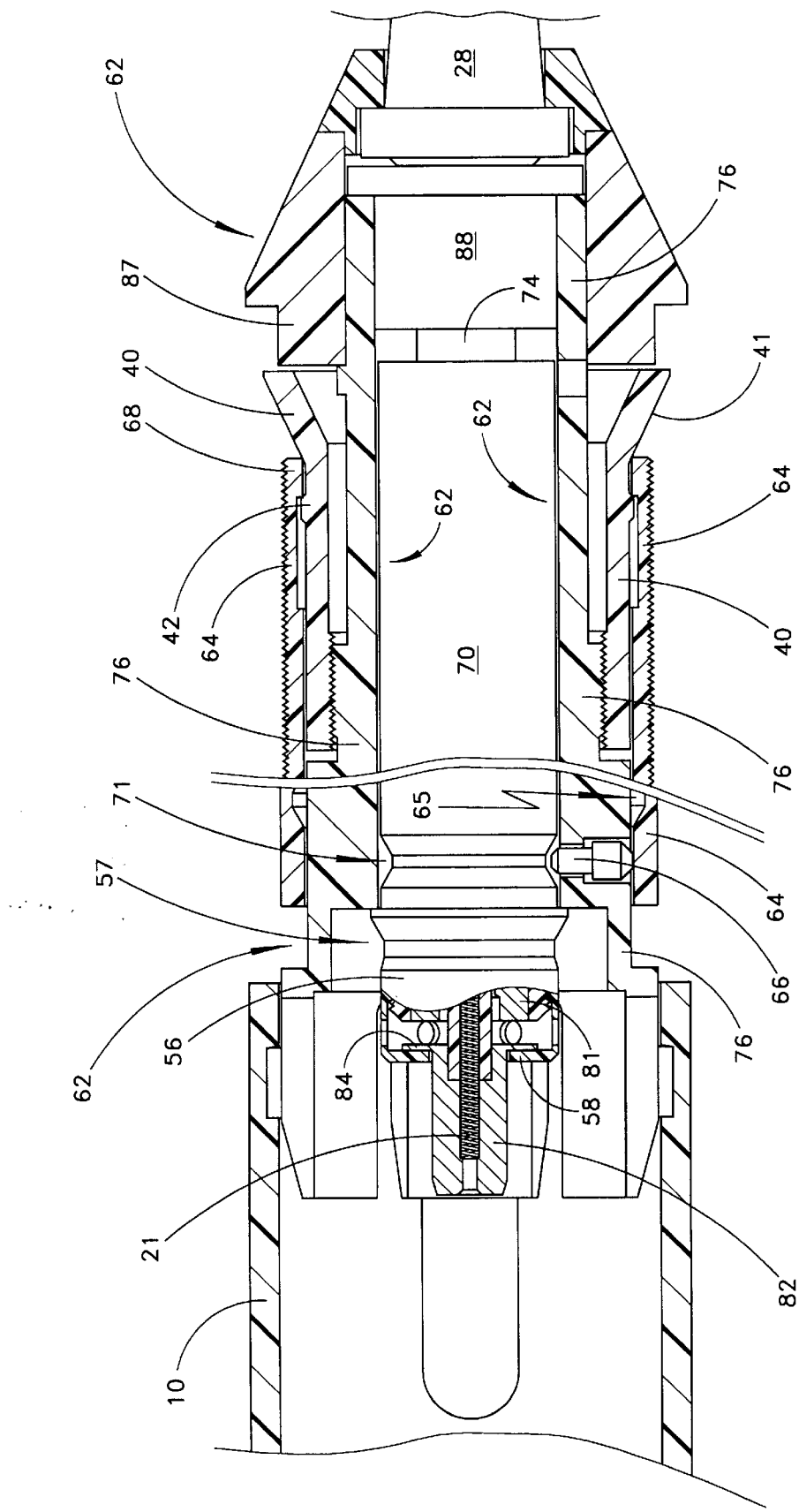
FIGS. 8–12 are longitudinal cross-sectional views illustrating the process of attaching one embodiment of an exchangeable drive shaft cartridge to the handle housing.
Figure 13:
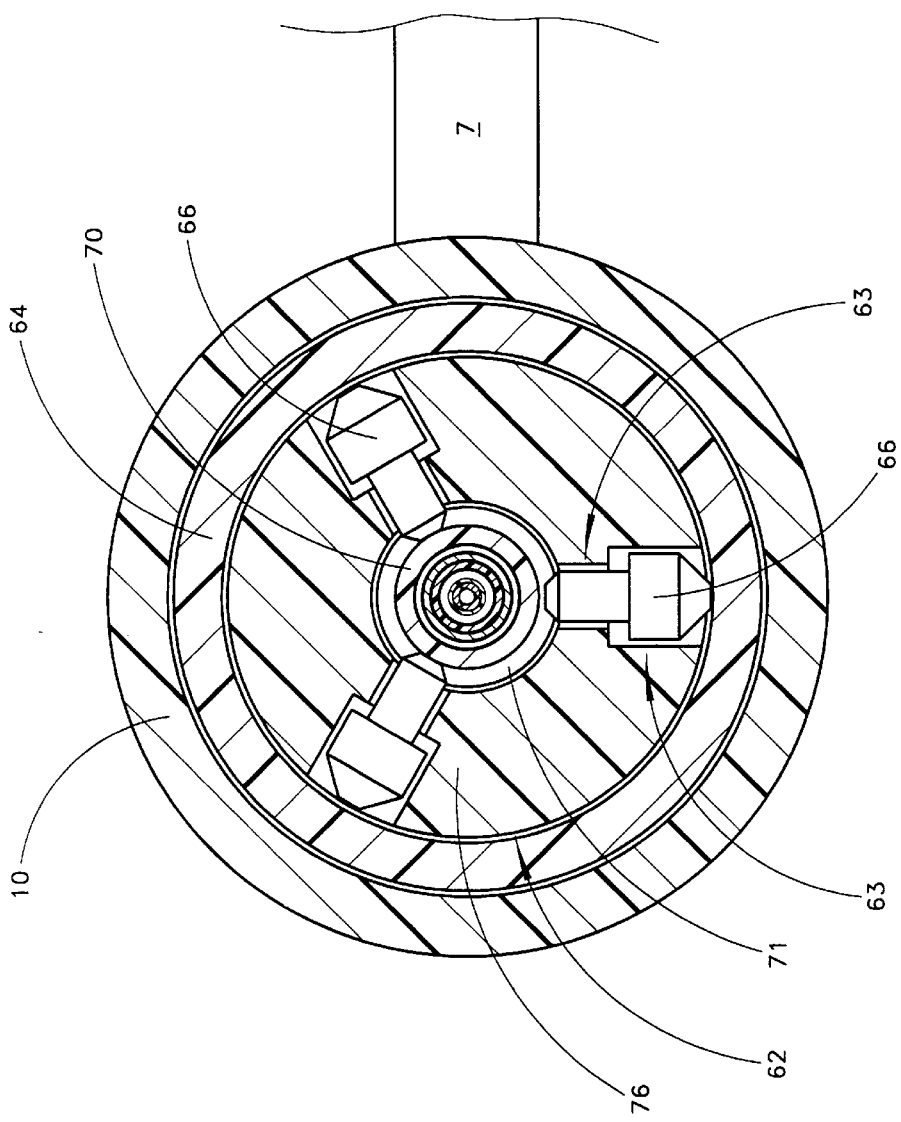
FIG. 13 is a transverse cross-sectional view of FIG. 12 taken along lines 13—13 thereof.
Figure 19:
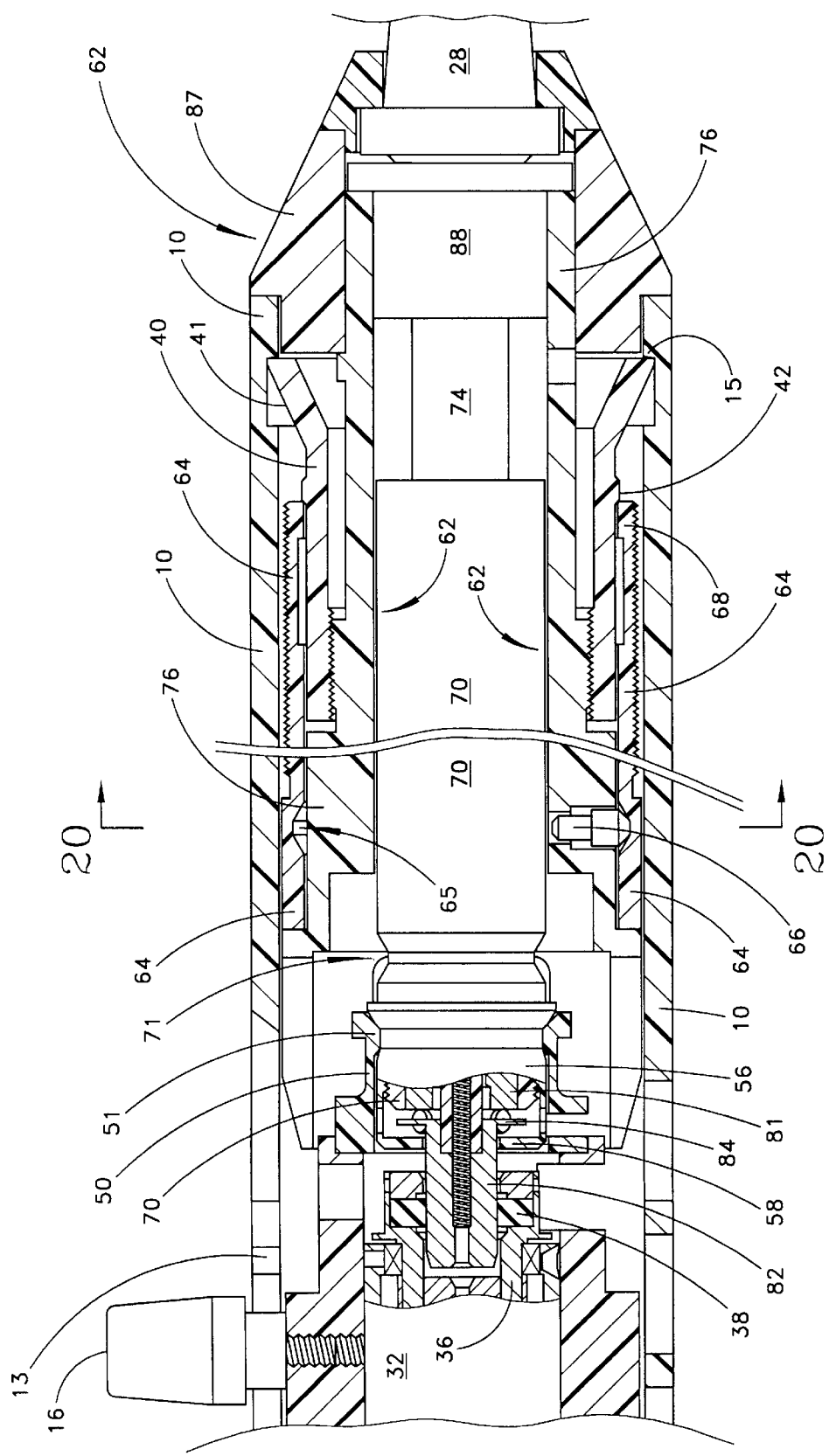
FIG. 19 is a broken away longitudinal cross-sectional view showing the prime mover carriage and the longitudinally movable tube in their range of working positions.

FIG. 8 is a cross-sectional view illustrating the beginning illustrating the beginning of the insertion of the exchangeable drive shaft cartridge 60 into the handle housing 10. FIGS. 9–10 illustrate further insertion of the cartridge 60 into the handle housing 10. In FIG. 10 the collar 56 (which forms the proximal end of the longitudinally movable tube 70) has engaged the radially resilient fingers 50 of the prime mover carriage 30, causing the fingers 50 and their detents 51 to deflect radially outwardly. FIG. 10 shows that the elongated shank 82 is approaching the prime mover socket 38, but has not yet engaged it. The insertion process is continued in FIG. 11, where the shank 82 has engaged the prime mover socket 38, and is completed in FIGS. 12–13. FIG. 12 shows that the user has completed insertion of the cartridge housing 62 into the handle housing 10 and the drive shaft shank 82 has been fully inserted into the prime mover socket 38. FIG. 13 is a cross-sectional view corresponding to FIG. 12. In FIG. 12 the distal camming surfaces of the radially resilient fingers 50 and the distal camming surface of the longitudinally movable tube 70 are positioned such that the radially resilient fingers 50 are deflected radially outwardly—once the prime mover carriage 30 is moved proximally to its range of working positions then the radially resilient fingers 50 regain their non-deflected shape, as is shown in FIG. 19 below, thereby removably attaching the longitudinally movable tube 70 to the prime mover carriage 30.

FIGS. 9–12 illustrate the latching function of a preferred cartridge latch that removably locks the cartridge housing 62 to the handle housing 10. The cartridge latch includes at least one, and preferably several, radially resilient fingers 40 which are carried by the tubular core 76 of the cartridge housing 62 (further details regarding the structure of the fingers 40 can be seen in FIGS. 38–39). The resilient fingers 40 are removably engageable with a complementary structure carried by the handle housing 10. The complementary structure may be of any suitable configuration, but preferably comprises a radially inwardly extending shoulder 15. Preferably the shoulder 15 is generally annular and is positioned near the distal end of the handle housing 10. Typically the shoulder 15 comprises a distal wall of a generally annular groove 18 formed in a wall of the handle housing 10, the groove 18 removably receiving therein the distal latching portions of the radially resilient fingers 40. The groove 18 is most easily seen in FIG. 53.

In the preferred embodiment shown in the drawings the radially resilient fingers 40 each have a portion with an outer surface 41 slanting distally radially outwardly. Thus, as is shown in FIG. 10–11, as the drive shaft cartridge 60 is inserted proximally into the handle housing 10, the distal end of the handle housing 10 causes the resilient fingers 40 to deflect radially inwardly. When the drive shaft cartridge 60 is fully inserted into the handle housing 10 (as is shown in FIG. 12), the distal ends of the fingers 40 have moved proximally past the shoulder 15, allowing them to spring back radially outwardly to the position shown in FIG. 12. In this position they lock the cartridge housing 62 to the handle housing 10.

As will be described in more detail in connection with FIGS. 43–49 below, the drive shaft cartridge 60 also includes a slide 64 which is longitudinally movable with respect to the cartridge housing 62 from a neutral position, where the cartridge latch is locked, to a cartridge unlocked position where the slide 64 unlocks the cartridge latch, thereby permitting the cartridge housing 62 to be removed from the handle housing 10. The slide 64 is shown in the neutral position in FIG. 12. Preferably the slide is generally tubular in shape, and is disposed about the cartridge housing 62 (i.e., its tubular core 76) so that distal movement of the slide 64 from its neutral position to its cartridge unlocked position moves the fingers 40 radially inwardly, thereby disengaging the fingers 40 from the shoulder 15 of the handle housing 10 and permitting the cartridge 60 to be removed from the handle housing 10.

FIGS. 12–20 illustrate the structure and function of a preferred tube latch which selectively locks the longitudinally movable tube 70 against longitudinal movement with respect to the cartridge housing 10. The tube latch effectively prevents inadvertent movement of the longitudinally movable tube 70 with respect to the cartridge housing 62 when the exchangeable drive shaft cartridge 60 is detached from the handle housing (keeping it stored safely within the cartridge housing 62), while permitting longitudinal movement of the tube 70 when the cartridge 60 is properly attached to a handle housing 10. The preferred tube latch shown in the drawings also selectively locks the slide 64 against longitudinal movement with respect to the cartridge housing—as is described in more detail below, this preferred tube latch is configured and arranged so that whenever the longitudinally movable tube 70 is locked against longitudinal movement with respect to the cartridge housing, then the slide 64 is longitudinally movable, and whenever the slide 64 is locked against longitudinal movement with respect to the cartridge housing, then the tube 70 is longitudinally movable. Thus, the slide 64 can be moved distally to unlock the cartridge latch only if the longitudinally movable tube 70 is secured against longitudinal movement by the tube latch.

To accomplish these functions, the preferred tube latch illustrated in the drawings includes a tube locking element in the form of a one or more locking pins 66 carried by the cartridge housing 62. The preferred embodiment utilizes three such locking pins 66, spaced generally evenly about the circumference of the cartridge housing 62 (more or fewer locking pins 66 could also be used). The tube locking pins 66 are radially movable between at least two positions, a tube locked position, where the tube locking pins 66 are moved radially inwardly (as is shown in FIGS. 12–13), thereby restricting longitudinal movement of the longitudinally movable tube 70 with respect to the cartridge housing 62, and a tube unlocked position, where the tube locking pins 66 are moved radially outwardly (as is described below in reference to FIGS. 16–20), thereby permitting longitudinal movement of the longitudinally movable tube 70 with respect to the cartridge housing 62.

As can be seen in FIGS. 12–13, preferably each tube locking pin 66 is disposed within a radial bore 63 in a wall of the tubular core 76 of the cartridge housing 62. The tube latch also includes a generally annular recess 71 formed in an outer surface of the longitudinally movable tube 70, the recess 71 receiving an inner portion of each of the tube locking pins 66 when the pins 66 are moved radially inwardly to their tube locked positions (although the tube's recess 71 is annular, it need not necessarily go all the way around the tube, though preferably it does). The tube latch also includes a generally annular recess 65 formed in an inner surface of the slide 64, the slide's annular recess 65 receiving an outer portion of each of the tube locking pins 66 when the pins 66 are moved radially outwardly to their tube unlocked position (although the slide's recess 65 is annular, like the tube's recess 71, it need not necessarily go all the way around the slide, though preferably it does).

In FIGS. 12–13, the recess 65 in the slide 64 is positioned distally of the tube locking pins 66. In this position the inner surface of the slide 64 retains the pins 66 in the tube locked position (i.e., moved radially inwardly), thus preventing longitudinal movement of the tube 70.

Figure 14:
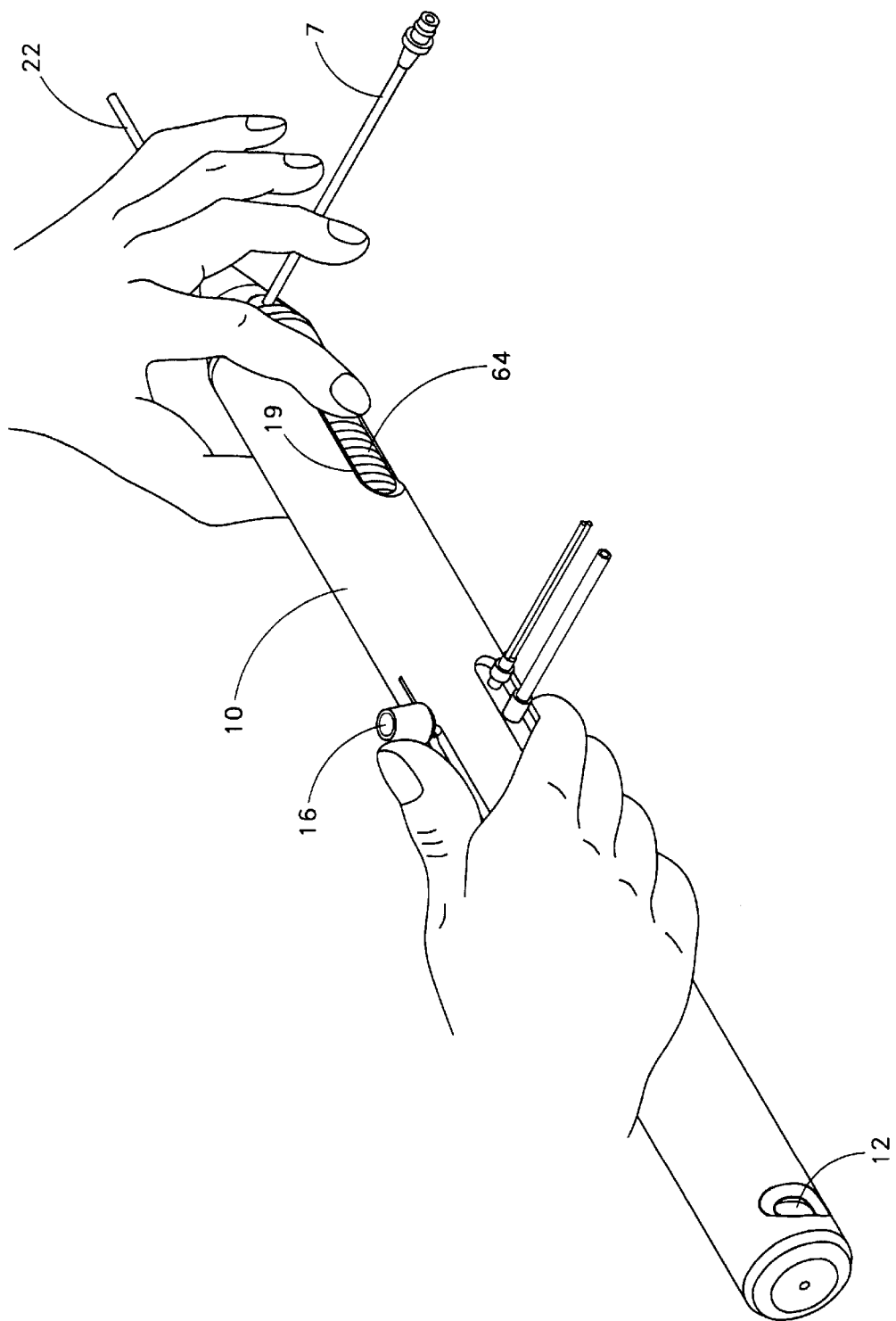
FIG. 14 is a perspective view illustrating an additional step required in the process of attaching one embodiment of an exchangeable drive shaft cartridge to the handle housing.
Figure 15:
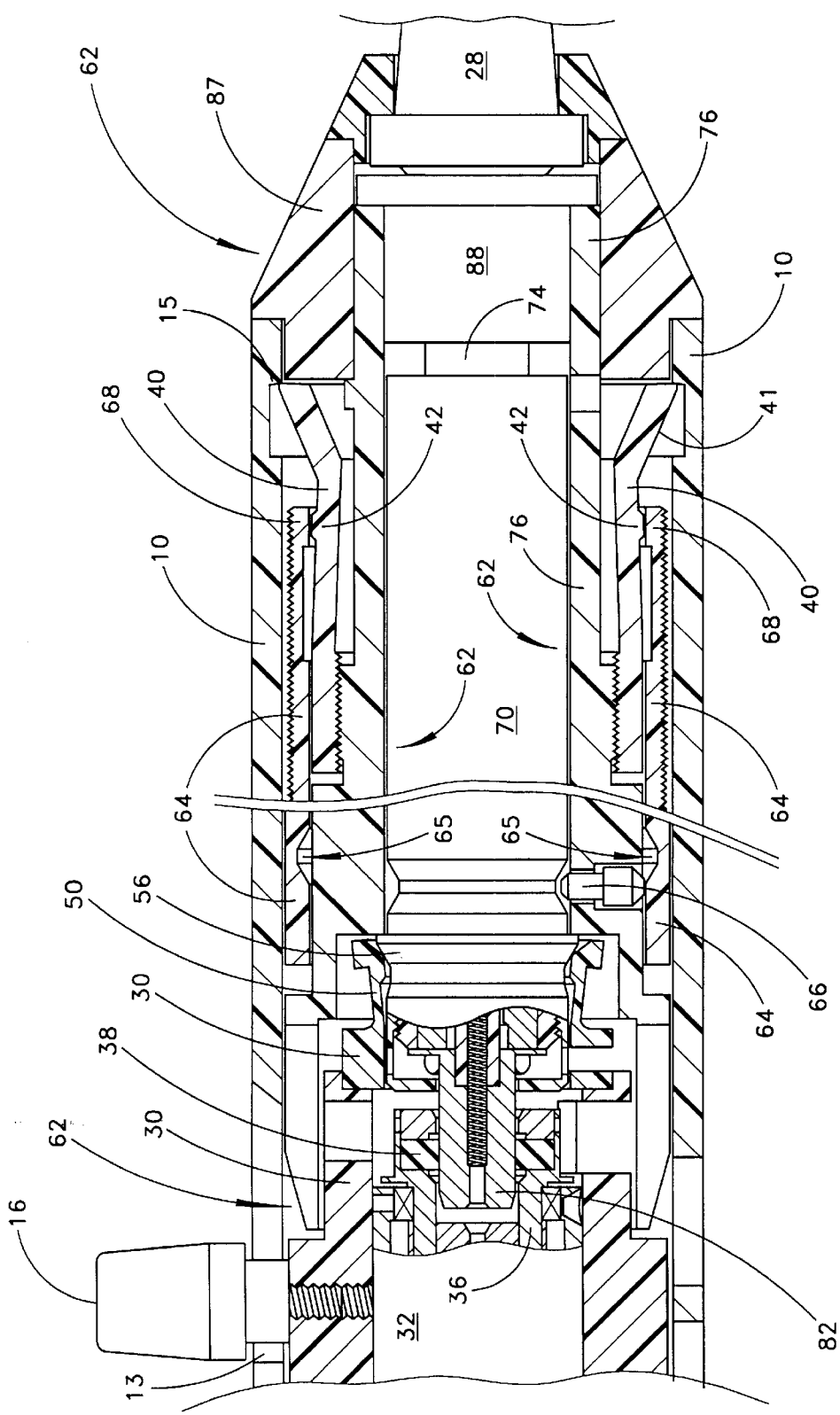
FIGS. 15–16 are longitudinal cross-sectional views illustrating the additional step shown in FIG. 14 of attaching the exchangeable drive shaft cartridge to the handle housing, FIG. 15 showing the slide being moved toward its working position and FIG. 16 showing the slide in its working position.
Figure 16:
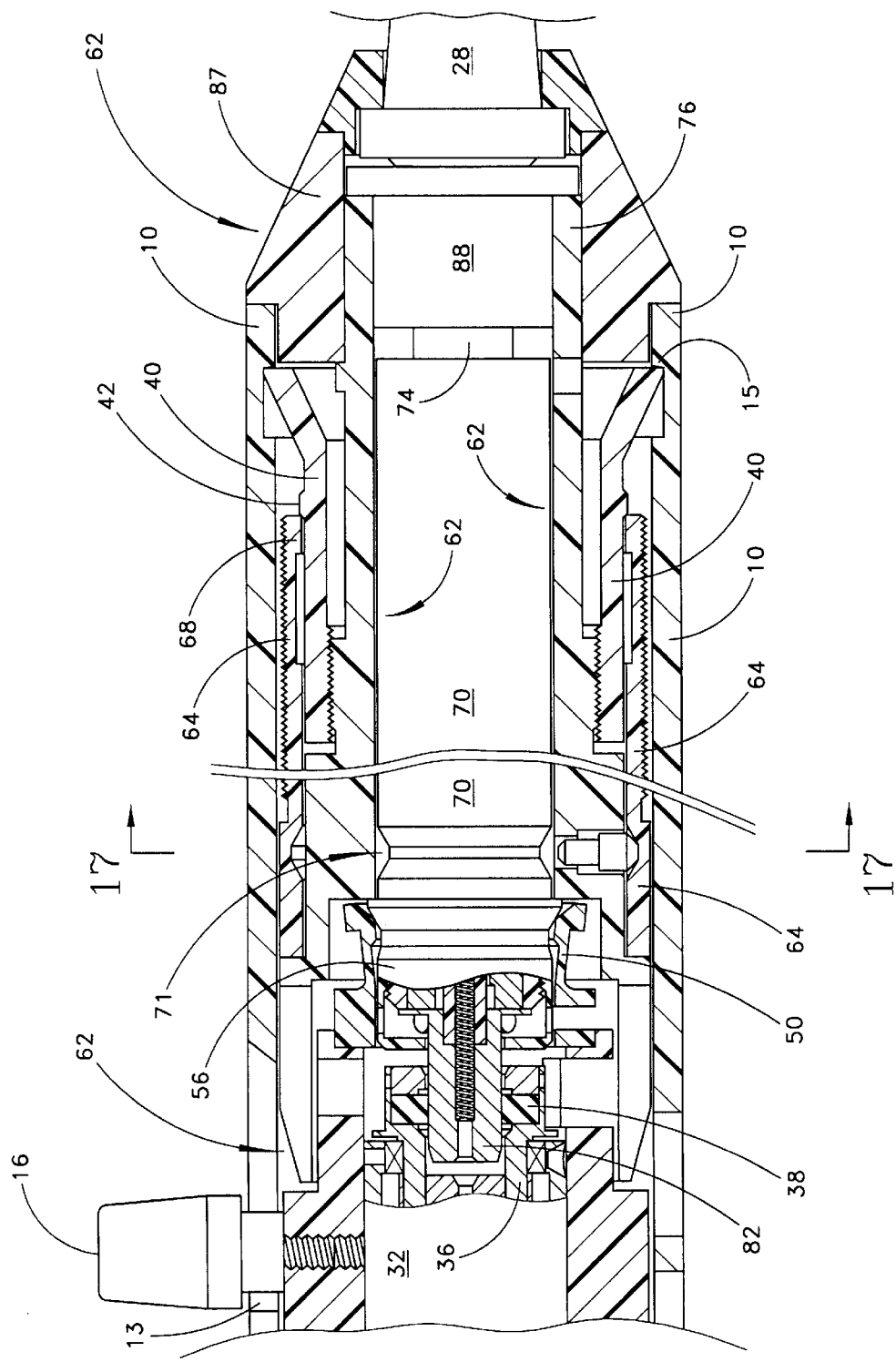

FIGS. 14–16 illustrate the next step in attachment of the exchangeable drive shaft cartridge 60 to the handle housing 10. In FIG. 14 the user has grasped the slide 64 through a pair of openings 19 (only one of which is visible in this drawing) formed in the wall of the handle housing 10. The user then moves the slide 64 proximally with respect to the cartridge housing 62 and the handle housing 10 so that the catch-engaging element 68 of the slide 64 moves over the catches 42 carried on the fingers 40, as is shown in FIG. 15. When the slide is moved to its working position (shown in FIG. 16) the annular recess 65 of the slide 64 is longitudinally aligned with the tube locking pins 66, thus permitting the tube locking pins 66 to move radially outwardly to their tube unlocked positions, thereby unlocking the longitudinally movable tube 70. This position of the slide 64 can be referred to as a working position, since it is the position of the slide 64 when the atherectomy device is used to perform an atherectomy procedure. Preferably the openings 19 are sufficiently long to permit manual movement of the slide 64 in a single motion from the neutral position to the working position.

Figure 17:
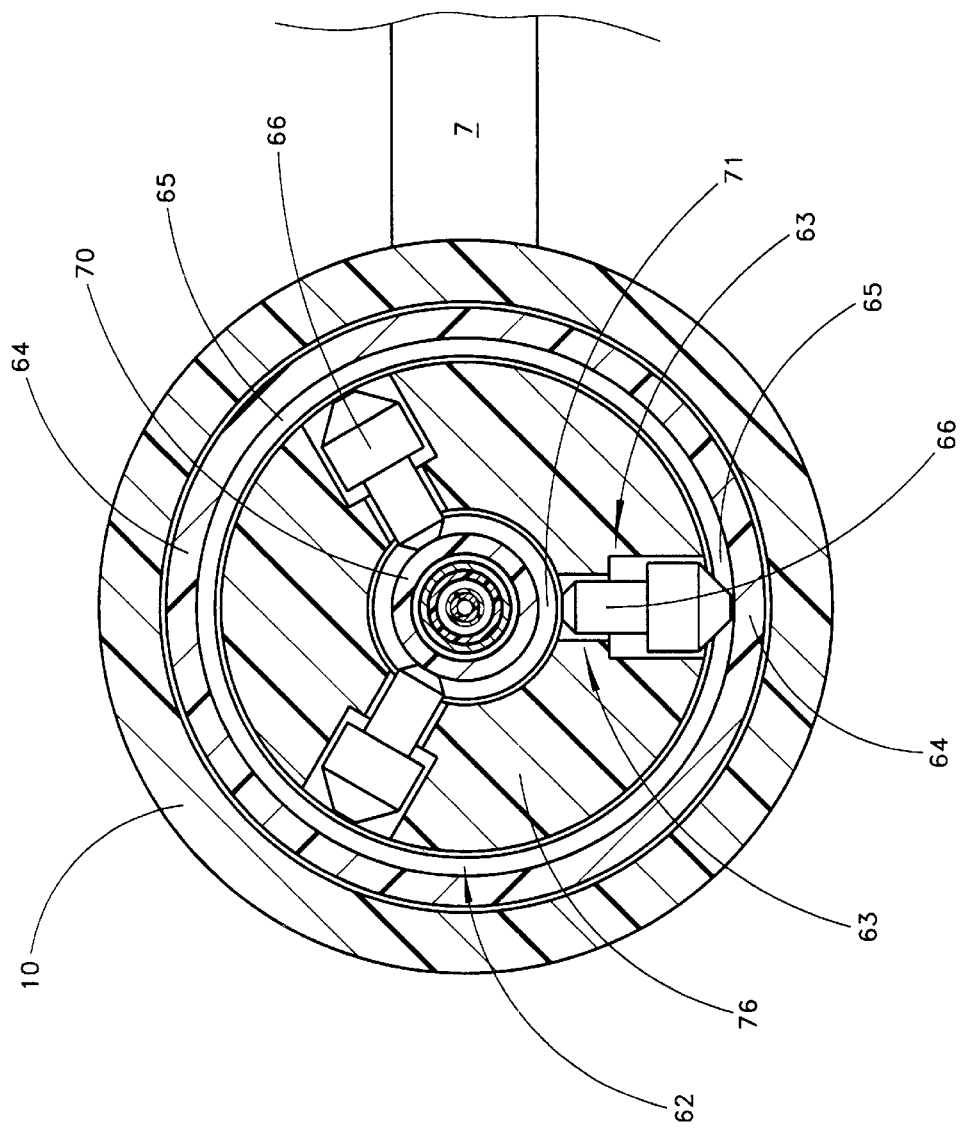
FIG. 17 is a transverse cross-sectional view of FIG. 16 taken along lines 17—17 thereof.

FIG. 17 is a transverse cross-sectional view showing the locations of the locking pins 66 when the annular recess 65 of the slide 64 and the annular recess 71 of the longitudinally movable tube 70 are aligned with the locking pins 76 in the cartridge housing 62 (i.e., as shown in FIG. 16). In this aligned position, the locking pins 66 are free to move both radially inwardly and radially outwardly—as depicted in FIG. 17, the locking pin located at the six o'clock position is shown as having dropped (due simply to gravity) into its tube unlocked position, while the locking pins in the two and ten o'clock positions are shown as being in their tube locked position. Desirably the inner and outer ends of the locking pins 66 are tapered. Preferably the annular recesses 65 and 71 have complementary surfaces which slope both proximally and distally. Consequently, when the components of the tube latch are in the position shown in FIGS. 16–17, either the slide 64 may be moved distally, thereby forcing all of the locking pins 66 radially inwardly to the tube locked position, or the tube 70 may be moved proximally, thereby forcing all of the locking pins 66 radially outwardly to their tube unlocked position.

Figure 18:
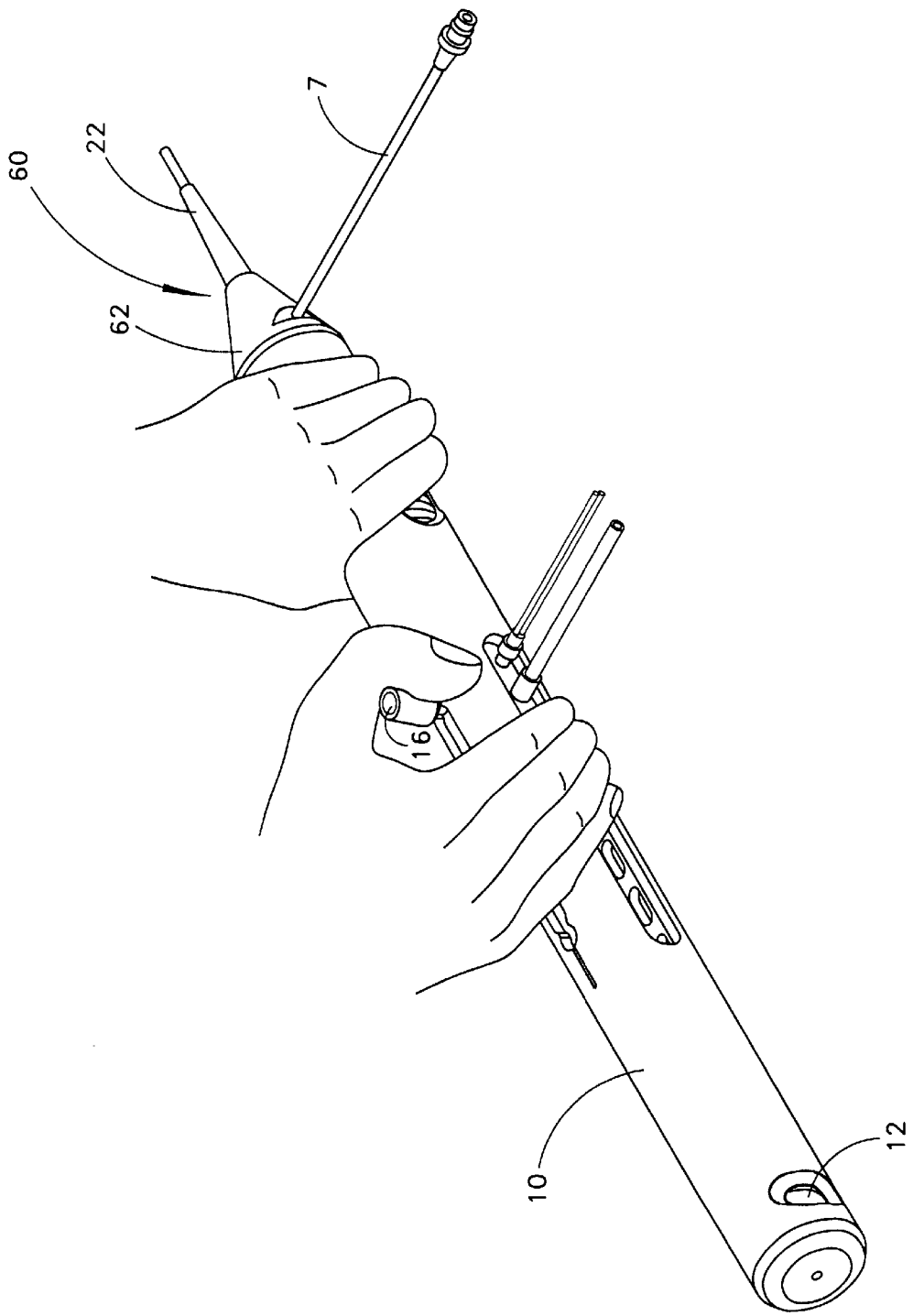
FIG. 18 is a perspective view showing the user moving the control knob and the prime mover carriage proximally to their range of working positions.
Figure 20:
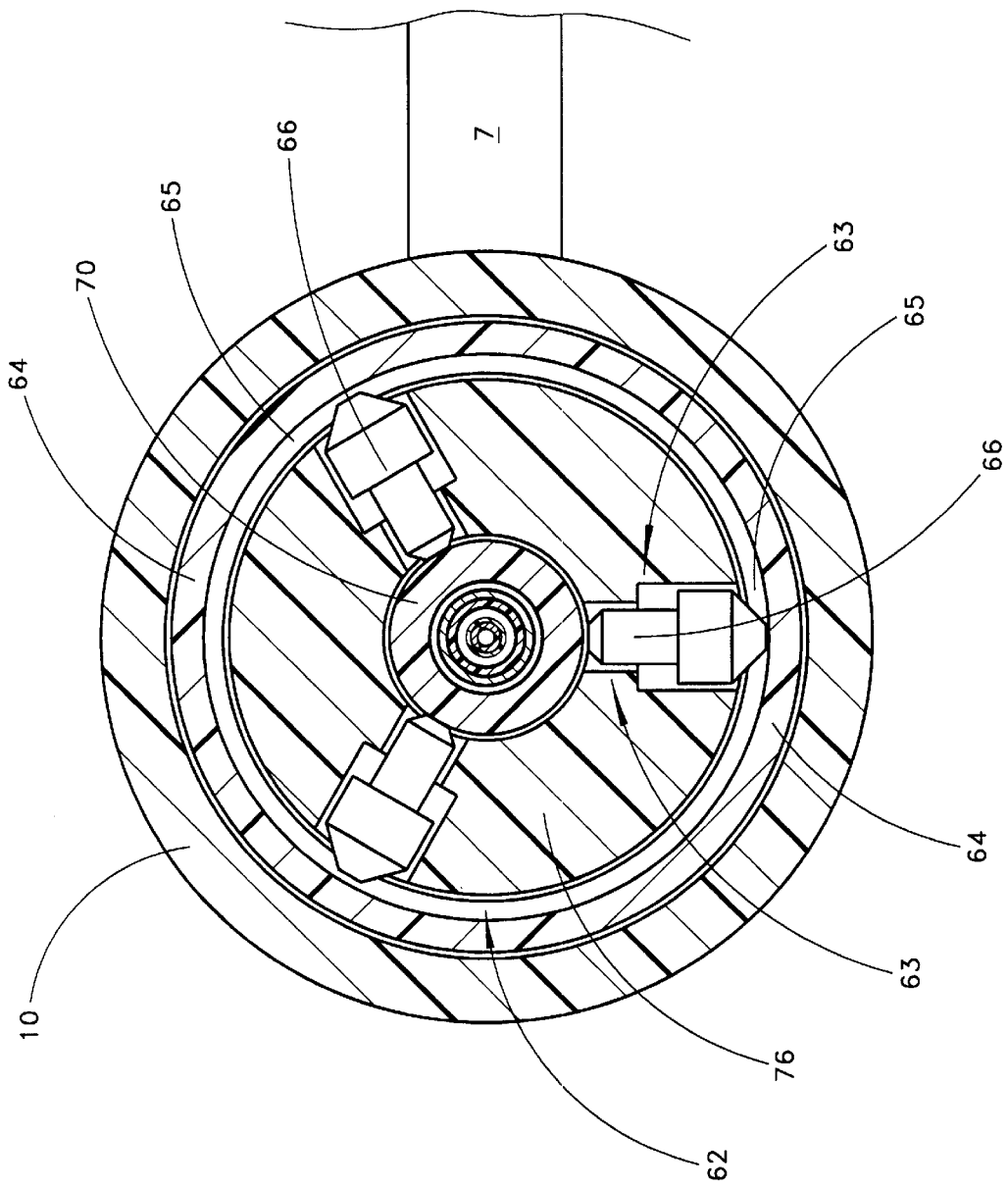
FIG. 20 is a transverse cross-sectional view of FIG. 19, taken along lines 20—20 thereof.

FIG. 18 shows the final step in attachment of the exchangeable drive shaft cartridge 60 to the handle housing 10. In this step the user manually grasps the control knob 16 to move it (together with the prime mover carriage 30 and the longitudinally movable tube 70) proximally to its range of working positions. FIGS. 19–20 illustrate the positions of the device's internal components after this movement has occurred. The annular recess 71 in the longitudinally movable tube 70 is no longer aligned with the locking pins 66. Thus, the tube 70 has moved the locking pins 66 outwardly to their tube unlocked positions, and the outer surface of the tube 70 retains the locking pins 66 in this position, thereby locking the slide 64 in its working position and preventing inadvertent distal movement of the slide 64 to its cartridge unlocked position where the cartridge latch is released. Note that in FIG. 19 the pressure urging the longitudinally moveable tube 70 and the prime mover carriage 30 toward each other has been released. Consequently, the radially resilient fingers 50 of the prime mover carriage 30 have regained their non-deflected configuration and their distal camming surfaces have slid back to their stable position with respect to the distal camming surface of the movable tube 70 (i.e., the collar 56 which forms the proximal end of the tube 70). In this position, the flange 84 of the drive shaft shank 82 is spaced away from both the distal and proximal abutment surfaces associated with the longitudinally movable tube 70 to permit free rotation of the shank 82 with respect to the tube 70.

Figure 21:
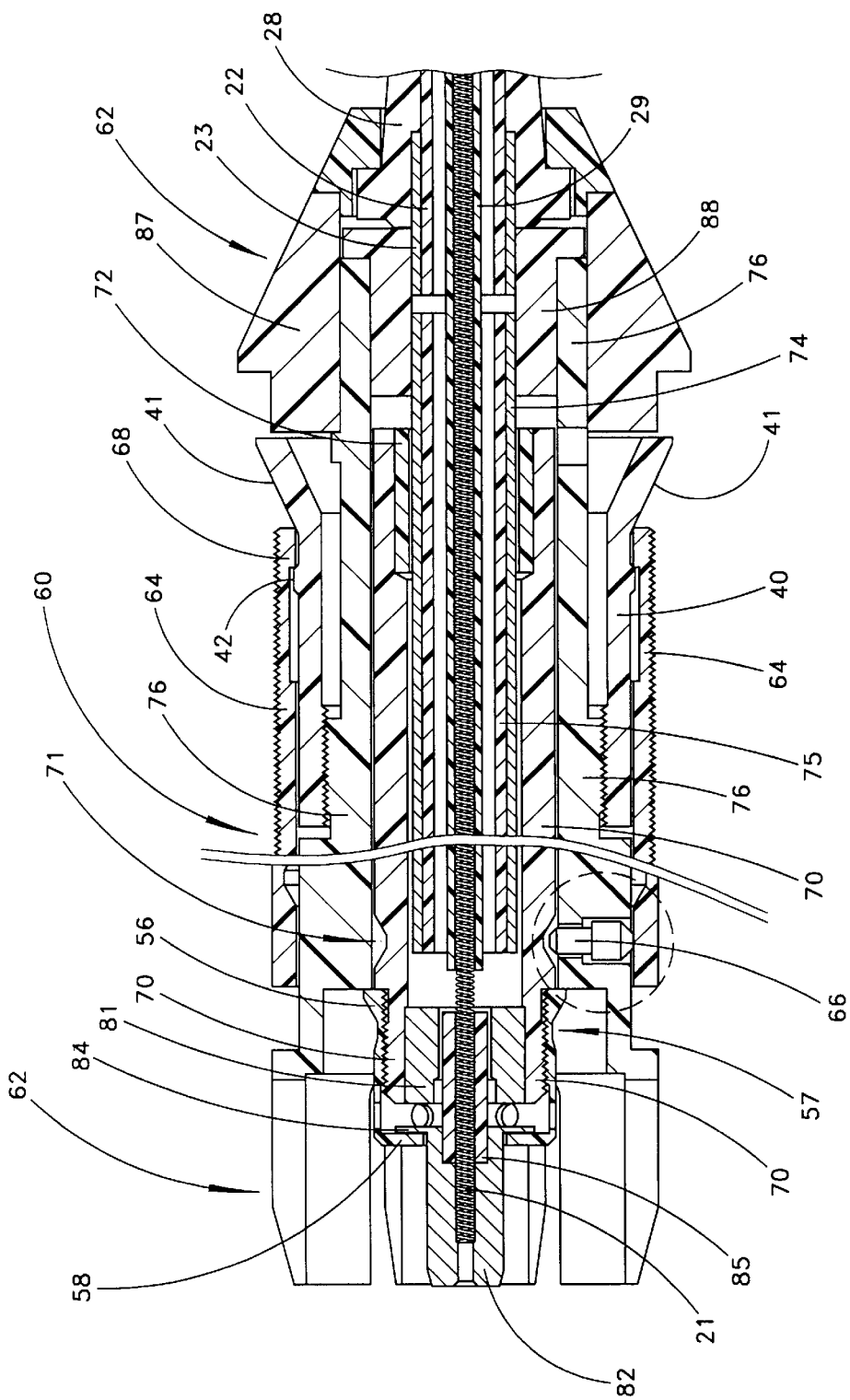
FIG. 21 is a broken-away longitudinal cross-sectional view of the proximal portion of the exchangeable drive shaft cartridge.
Figure 30:
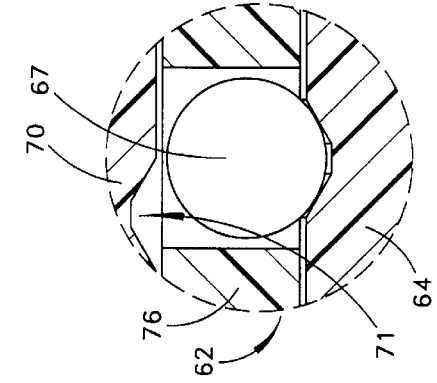
FIGS. 30–37 are enlarged views similar to FIGS. 22–29 showing an alternate embodiment of the tube latch, illustrating the tube latch in its various positions during attachment, use, and detachment of the exchangeable drive shaft cartridge.
Figure 31:
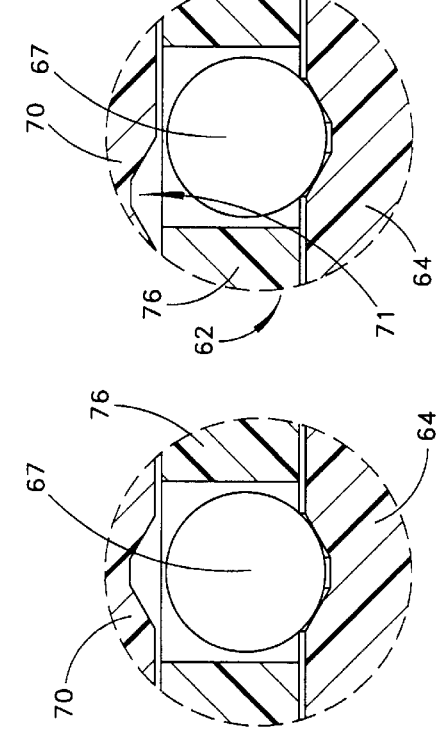
Figure 32:
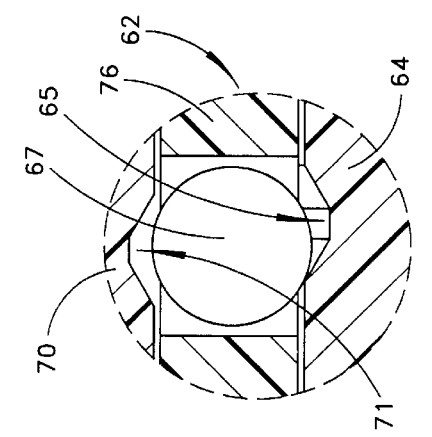
Figure 33:
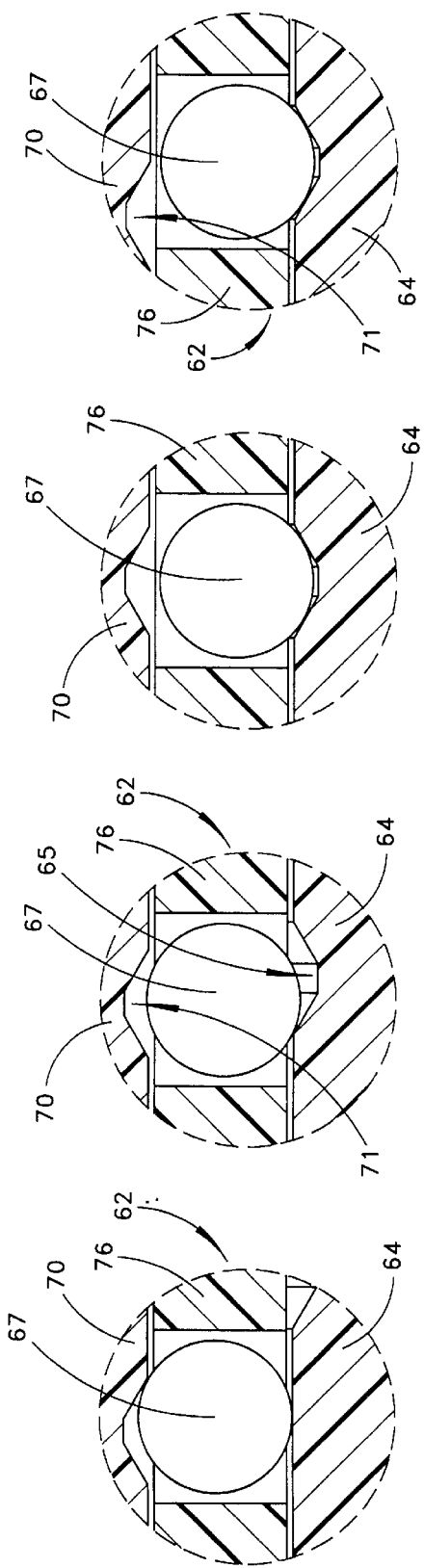
Figure 34:
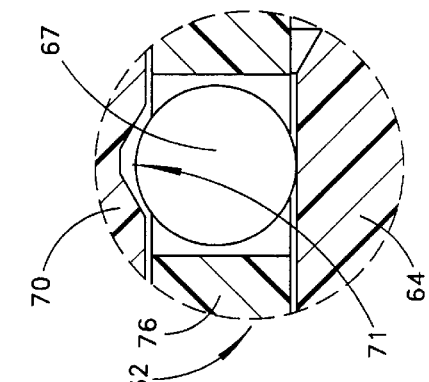
Figure 35:
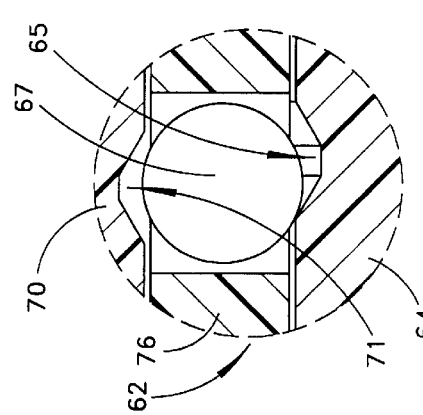
Figure 36:
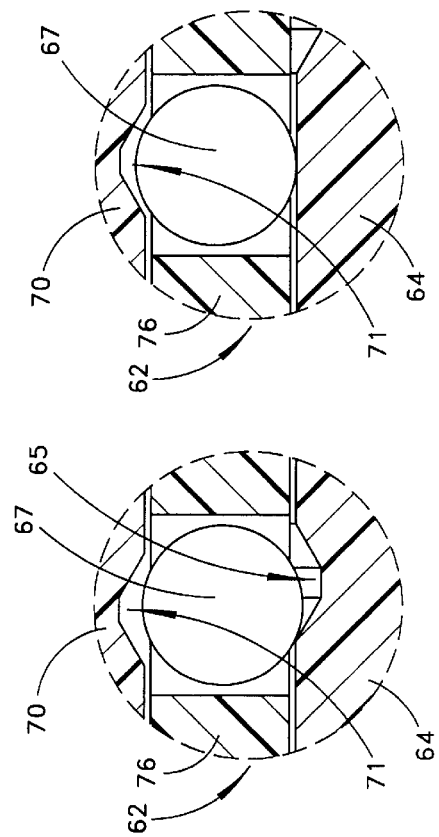
Figure 37:
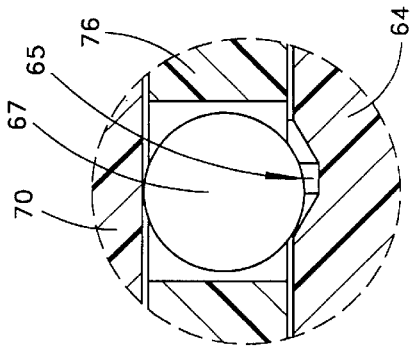

FIG. 21 shows in longitudinal cross-section the exchangeable drive shaft cartridge 60 prior to its attachment to the handle housing 10. The tube locking elements (locking pins 66) of the tube latch are in their radially inward tube locked positions (i.e., moved radially inwardly), retaining the longitudinally movable tube 70 within the cartridge housing 62, and the slide 64 is in its neutral position, retaining the tube locking elements (locking pins 66) in their tube locked positions.

FIGS. 22–29 illustrate a full cycle of positions of the tube latch elements. FIG. 22 essentially corresponds to the position shown in FIG. 21 (the tube 70 has been moved proximally slightly in comparison to FIG. 21, but the locking pins 66 lock the tube against substantial proximal movement). In FIG. 23, the drive shaft cartridge has been inserted into the handle housing, and the slide 64 is being moved proximally by the user to align the annular recess 65 of the slide 64 with the annular recess 71 of the tube 70. In FIG. 24 such alignment is completed, permitting the radially movable locking pin 66 to move from its tube locked position to its tube unlocked position. In FIGS. 25 and 26 the user is moving the control knob 16 (together with the prime mover carriage 30 and the longitudinally movable tube 70) proximally to the range of working positions. Consequently the tube's annular recess 71 is moved out of alignment with the locking pin 66, the radially movable locking pin 66 being retained in its tube unlocked position by the outer surface of the longitudinally movable tube 70, thereby locking the slide 64 in its working position.

When the user wishes to remove the exchangeable drive shaft cartridge 60 from the handle housing (e.g., to use a tissue removing implement of another size or type), the user returns the control knob 16 (together with the prime mover carriage 30 and the longitudinally movable tube 70) to its most distal position, thereby positioning the longitudinally movable tube 70 in its tube lockable position. In this position (shown in FIG. 27) the annular recess 71 of the tube 70 is aligned with the radially movable locking pin 66. From this tube lockable position the user can move the slide 64 distally to release the cartridge latch (as is described in more detail below). In FIG. 28 the slide 64 has been moved just slightly distally, the sloped surface of the annular recess 65 urging the locking pin 66 radially inwardly toward its tube locked position. In FIG. 29 the slide 64 has been moved sufficiently distally that the locking pin 66 is retained in its tube locked position, preventing longitudinal movement of the tube 70.

FIGS. 22–29 show some of the details of the radially movable locking pin 66 which functions as the tube locking element of the tube latch. Desirably its radially inner and outer ends are tapered to facilitate its inward or outward movement in response to longitudinal movement of the slide 64 or the tube 70. The locking pin 66 shown in FIGS. 22–29 is generally elongated, having a generally round transverse cross-section. The radially inner portion has a slightly smaller diameter than the radially outer portion, creating a shoulder in the intermediate portion of the pin. This shoulder engages a complementary shoulder formed in the radial bore 63 of the tubular core 76 of the cartridge housing 62—these shoulders are optional, being used simply to facilitate manufacturing assembly of the drive shaft cartridge (they prevent the pins 66 from passing all the way through the radial bores 63).

FIGS. 30–37 illustrate another configuration of a tube locking element. In this embodiment the tube locking element is simply a spherical locking ball 67. The positions of the radially movable locking ball 67 (and other tube latch components) in FIGS. 30–37 correspond to the positions of FIGS. 22–29. The spherical locking ball 67 is cheaper (since standard balls are readily commercially available) than the locking pin 66, and functions entirely adequately.

Figure 38:
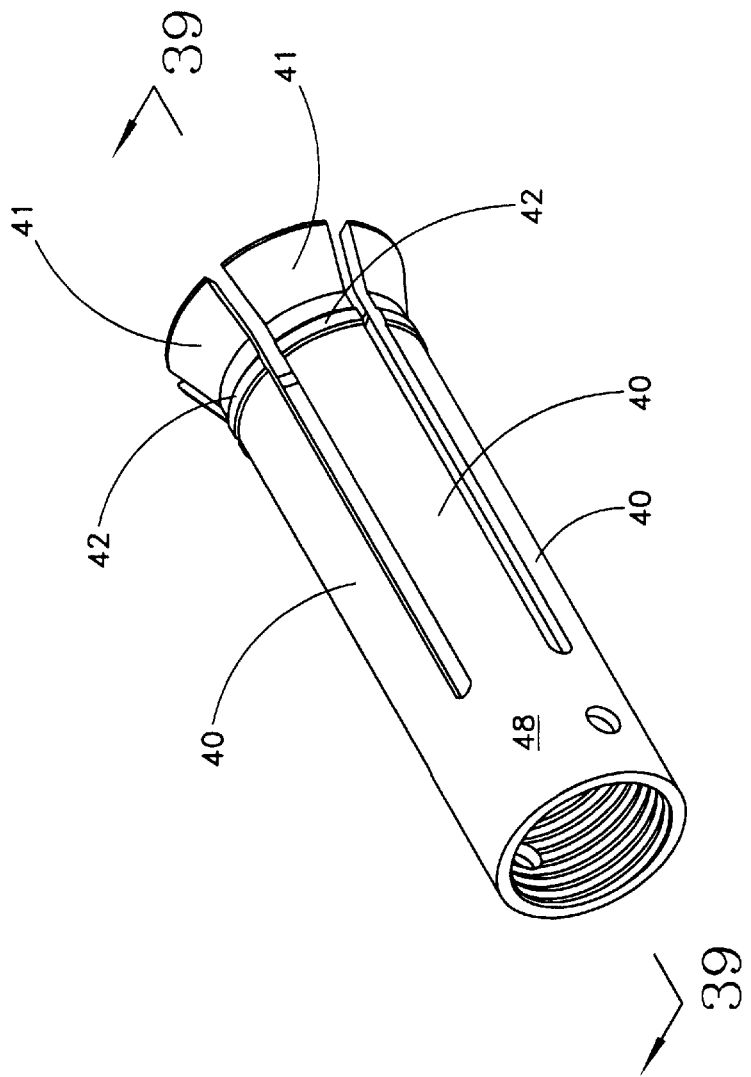
FIG. 38 is a perspective view of the radially resilient fingers of the cartridge latch.
Figure 39:
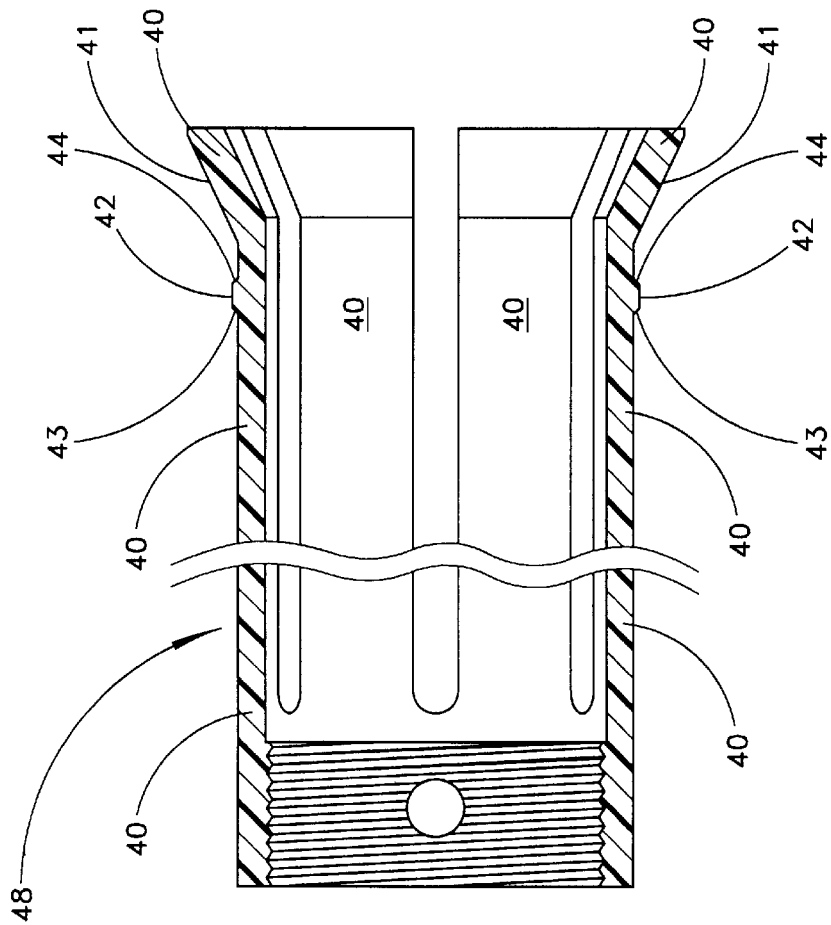
FIG. 39 is a cross-sectional view of FIG. 38, taken along lines 39—39 thereof.

FIGS. 38–39 illustrate a preferred embodiment of a latching component 48. The latching component 48 includes a plurality of radially resilient fingers 40 extending distally from a generally tubular proximal portion. In this embodiment the latching component 48 includes six radially resilient fingers 40, but a larger or smaller number of fingers 40 may be used. Each radially resilient finger 40 has a portion with an outer surface 41 slanting distally radially outwardly. As is described below in reference to FIGS. 43–49, during detachment of the exchangeable drive shaft cartridge 60 from the handle housing 10, the slide 64 is moved distally with respect to the radially resilient fingers 40, thereby causing the abutment surface of the slide (i.e., the distal end of the slide 64) to engage the slanted outer surfaces 41 of the fingers 40 and to move the fingers radially inwardly. Such radially inward movement of the fingers 40 disengages them from the complementary structure of the handle housing 10 and permits the cartridge housing 62 to be removed from the handle housing 10.

In FIGS. 38–39 the latching component 48 is shown as being manufactured as a separate piece, but it can be machined or injection molded integrally with the rest of the cartridge housing 62. In FIGS. 38–39 the proximal portion of the latching component 48 is internally threaded for connection to complementary external threads formed on the tubular core 76 of the cartridge housing 62. Such threads are not necessary, as the latching component 48 can simply be glued to the tubular core 76 of the cartridge housing 62.

FIGS. 38–39 also illustrate the configuration and position of a catch 42 extending radially outwardly from each of the resilient fingers 40. As is described in more detail below, the catches 42 are positioned to engage a complementary catch-engaging element 68 of the slide 64 (identified in, e.g., FIGS. 42 and 46–47), the catches 42 restricting free movement of the slide 64 between its neutral position and its working position. The catches 42 include proximal and distal engagement surfaces 43 and 44. The distal engagement surface 44 of each catch 42 preferably is slanted proximally radially outwardly so that movement of the slide 64 proximally from its neutral position causes the catch-engaging element 68 to engage the distal engagement surface 44 of the catch 42 to move the catch 42, together with the radially resilient finger 40, radially inwardly a distance sufficient to release the catch-engaging element 68 of the slide 64 from the catch 42. As is illustrated in FIG. 15, such interaction between the catch-engaging element 68 and the catch 42 permits the slide 64 to be manually moved from its neutral position to its working position. The proximal engagement surface 43 of the catch 42 preferably is slanted distally radially outwardly so that movement of the slide 64 distally from its working position causes its catch-engaging element 68 to engage the proximal engagement surface 43 of the catch 42 to move the catch 42, together with the radially resilient finger 40, radially inwardly a distance sufficient to release the catch-engaging element 68 of the slide 64 from the catch 42, thereby permitting the slide 64 to be manually moved distally out of its working position to (and beyond) its neutral position (as is shown in FIGS. 43–47). If desired, however, the proximal and distal engagement surfaces 43 and 44 need not be slanted if the catch-engaging element of the slide includes appropriately slanted surfaces.

FIGS. 40–50 illustrate the process of detaching an exchangeable drive shaft cartridge 60 from a handle housing 10 so that one drive shaft cartridge may be replaced by another drive shaft cartridge having a different size or type tissue removal implement.

Figure 40:
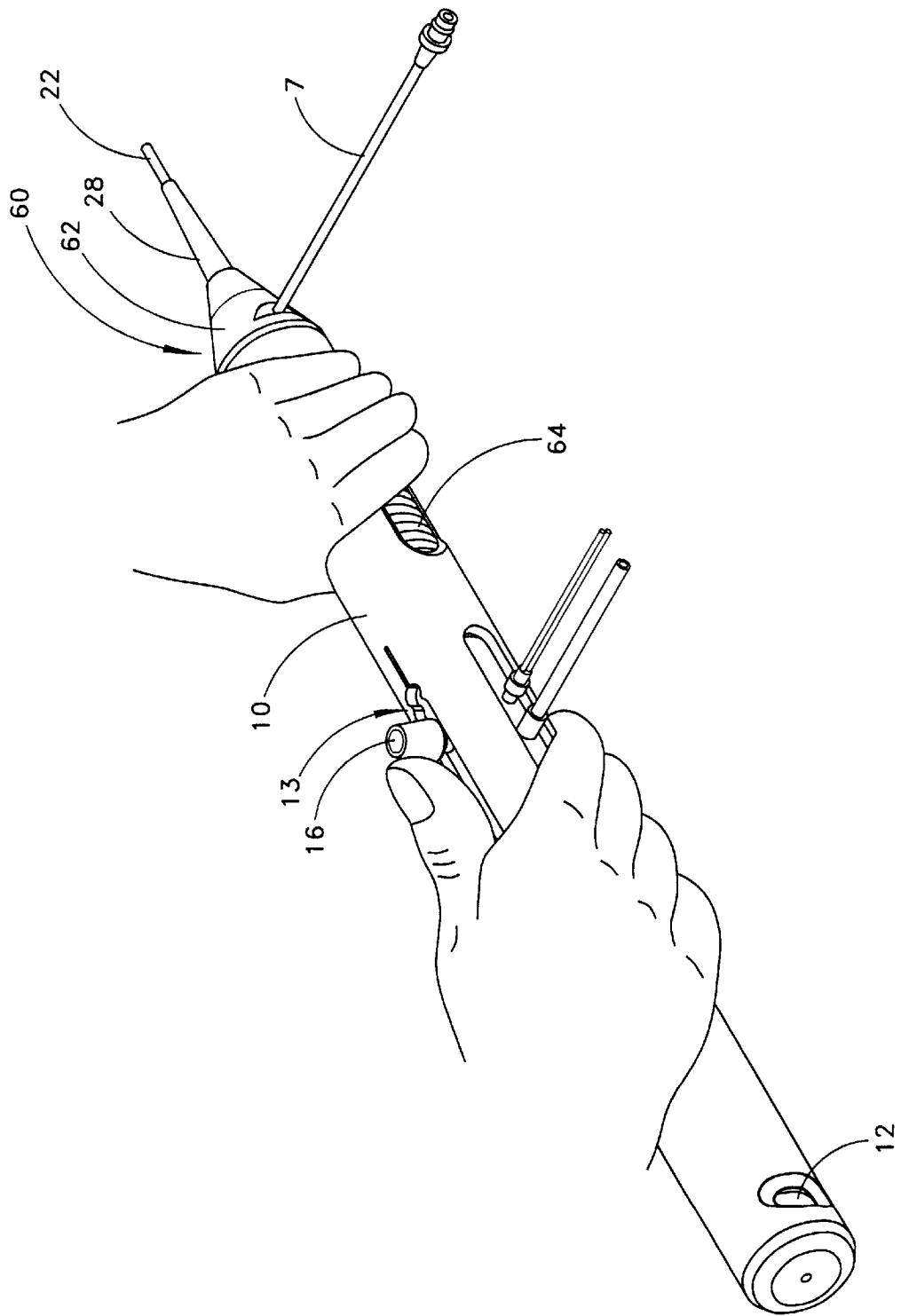
FIGS. 40–42 illustrate the first step in the process of detaching the cartridge housing from the handle housing, FIGS. 40 and 41 being perspective views, and FIG. 42 being a broken-away longitudinal cross-sectional view of FIG. 41.
Figure 41:
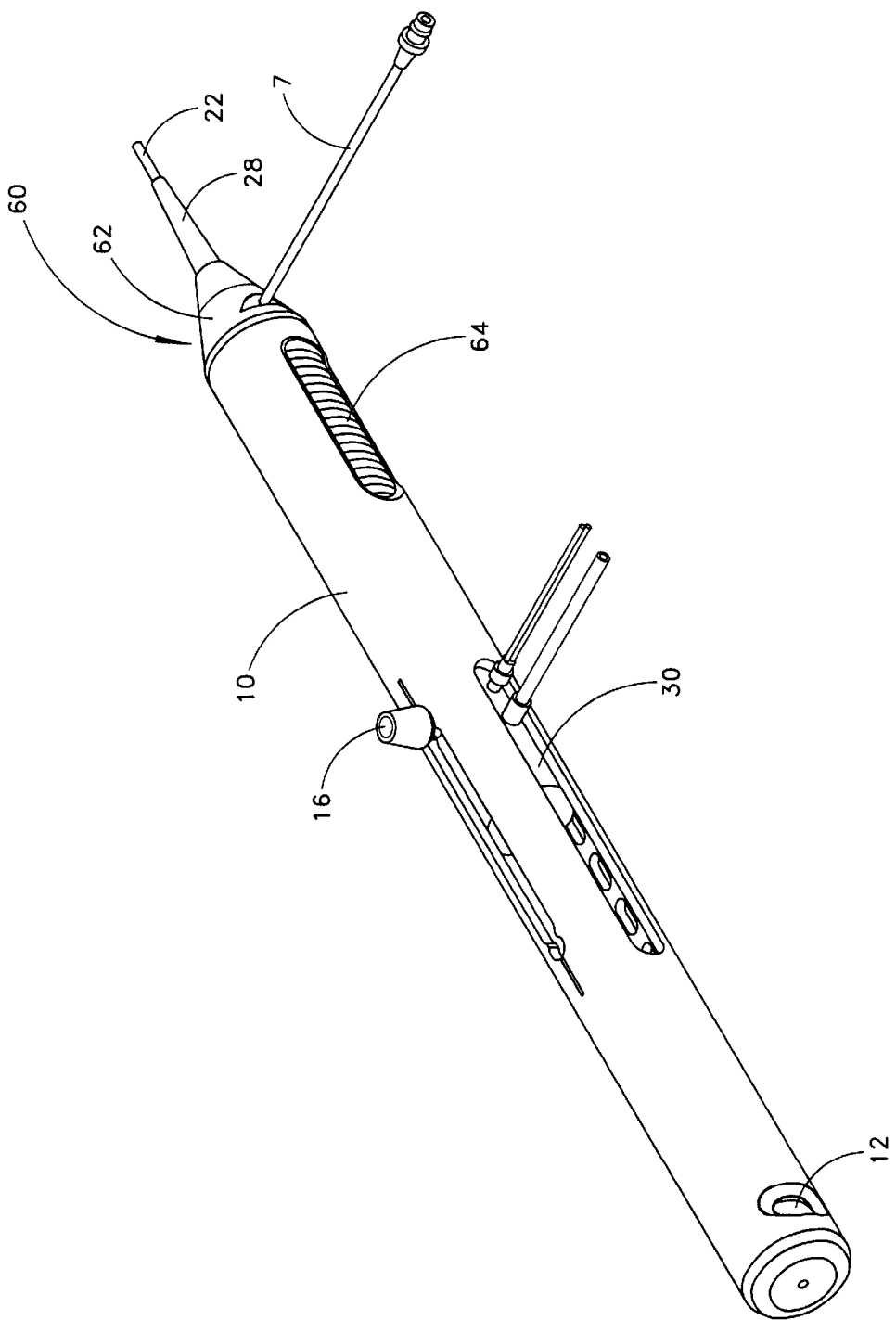
Figure 42:
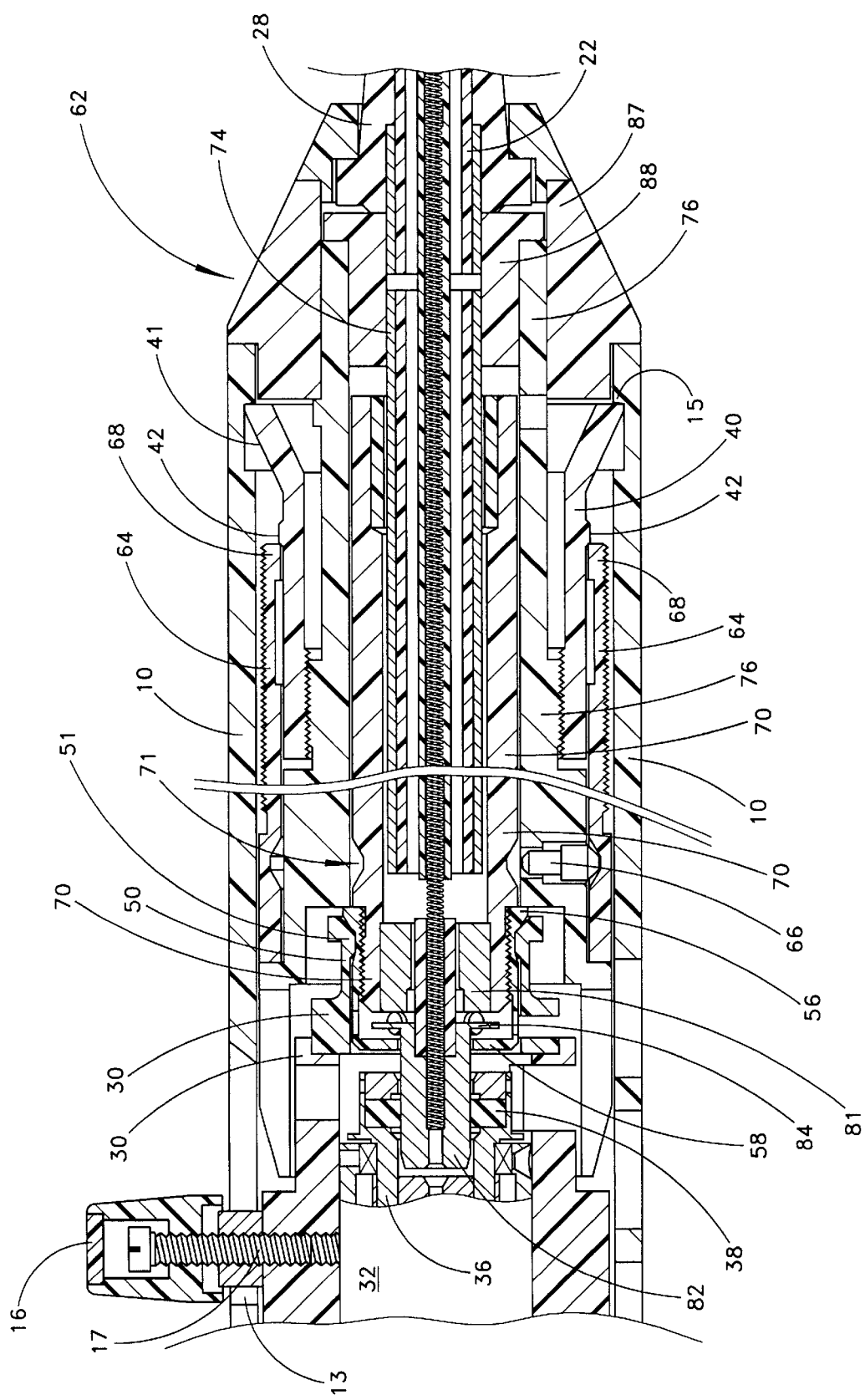

In FIG. 40 the user is advancing the control knob 16 (together with the prime mover carriage 30 and the longitudinally movable tube 70) distally to the cartridge exchange position shown in FIGS. 41 and 42 (As is described above, the cartridge exchange position is the position where the control knob 16 and its shaft 17 are located distally of the narrowed segment 13 of slot 11.) In the cartridge exchange position the longitudinally movable tube 70 is advanced distally to its tube lockable position. In this tube lockable position the tube latch permits the slide 64 to be moved longitudinally out of its working position. In FIG. 42 the slide 64 is still in its working position.

Figure 43:
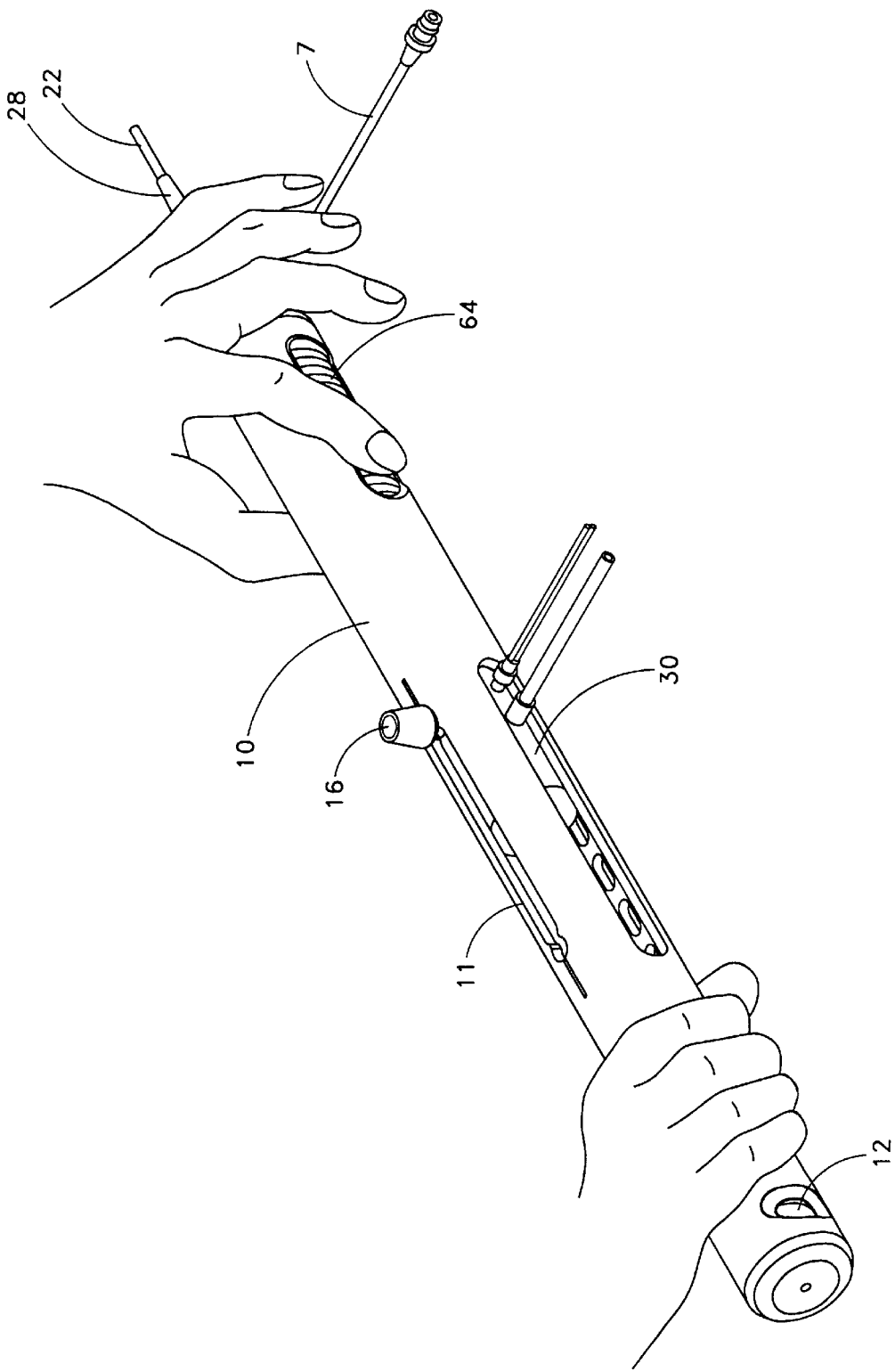
FIGS. 43–44 are perspective views illustrating the second step in the process of detaching the cartridge housing from the handle housing.
Figure 44:
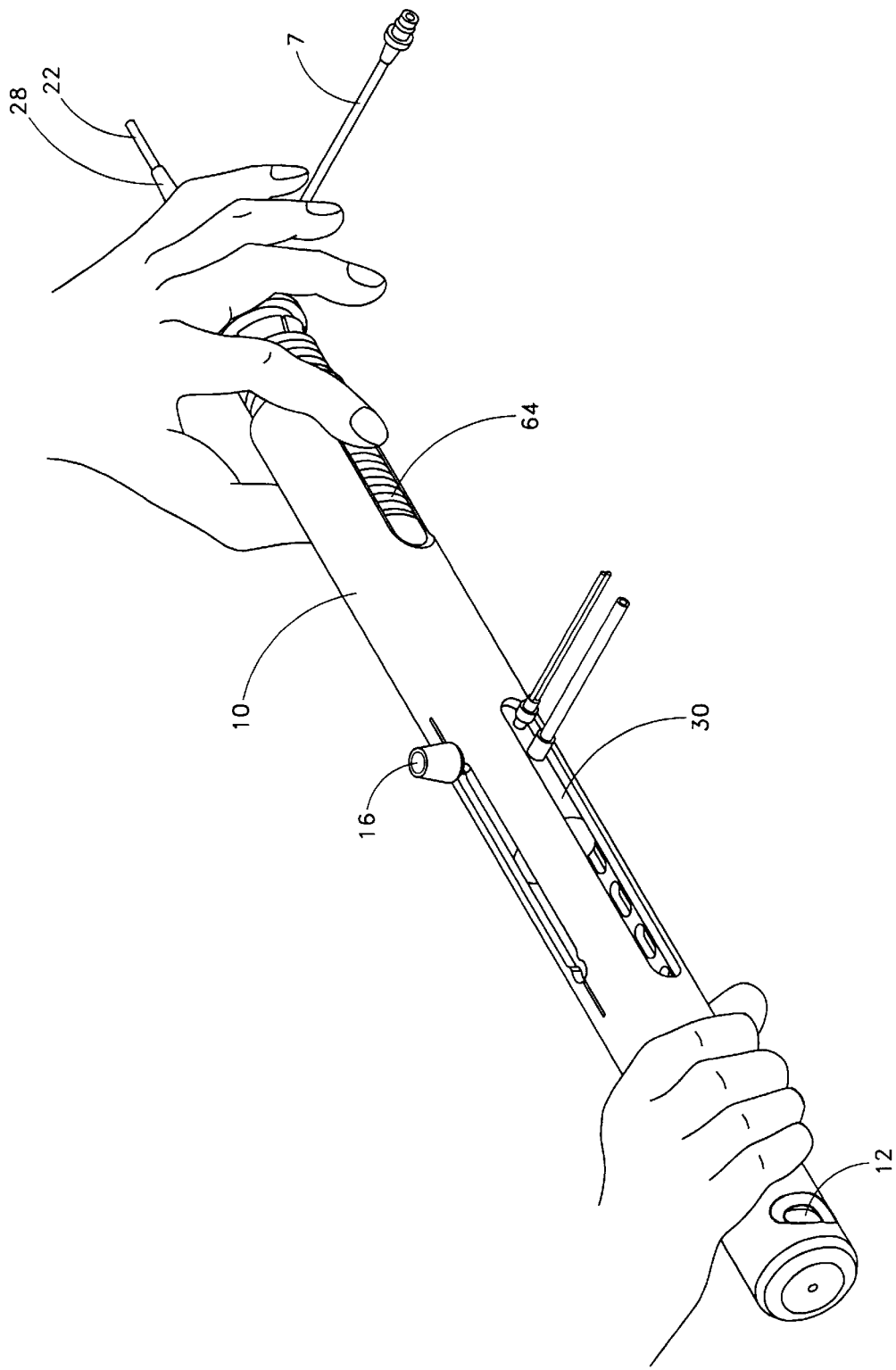
Figure 45:
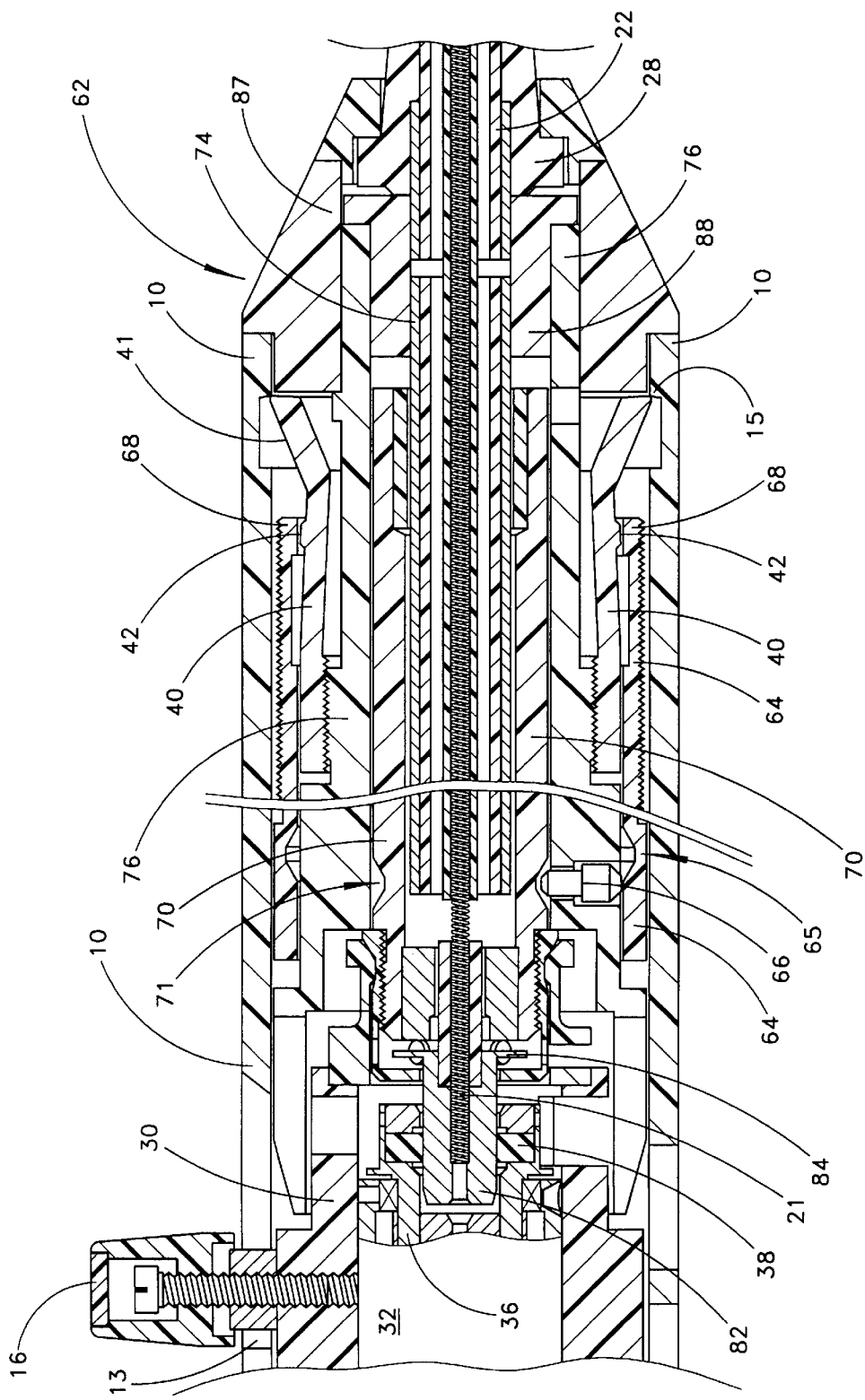
FIGS. 45–49 are longitudinal cross-sectional views illustrating the process of detaching the cartridge housing from the handle housing.
Figure 46:
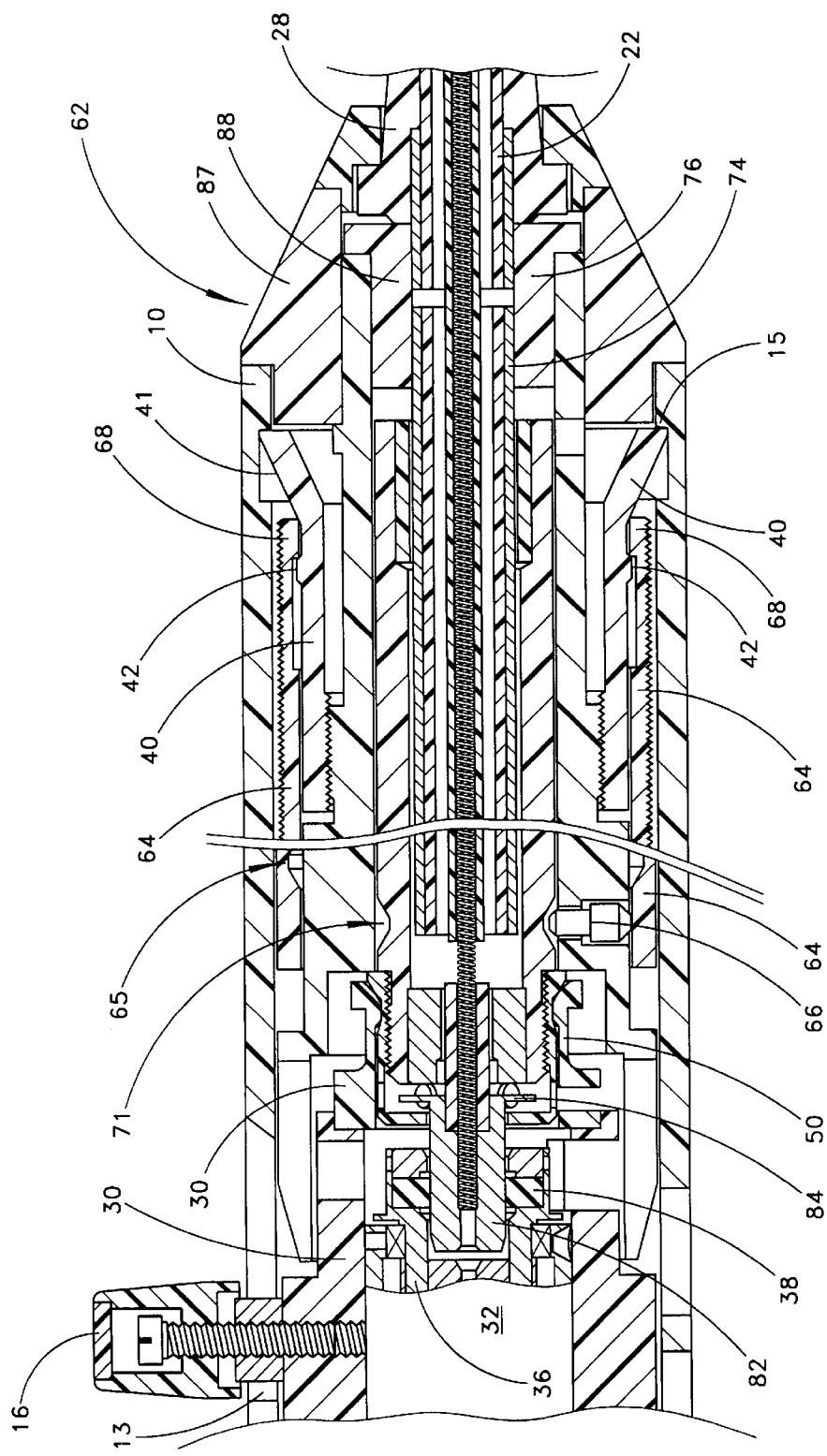

In FIG. 43 the user has grasped the slide 64 near the proximal end of the openings 19 in the handle housing 10 in order to move the slide distally. FIG. 44 illustrates that the user has moved the slide distally sufficiently to open the cartridge latch and to push the distal portion of the cartridge housing 62 out of the handle housing 10. FIG. 45 shows the slide 64 as it is being moved from its proximal working position toward the central neutral position. Notice that the catch 42 (carried by the resilient finger 40) and the catch-engaging element 68 of the slide 64 are sized and positioned so that the slide 64 may be moved from its working position to its neutral position (and vice versa) without unlocking the cartridge latch, even though such movement causes radially inward movement of the resilient fingers 40. In FIG. 46 the slide 64 has reached its neutral position, but the cartridge latch is still locking the cartridge housing 62 to the handle housing 10.

Figure 47:
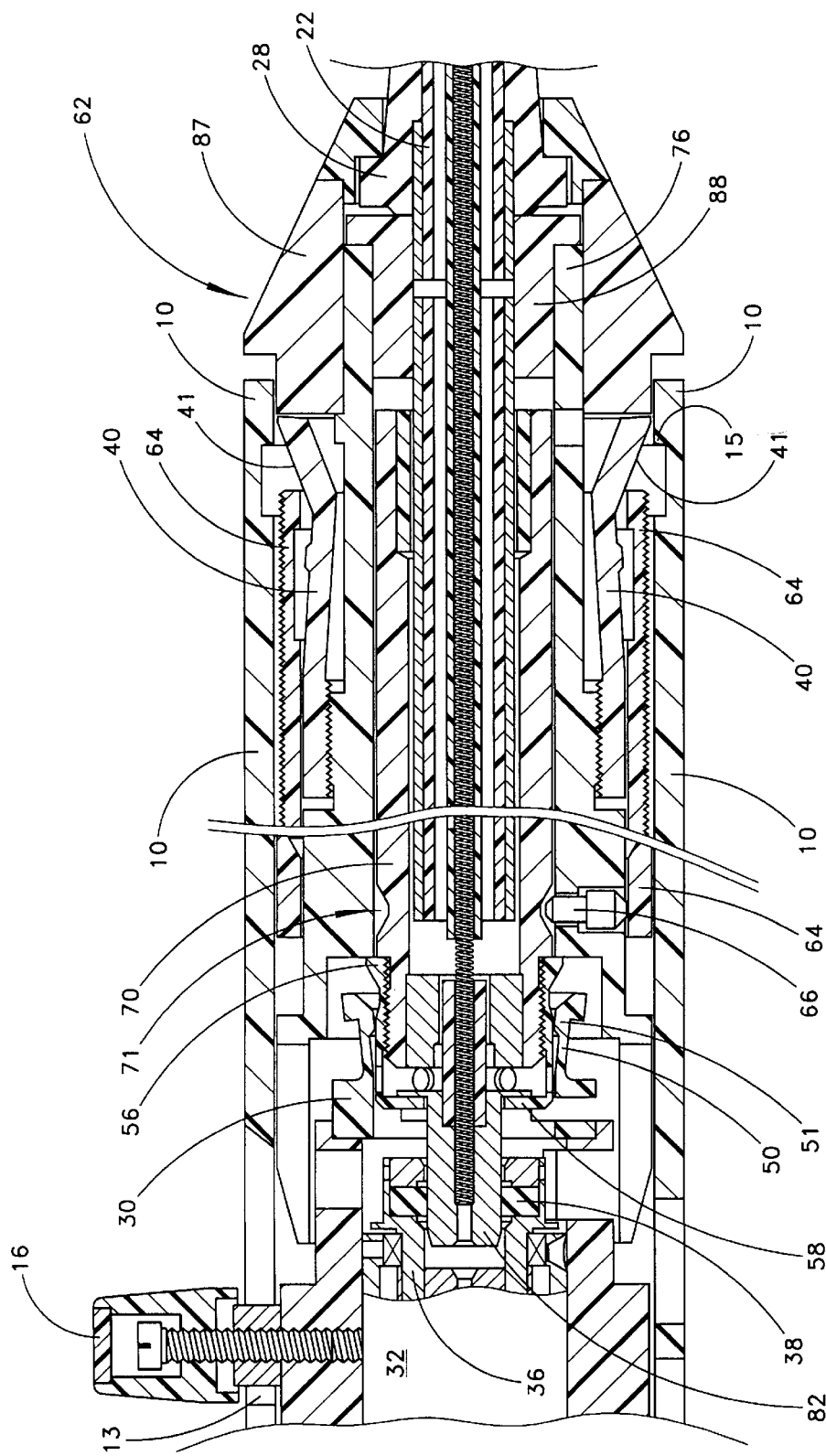

In FIG. 47, the distal movement of the slide 64 has continued to the point that the distal end of the slide 64, which functions as an abutment surface, has engaged the slanted outer surfaces 41 of the radially resilient fingers 40 to move the fingers 40 radially inwardly, thereby disengaging the fingers 40 from the shoulder 15 of the handle housing 10, thus permitting the cartridge housing 62 to be removed from the handle housing 10. Although the drawings illustrate the abutment surface as being the distal end of the slide 64, it need not necessarily be the distal end and could be any suitable surface associated with the slide 64. Note that the distal pressure exerted by the user on the slide 64 is conveyed by the slide to the fingers 40 and the cartridge housing 62, so that as soon as the fingers 40 are released from the shoulder 15 the entire exchangeable drive shaft cartridge 60 begins to move distally out of the handle housing 10, as is shown in FIGS. 47–48.

Figure 48:
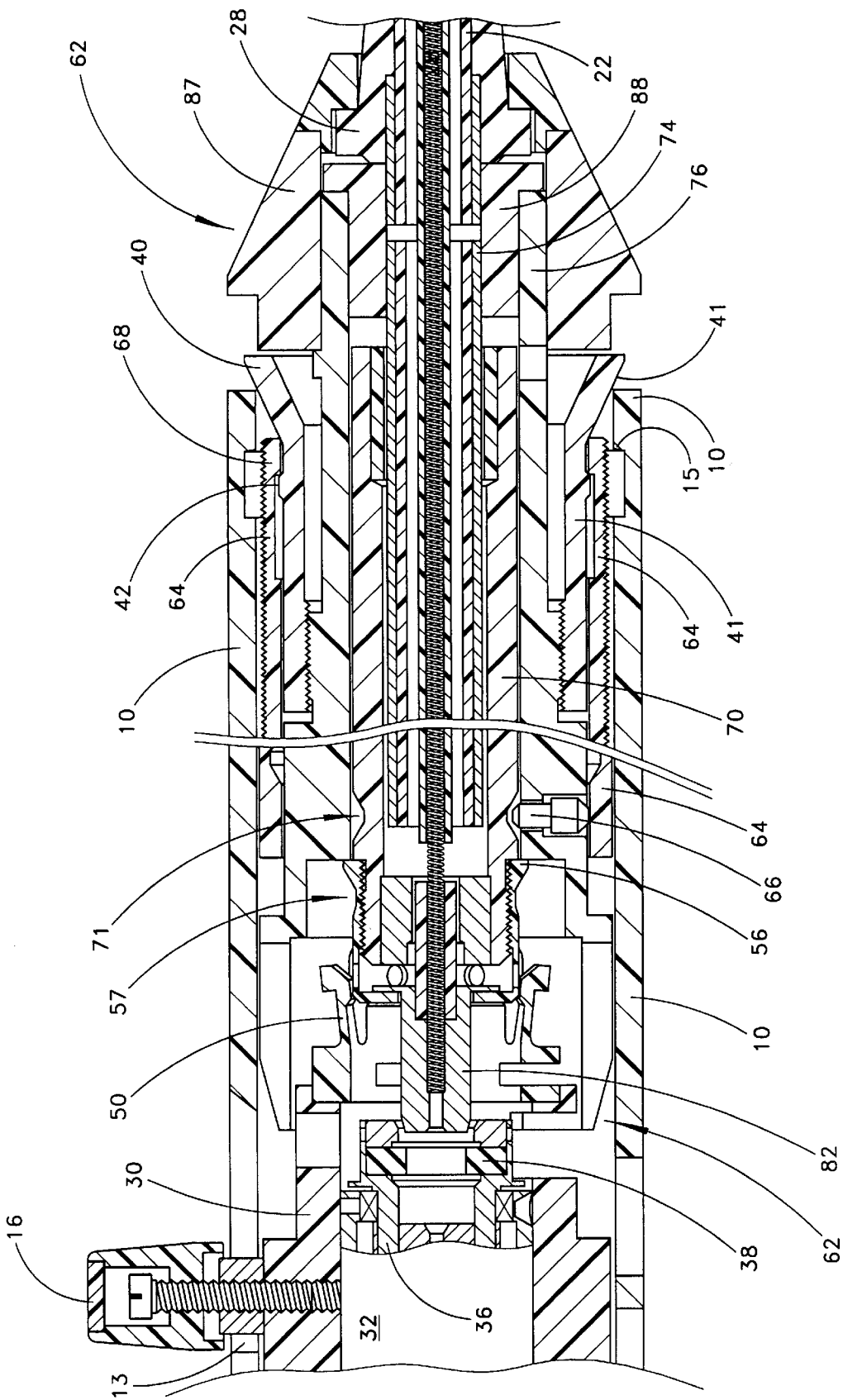
Figure 49:
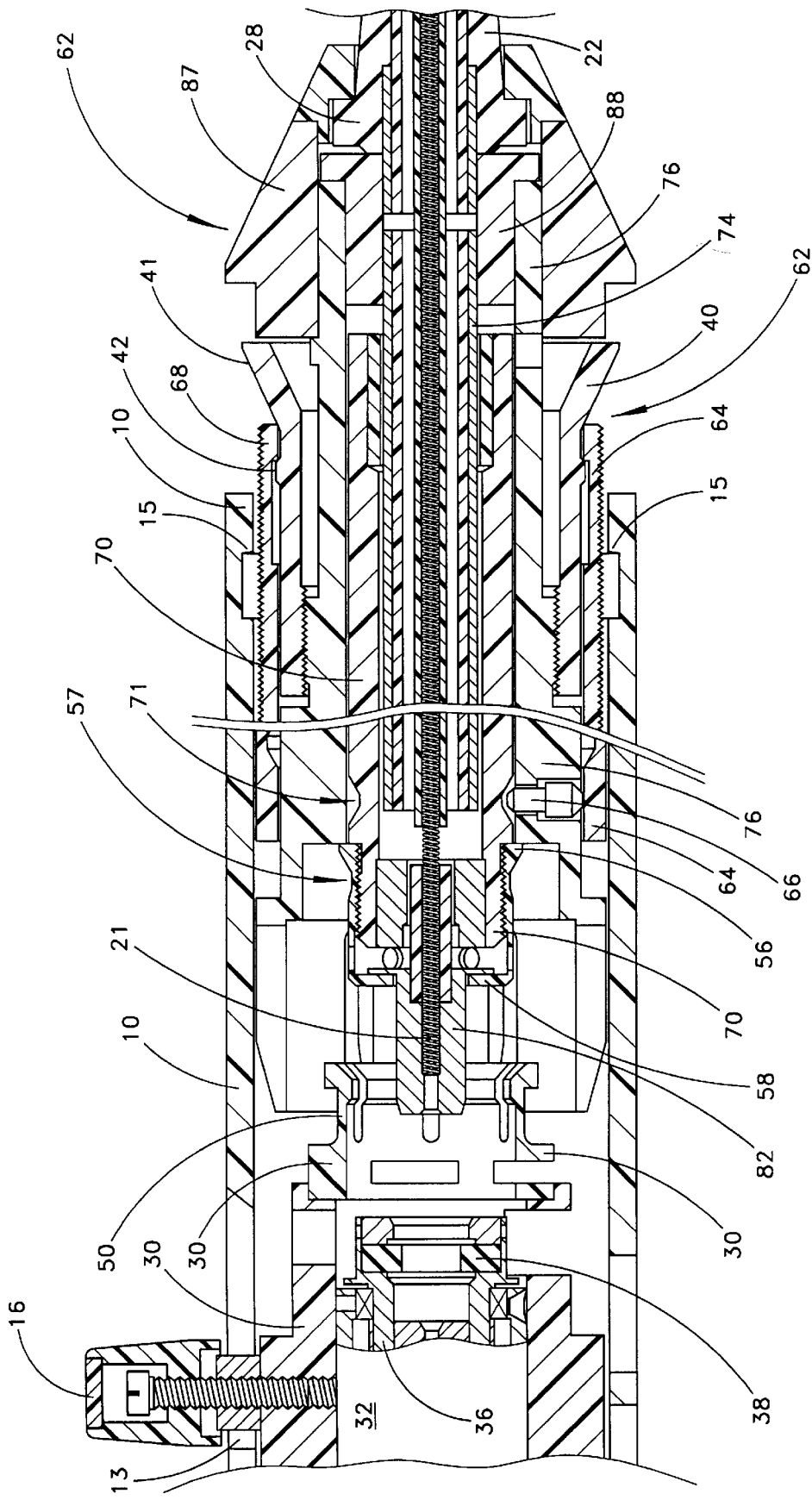

Desirably the openings 19 are sufficiently long (preferably at least about one inch) that the user, in a single movement, may move the slide 64 from its working position (FIG. 42) to a position where the cartridge housing 62 is at least partially moved out of the handle housing 10 (FIGS. 47–49). This single movement includes a first phase, where the slide 64 is moved distally with respect to the cartridge housing from its working position (FIG. 42) to its cartridge unlocked position (a position just before that depicted in FIG. 47), and a second phase where the slide 64, together with the cartridge housing 62, is moved distally with respect to the handle housing 10 (FIGS. 47–49). For easy gripping of the slide 64, its outer surface may have circumferential ribs or threads, as is shown in the drawings, or any other suitable grip-enhancing surface.

Figure 50:
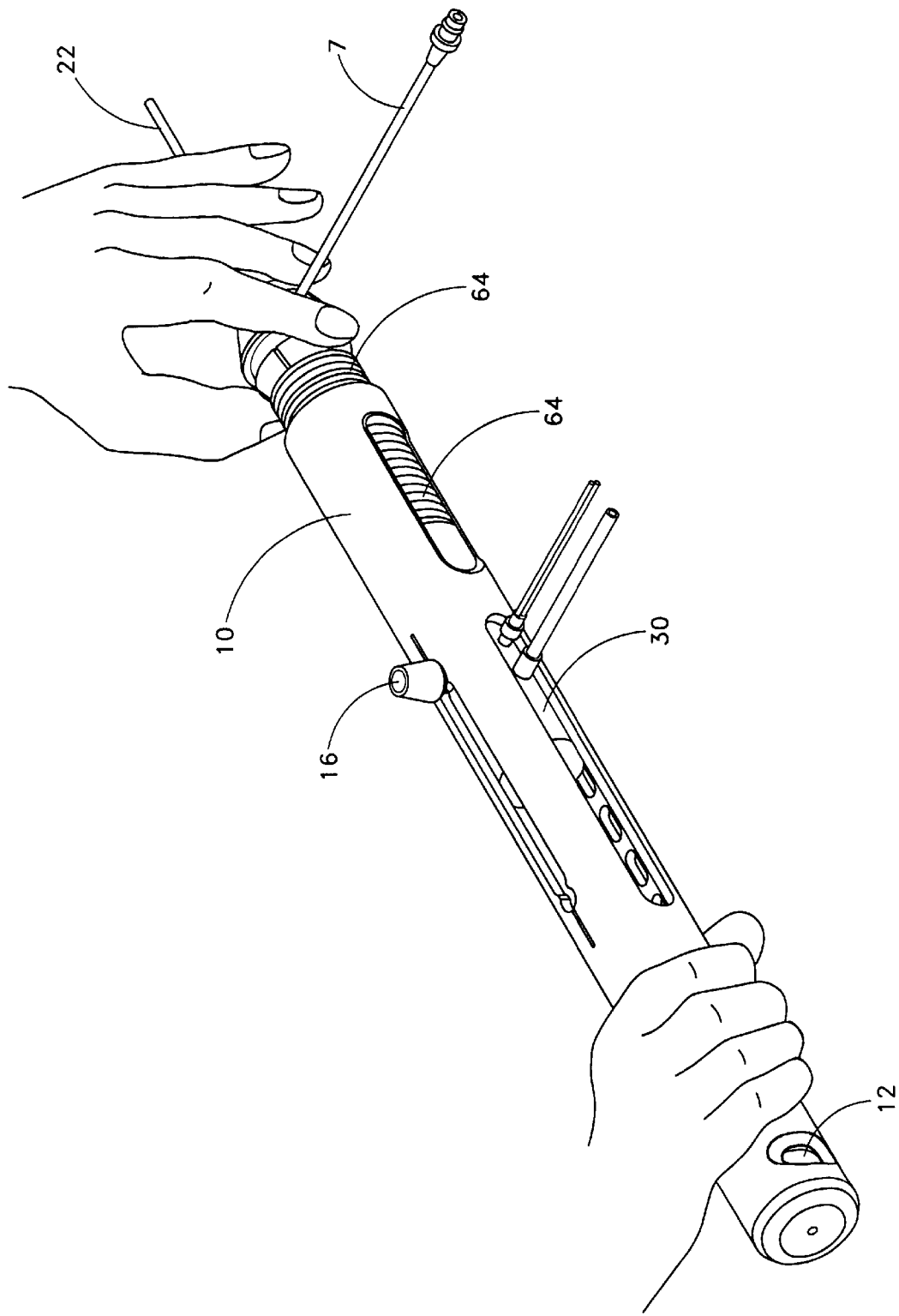
FIG. 50 is a perspective view illustrating the final step in detaching the cartridge housing from the handle housing.
Figure 51:
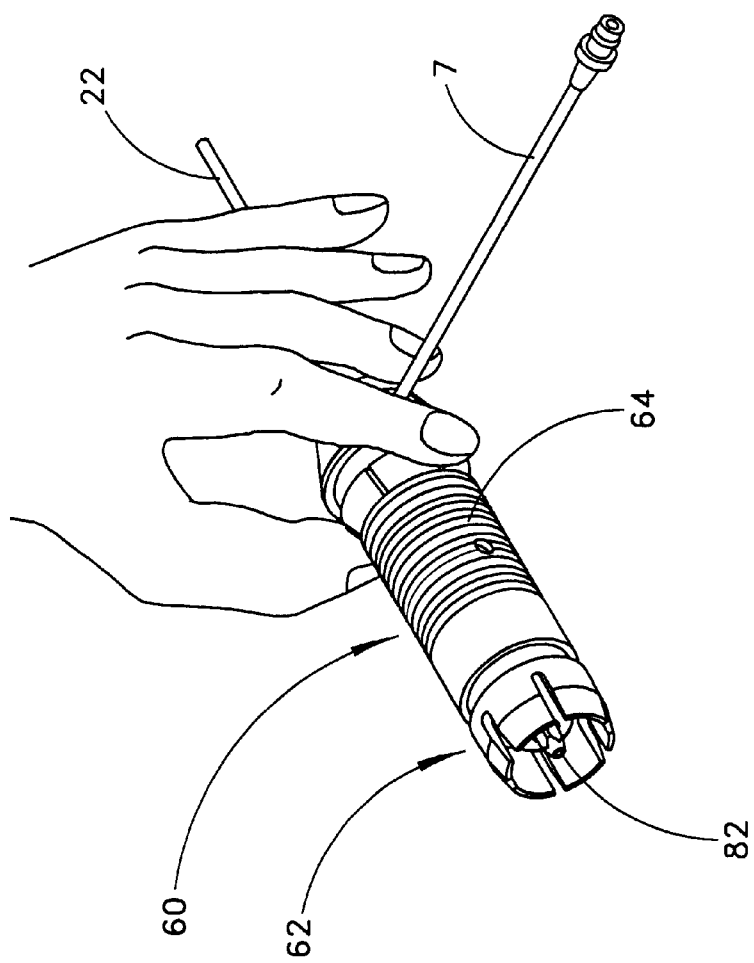
FIG. 51 is a perspective view of an exchangeable drive shaft cartridge after it has been detached from a handle housing.
Figure 52:
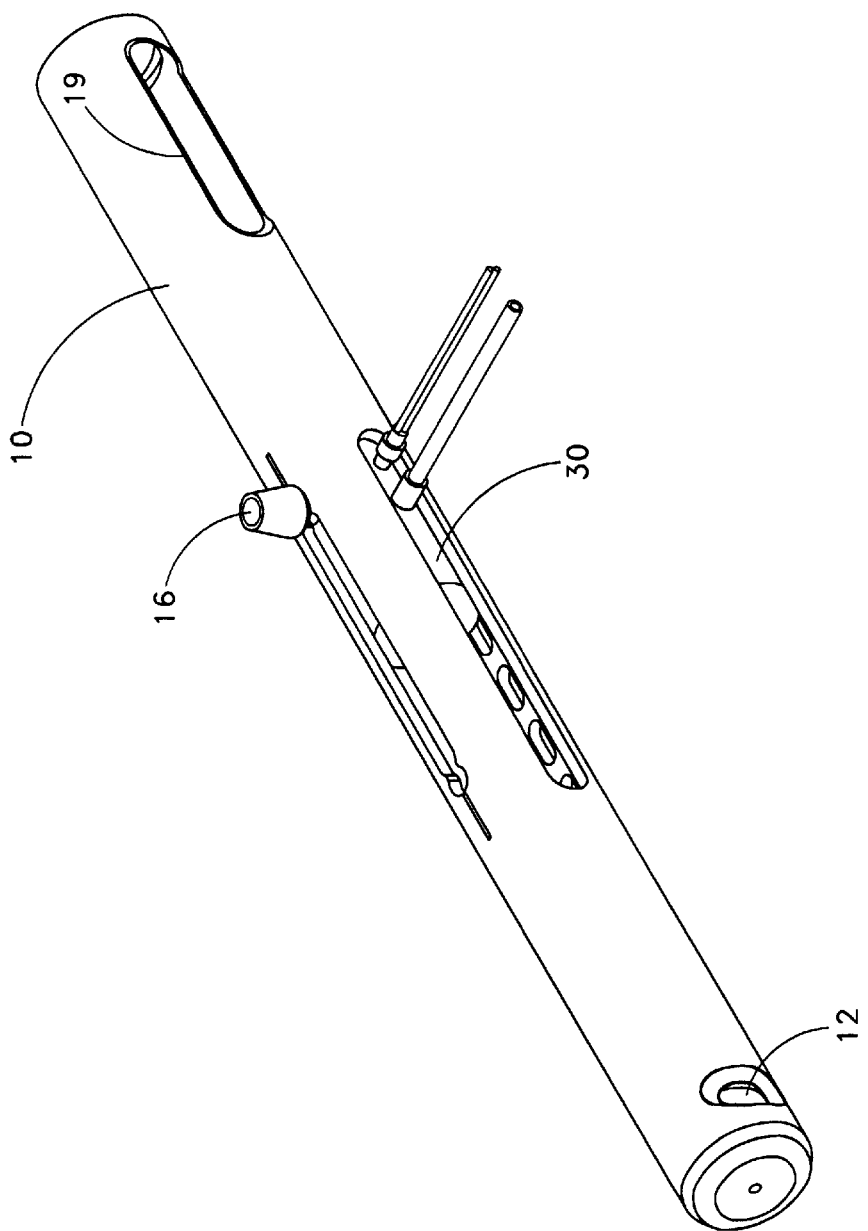
FIG. 52 is a perspective view of a handle housing after an exchangeable drive shaft cartridge has been detached from it.
Figure 53:
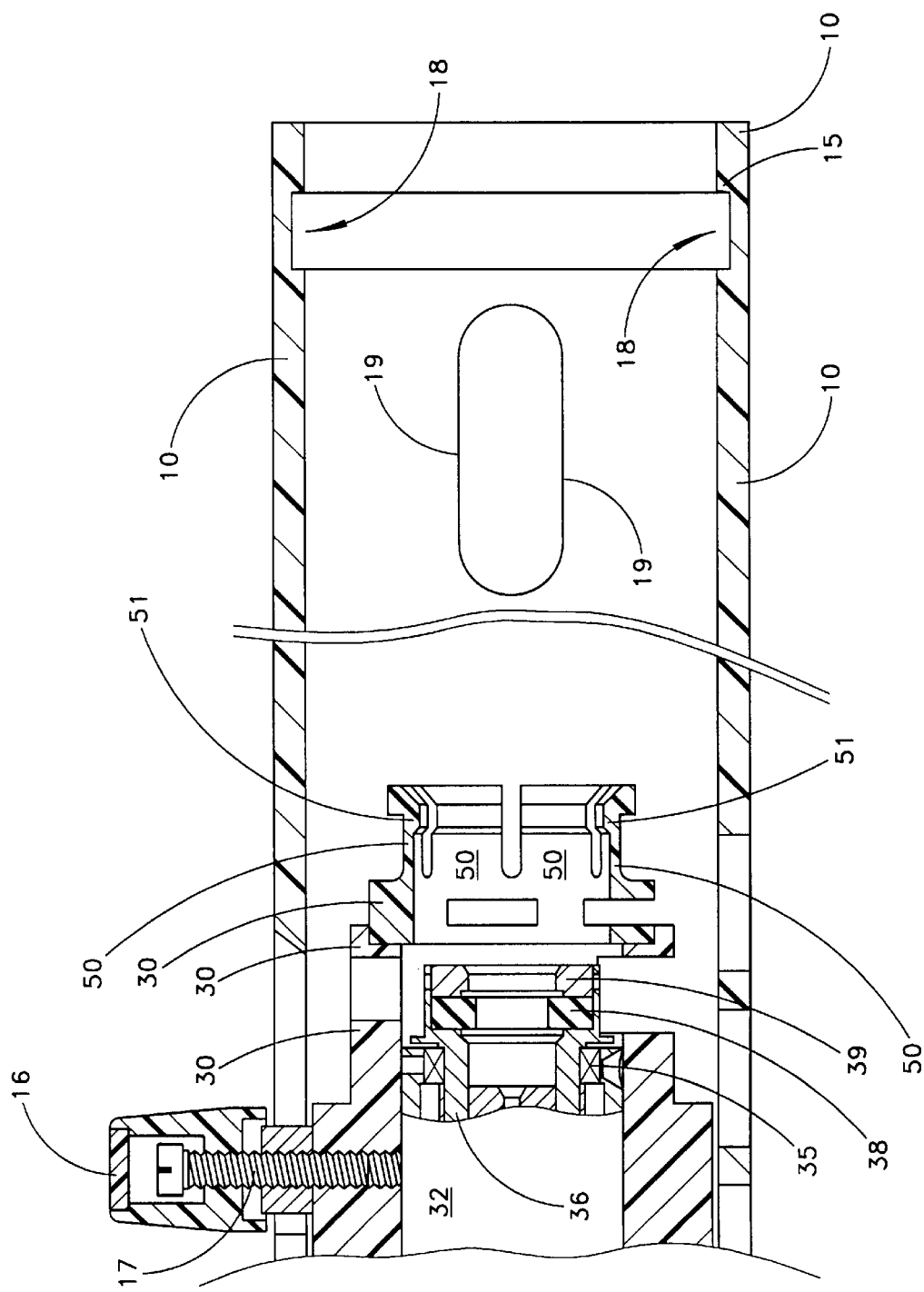
FIG. 53 is a broken-away longitudinal cross-sectional view of the distal portion of the handle housing.

In FIG. 50 the user is completing the process of removing the drive shaft cartridge 60 from the handle housing 10 by grasping that portion of the cartridge housing 62 that extends from the distal end of the handle housing 10. The removed exchangeable drive shaft cartridge 60 is shown in FIG. 51, and the handle housing 10, without the cartridge, is depicted in FIGS. 52–53.

Figure 54:
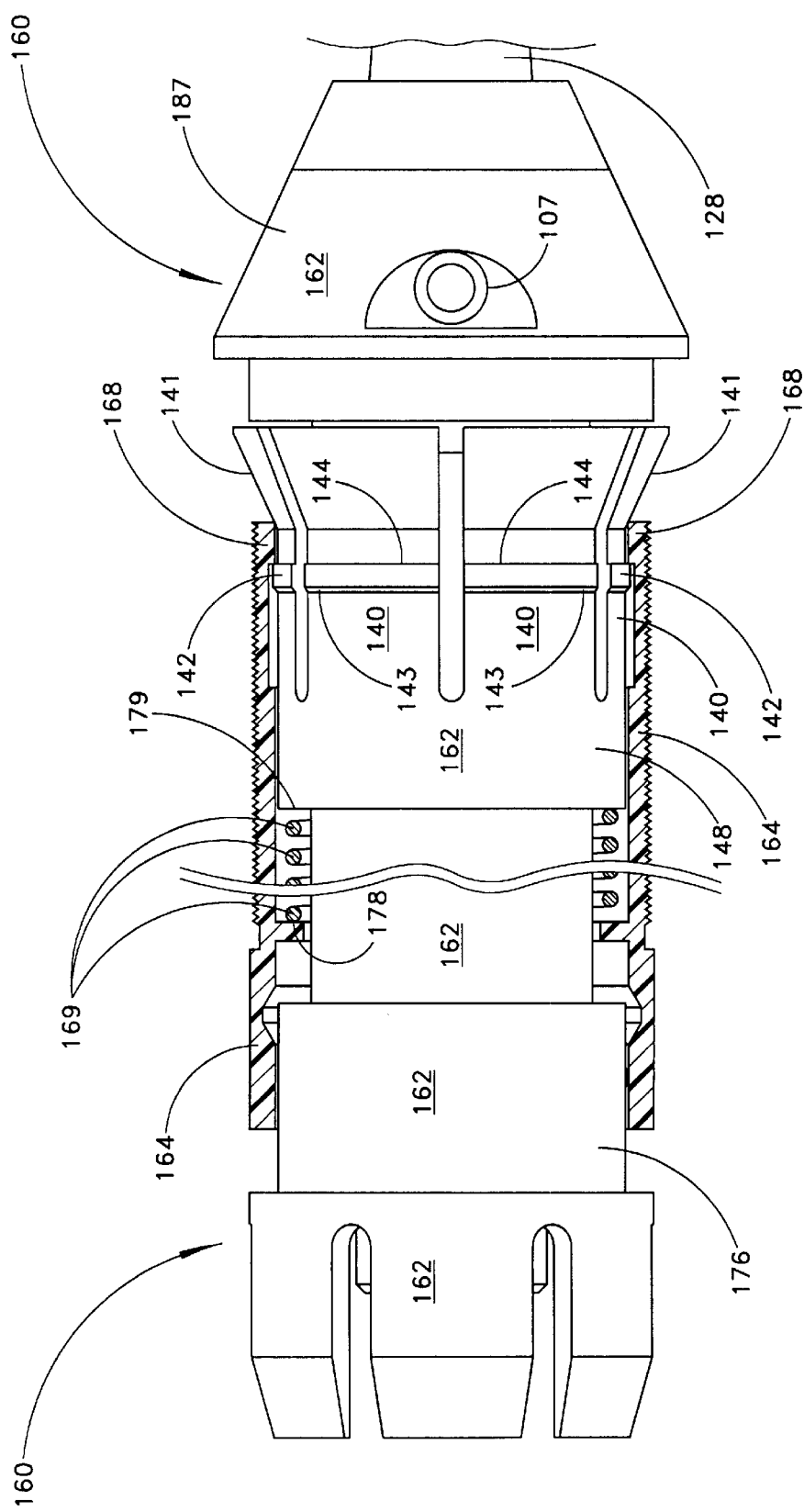
FIG. 54 is a partially broken away view of an alternate embodiment of an exchangeable drive shaft cartridge having a slide biasing spring.

FIG. 54 depicts, in partial cross-section, a particularly preferred embodiment of an exchangeable drive shaft cartridge 160 of the invention, and FIGS. 55–60 depict the process of attaching this cartridge 160 to a handle housing 10. (Elements of the particularly preferred exchangeable drive shaft cartridge 160 generally have reference numbers 100 higher than corresponding elements of the exchangeable drive shaft cartridge depicted in FIGS. 1–51.) The primary difference in the preferred drive shaft cartridge 160 of FIGS. 54–60 is the presence of a spring 169 biasing the slide 164 toward its working position. Preferably the spring 169 is a coil spring compressed between opposing spring abutting surfaces 178 and 179 of the slide 164 and the cartridge housing 162, respectively. The catches 142 on the fingers 142 and the catch-engaging element 168 of the slide 164 have complementary engagement surfaces which are generally perpendicular to a longitudinal axis of the cartridge housing 162 so as to restrict proximal movement of the slide 164 from its neutral position (depicted in FIG. 54) to its working position. That is, unlike the embodiment of FIGS. 1–51, one cannot simply grasp the slide 164 and move it from the neutral position proximally to the working position. The complementary engagement surfaces of the catches 142 and the catch-engaging element 168 are sized and positioned so that they become disengaged when the radially resilient fingers 140 are deflected radially inwardly, thereby allowing the spring 169 to move the slide 164 from its neutral position to its working position.

Figure 55:
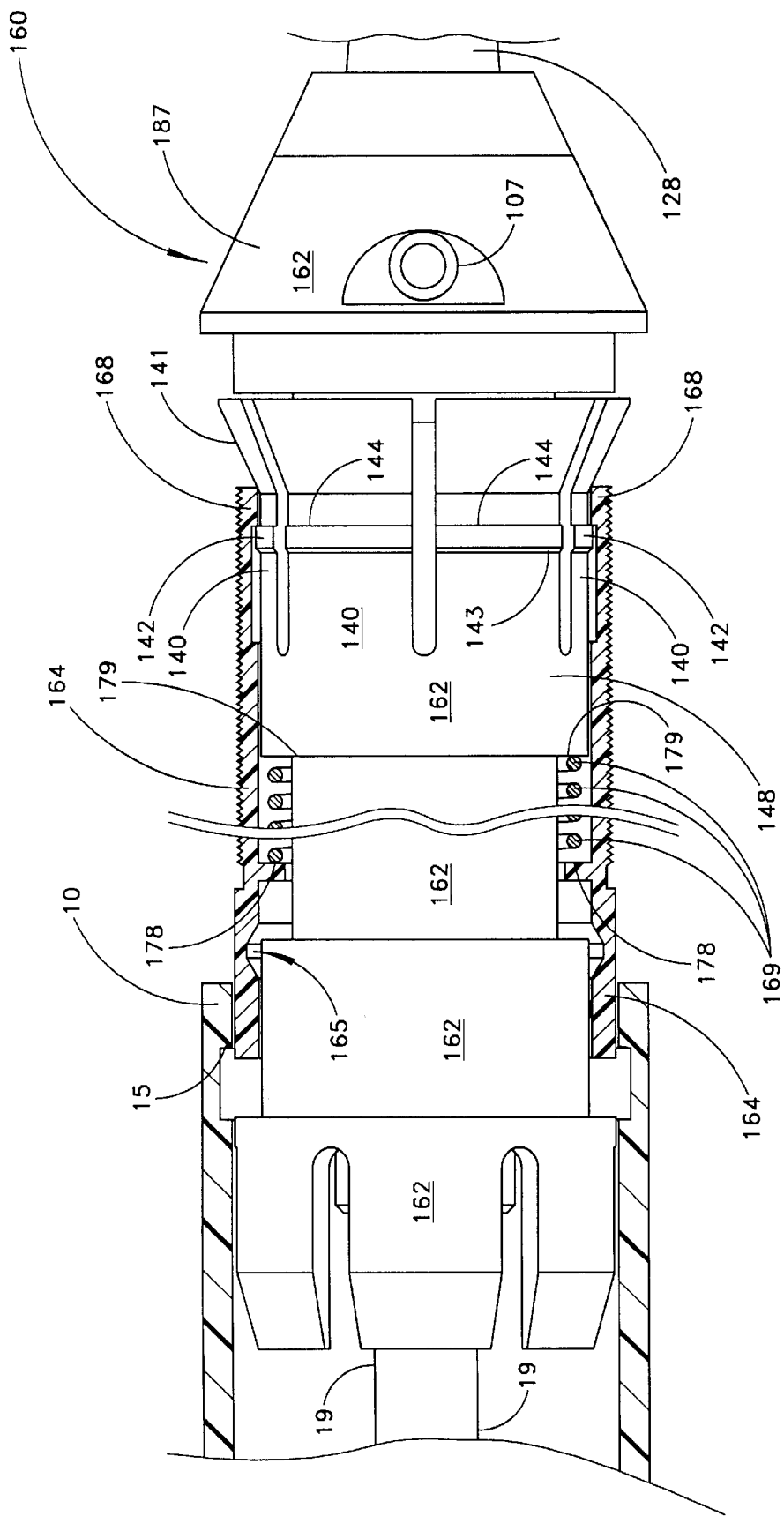
FIGS. 55–59 are partially broken away views showing the process of insertion of the cartridge housing into the handle housing and illustrating how the slide biasing spring automatically moves the slide from its neutral position (FIGS. 55–56) to its working position (FIGS. 58–59)
Figure 56:
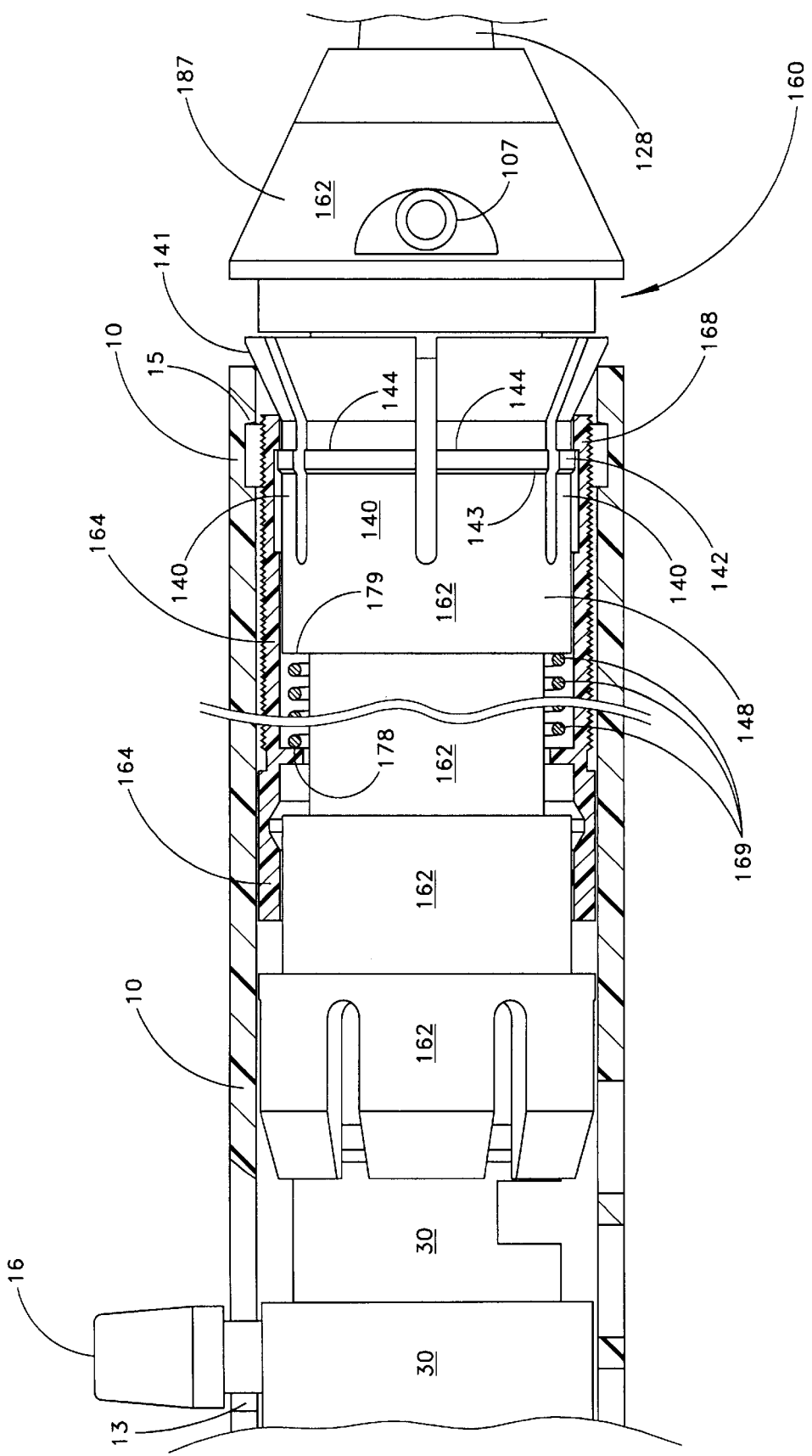
Figure 57:
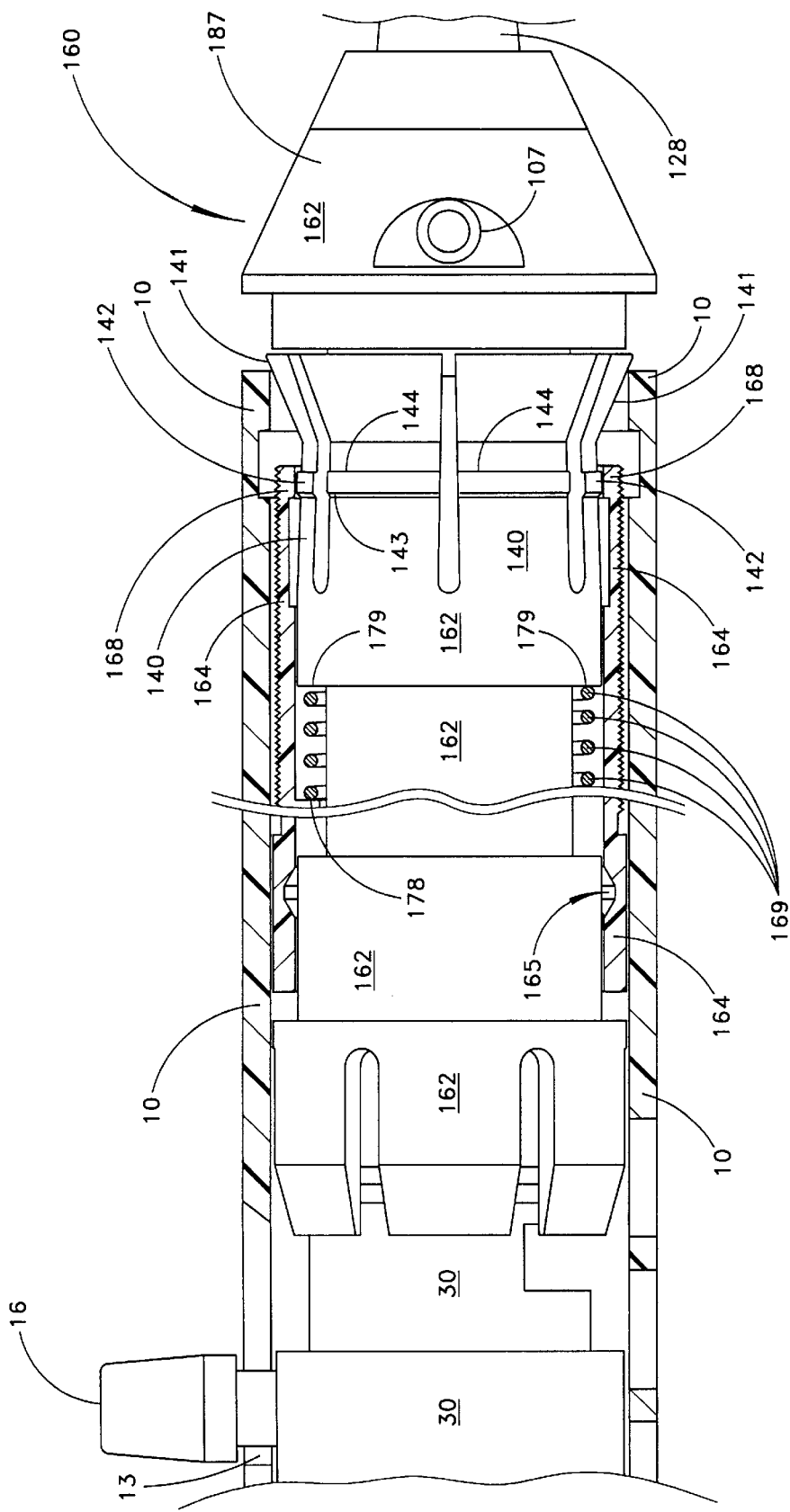

In FIG. 55 the drive shaft cartridge 160 is being inserted into the distal end of the handle housing 10. In FIG. 56 the drive shaft cartridge 160 has been inserted sufficiently that the radially resilient fingers 140 have just contacted the distal end of the handle housing 10. In FIG. 57 the drive shaft cartridge 160 has been inserted a little bit further and the radially resilient fingers 140 have begun to deflect radially inwardly. In this drawing one can see that the catches 142 and the slide's catch-engaging element 168 are sized and positioned so that insertion of the cartridge housing into the handle housing 10 causes the radially resilient fingers 140, together with their catches 142, to move radially inwardly a distance sufficient to release the catch-engaging element 168 of the slide 164 from the catches 142, thereby allowing the spring 169 to automatically move the slide 164 from its neutral position to its working position without requiring the user to do so manually. FIG. 57 thus is actually a "stop-motion" drawing illustrating the slide 164 in a position between the slide's neutral position and the slide's working position as the spring 169 is moving the slide 164 to its working position.

Figure 58:
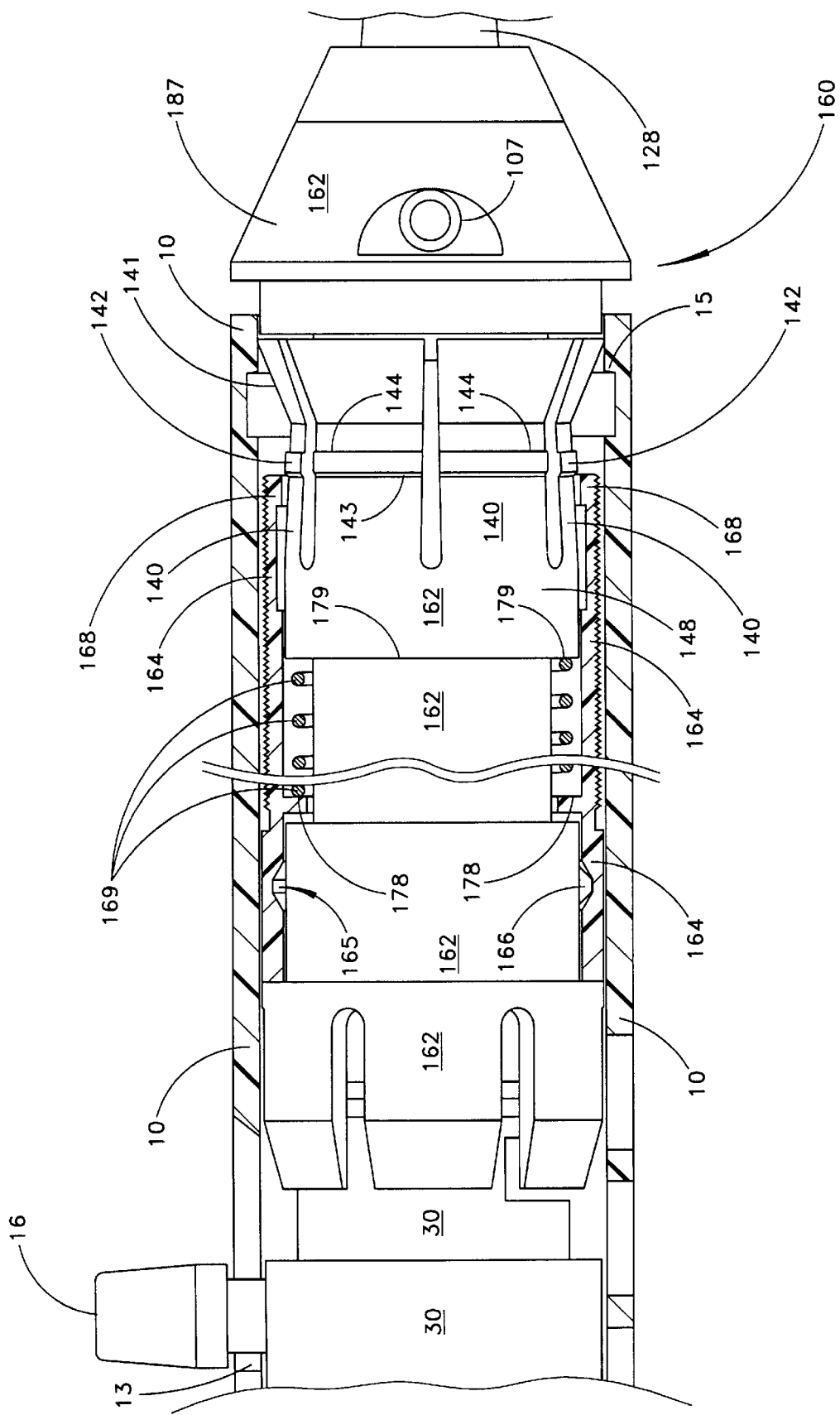
Figure 59:
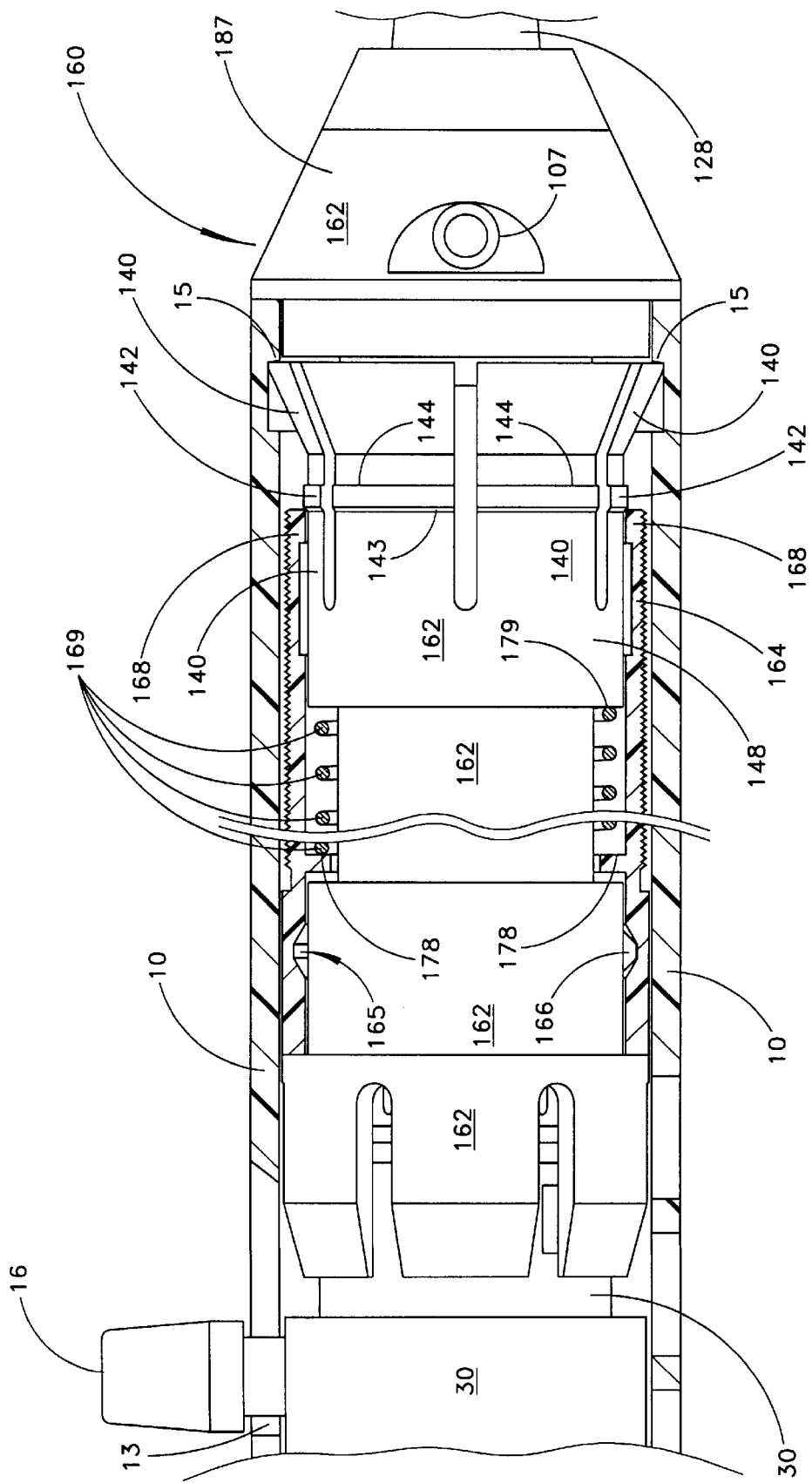
Figure 60:
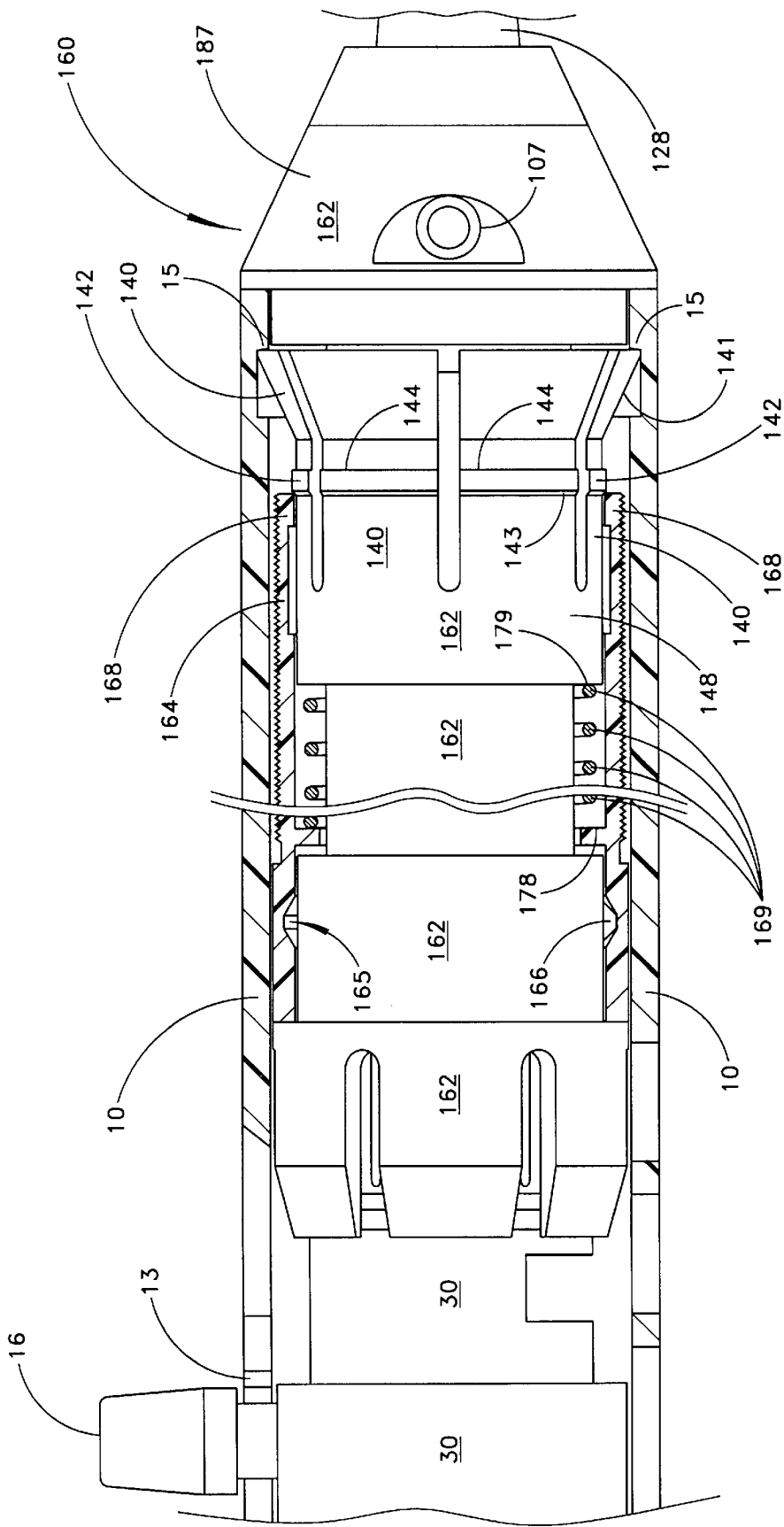
FIG. 60 is a partially broken away view similar to FIGS. 55–59 showing the prime mover carriage and the longitudinally movable tube moved proximally to their range of working positions.
Figure 61:
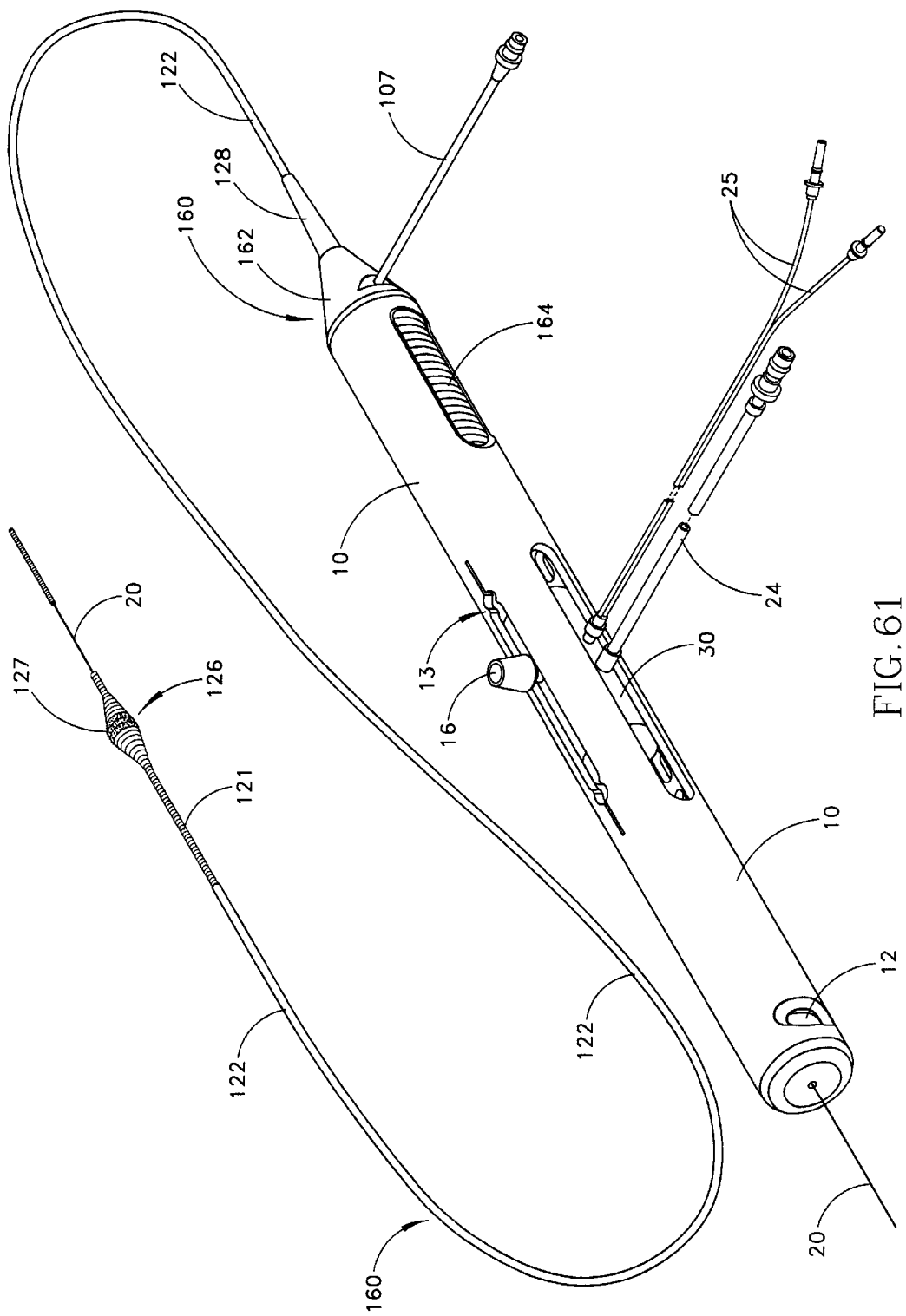
FIG. 61 is a perspective view similar to FIG. 1 illustrating an atherectomy device of the invention with an exchangeable drive shaft cartridge having a larger size tissue removal implement.

In FIG. 58 the slide 164 has reached its working position while the user continues to insert the drive shaft cartridge 160 into the handle housing 10. In FIG. 59 the drive shaft cartridge has been fully inserted into the handle housing 10, and in FIG. 60 the user has moved the control knob 16 (together with the prime mover carriage 130 and the longitudinally movable tube 170) proximally to the range of working positions. FIG. 61 shows the complete, assembled rotational atherectomy device, with the exchangeable drive shaft cartridge 160 having a tissue removal implement 126 different from (larger than) the tissue removal implement 26 shown in FIG. 1.

While a preferred embodiment of the present invention has been described, it should be understood that various changes, adaptations and modifications may be made therein without departing from the spirit of the invention and the scope of the appended claims.

What is claimed is:

1. A rotational atherectomy device comprising:
    a handle housing;
    a rotatable prime mover carried by a prime mover carriage which is disposed within the handle housing, the prime mover carriage being longitudinally movable with respect to the handle housing;
    an exchangeable drive shaft cartridge including:
        a cartridge housing which is removably attachable to the handle housing;
        a longitudinally movable tube disposed within the cartridge housing and having a proximal end portion which is removably attachable to the prime mover carriage for longitudinal movement therewith; and
        a rotatable flexible drive shaft having a proximal portion which is disposed within the longitudinally movable tube and a distal portion which includes a tissue removal implement; and
    a drive shaft attachment mechanism removably attaching the proximal portion of the drive shaft to the prime mover;
    a cartridge latch removably locking the cartridge housing to the handle housing; and
    a slide which is longitudinally movable with respect to the cartridge housing from a neutral position, where the cartridge latch is locked, to a cartridge unlocked position where the slide unlocks the cartridge latch, thereby permitting the cartridge housing to be removed from the handle housing.

2. The rotational atherectomy device of claim 1 wherein the slide is generally tubular in shape.

3. The rotational atherectomy device of claim 2 wherein the tubular slide is disposed about the cartridge housing.

4. The rotational atherectomy device of claim 1 wherein the handle housing includes a pair of openings sized and positioned so that the slide may be grasped through the openings and moved longitudinally with respect to both the cartridge housing and the handle housing.

5. The rotational atherectomy device of claim 1 wherein the cartridge latch comprises at least one radially resilient finger which is carried by the cartridge housing and which is removably engageable with a complementary structure carried by the handle housing.

6. The rotational atherectomy device of claim 5 wherein the complementary structure comprises a radially inwardly extending shoulder.

7. The rotational atherectomy device of claim 6 wherein the shoulder is generally annular and is positioned near the distal end of the handle housing.

8. The rotational atherectomy device of claim 6 wherein the shoulder comprises a distal wall of a generally annular groove formed in a wall of the handle housing, the groove removably receiving therein a latching portion of the radially resilient finger.

9. The rotational atherectomy device of claim 5 wherein the cartridge latch includes two or more radially resilient fingers carried by the cartridge housing.

10. The rotational atherectomy device of claim 5 wherein the radially resilient finger has a portion with an outer surface slanting distally radially outwardly, the slide having an abutment surface positioned so that when the slide is moved distally with respect to the radially resilient finger the abutment surface of the slide engages the slanted outer surface of the radially resilient finger to move the finger radially inwardly, thereby disengaging the finger from the complementary structure of the handle housing and permitting the cartridge housing to be removed from the handle housing.

11. The rotational atherectomy device of claim 10 wherein the abutment surface comprises a distal end of the slide.

12. The atherectomy device of claim 1 further comprising a tube latch for selectively locking the longitudinally movable tube against longitudinal movement with respect to the cartridge housing.

13. The atherectomy device of claim 12 wherein the tube latch is capable of selectively locking the slide against longitudinal movement with respect to the cartridge housing.

14. The atherectomy device of claim 13 wherein the tube latch is configured and arranged so that whenever the tube is locked against longitudinal movement then the slide is longitudinally movable, and whenever the slide is locked against longitudinal movement then the tube is longitudinally movable.

15. The atherectomy device of claim 1 further comprising a tube latch positioned to selectively lock the longitudinally movable tube and the slide against longitudinal movement with respect to the cartridge housing.

16. The atherectomy device of claim 15 wherein the tube latch is configured and arranged so that whenever the tube is locked against longitudinal movement then the slide is longitudinally movable, and whenever the slide is locked against longitudinal movement then the tube is longitudinally movable.

17. The rotational atherectomy device of claim 16 wherein the tube latch includes a tube locking element carried by the cartridge housing, the tube locking element being radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

18. The rotational atherectomy device of claim 17 wherein the tube locking element is disposed within a radial bore in a wall of the cartridge housing.

19. The rotational atherectomy device of claim 17 wherein the tube latch includes a generally annular recess formed in an outer surface of the longitudinally movable tube, the recess receiving an inner portion of the tube locking element when the tube locking element is moved radially inwardly to its tube locked position.

20. The rotational atherectomy device of claim 17 wherein the tube latch includes a generally annular recess formed in an inner surface of the slide, the annular recess receiving an outer portion of the tube locking element when the tube locking element is moved radially outwardly to its tube unlocked position.

21. The rotational atherectomy device of claim 20 wherein the tube latch permits longitudinal movement of the slide when the annular recess of the longitudinally moveable tube is longitudinally aligned with the tube locking element carried by the cartridge housing.

22. The rotational atherectomy device of claim 1 further comprising at least one tube locking element carried by the cartridge housing and radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

23. The rotational atherectomy device of claim 22 wherein the tube locking element is disposed within a radial bore in a wall of the cartridge housing.

24. The rotational atherectomy device of claim 22 wherein the slide is generally tubular and includes an inner surface having a generally annular recess which receives an outer portion of the tube locking element when the tube locking element is moved radially outwardly to its tube unlocked position.

25. The rotational atherectomy device of claim 22 wherein an outer surface of the longitudinally movable tube has a generally annular recess which receives an inner portion of the tube locking element when the tube locking element is moved radially inwardly to its tube locked position.

26. The rotational atherectomy device of claim 22 wherein the slide is movable proximally from its neutral position, where the cartridge latch is locked and the tube locking element is in its tube locked position, to a working position where the cartridge latch remains locked while the tube locking element is movable to its tube unlocked position, thereby permitting the longitudinally moveable tube to be moved proximally out of its tube lockable position.

27. The atherectomy device of claim 26 wherein the slide is generally tubular and includes a generally annular recess in its inner surface, the annular recess in the slide being positioned so that movement of the slide to its working position longitudinally aligns the annular recess of the slide with the tube locking element, permitting the tube locking element to move radially outwardly to unlock the longitudinally movable tube.

28. The atherectomy device of claim 27 wherein an annular recess in the outer surface of the longitudinally movable tube is positioned so that whenever the tube is moved proximally out of its tube lockable position the tube locking element is moved radially outwardly so that an outer portion of the tube locking element is moved into the annular recess of the slide, the tube locking element being retained in such position by an outer surface of the longitudinally movable tube, thereby locking the slide in its working position.

29. The atherectomy device of claim 27 wherein the annular recess in the tubular slide is positioned so that whenever the slide is moved distally out of its working position the tube locking element is moved radially inwardly so that an inner portion of the tube locking element is moved into an annular recess in an outer surface of the longitudinally movable tube, the tube locking element being retained in such position by the inner surface of the slide, thereby locking the longitudinally movable tube against longitudinal movement with respect to the cartridge housing.

30. The rotational atherectomy device of claim 26 wherein the cartridge latch comprises at least one radially resilient finger which is carried by the cartridge housing and which is removably engageable with a complementary structure carried by the handle housing.

31. The rotational atherectomy device of claim 30 wherein the radially resilient finger carries a catch positioned to engage a catch-engaging element of the slide, the catch restricting free movement of the slide between the neutral position and the working position.

32. The rotational atherectomy device of claim 31 wherein the catch includes proximal and distal engagement surfaces, the distal engagement surface being slanted proximally radially outwardly so that movement of the slide proximally from its neutral position causes the catch-engaging element to engage the distal engagement surface of the catch to move the catch, together with the radially resilient finger, radially inwardly a distance sufficient to release the catch-engaging element of the slide from the catch, thereby permitting the slide to be manually moved from its neutral position to its working position.

33. The rotational atherectomy device of claim 31 wherein the catch includes proximal and distal engagement surfaces, the proximal engagement surface being slanted distally radially outwardly so that movement of the slide distally from its working position causes the catch-engaging element to engage the proximal engagement surface of the catch to move the catch, together with the radially resilient finger, radially inwardly a distance sufficient to release the catch-engaging element of the slide from the catch, thereby permitting the slide to be manually moved distally out of its working position to and beyond its neutral position.

34. The rotational atherectomy device of claim 31, 32, or 33 wherein the catch of the finger and the catch engaging element of the slide are sized and positioned so that the slide may be moved between its neutral and working positions without unlocking the cartridge latch.

35. The rotational atherectomy device of claim 31 wherein at least one of the catch and the catch-engaging element has an engagement surface which is slanted proximally radially outwardly so that movement of the slide proximally from its neutral position forces the catch, together with the radially resilient finger, to move radially inwardly a distance sufficient to release the catch-engaging element of the slide from the catch, thereby permitting the slide to be manually moved from its neutral position to its working position.

36. The rotational atherectomy device of claim 31 wherein at least one of the catch and the catch-engaging element has an engagement surface which is slanted distally radially outwardly so that movement of the slide distally from its working position forces the catch, together with the radially resilient finger, to move radially inwardly a distance sufficient to release the catch-engaging element of the slide from the catch, thereby permitting the slide to be manually moved distally out of its working position to and beyond its neutral position.

37. The rotational atherectomy device of claim 31 further comprising a spring biasing the slide toward its working position, the catch and the catch-engaging element having complementary engagement surfaces which are generally perpendicular to a longitudinal axis of the cartridge housing and which restrict proximal movement of the slide from its neutral position to its working position.

38. The rotational atherectomy device of claim 37 wherein the complementary engagement surfaces are sized and positioned so that they become disengaged when the radially resilient finger is deflected radially inwardly, thereby allowing the spring to move the slide from its neutral position to its working position.

39. The rotational atherectomy device of claim 31 further comprising a spring biasing the slide toward its working position, the catch and the catch-engaging element being sized and positioned so that insertion of the cartridge housing into the handle housing causes the radially resilient finger, together with the catch, to move radially inwardly a distance sufficient to release the catch-engaging element of the slide from the catch, thereby allowing the spring to move the slide from its neutral position to its working position.

40. The rotational atherectomy device of claim 39 wherein the slide biasing spring comprises a coil spring disposed about the cartridge housing.

41. The rotational atherectomy device of claim 39 wherein the slide biasing spring is compressed between opposing spring abutting surfaces of the slide and the cartridge housing.

42. The rotational atherectomy device of claim 26 wherein the handle housing includes a pair of openings sized and positioned so that the slide may be grasped through the openings by a user when the cartridge housing is attached to the handle housing.

43. The rotational atherectomy device of claim 42 wherein the openings are sufficiently long to permit manual movement of the slide between the neutral and working positions when the cartridge housing is attached to the handle housing.

44. The rotational atherectomy device of claim 42 wherein the openings are sufficiently long that a user, by a single movement, may move the slide from the slide's working position to a position where the cartridge housing is at least partially moved out of the handle housing, the single movement including a first phase, where the slide is moved from its working position to its cartridge unlocked position, and a second phase where the slide, together with the cartridge housing, is moved distally with respect to the handle housing.

45. The rotational atherectomy device of claim 42 wherein the openings have a longitudinal length of at least about one inch.

46. A rotational atherectomy device comprising:
a handle housing;
a rotatable prime mover carried by a prime mover carriage which is disposed within the handle housing, the prime mover carriage being longitudinally movable with respect to the handle housing;
an exchangeable drive shaft cartridge including:
a cartridge housing which is removably attachable to the handle housing;
a longitudinally movable tube disposed within the cartridge housing and having a proximal end portion which is removably attachable to the prime mover carriage for longitudinal movement therewith;
a tube latch which selectively locks the longitudinally moveable tube against longitudinal movement with respect to the cartridge housing; and
a rotatable flexible drive shaft having a proximal portion which is disposed within the longitudinally movable tube and a distal portion which includes a tissue removal implement; and
a drive shaft attachment mechanism removably attaching the proximal portion of the drive shaft to the prime mover.

47. The rotational atherectomy device of claim 46 further comprising a slide which is longitudinally moveable with respect to the cartridge housing from a neutral position where the slide causes the tube latch to lock the longitudinally movable tube, to a working position, where the slide causes the tube latch to unlock the tube, thereby permitting its longitudinal movement with respect to the cartridge housing.

48. The atherectomy device of claim 47 wherein the tube latch is capable of selectively locking the slide against longitudinal movement with respect to the cartridge housing.

49. The atherectomy device of claim 48 wherein the tube latch is configured and arranged so that whenever the tube is locked against longitudinal movement then the slide is longitudinally movable, and whenever the slide is locked against longitudinal movement then the tube is longitudinally movable.

50. The rotational atherectomy device of claim 49 wherein the tube latch includes a tube locking element which is radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

51. The rotational atherectomy device of claim 50 wherein the tube latch includes three or more tube locking elements circumferentially spaced away from each other.

52. The rotational atherectomy device of claim 50 wherein the tube locking element is disposed within a radial bore in a wall of the cartridge housing.

53. The rotational atherectomy device of claim 50 wherein the tube locking element comprises a radially movable locking pin.

54. The rotational atherectomy device of claim 50 wherein the tube locking element comprises a radially movable locking ball.

55. The rotational atherectomy device of claim 50 wherein the tube latch includes a generally annular recess formed in an outer surface of the longitudinally movable tube, the recess receiving an inner portion of the tube locking element when the tube locking element is moved radially inwardly to its tube locked position.

56. The rotational atherectomy device of claim 55 wherein the tube latch includes a generally annular recess formed in an inner surface of the slide, the annular recess receiving an outer portion of the tube locking element when the tube locking element is moved radially outwardly to its tube unlocked position.

57. The rotational atherectomy device of claim 56 wherein the tube latch permits longitudinal movement of the slide when the annular recess of the longitudinally moveable tube is longitudinally aligned with the tube locking element disposed within a radial bore in a wall of the cartridge housing.

58. The atherectomy device of claim 46 further comprising a cartridge latch removably locking the cartridge housing to the handle housing.

59. The rotational atherectomy device of claim 58 wherein the drive shaft cartridge includes a slide which is longitudinally moveable with respect to the cartridge housing among at least three positions, a working position where the slide causes the tube latch to unlock the longitudinally movable tube, a neutral position where the slide causes the tube latch to lock the tube against longitudinal movement with respect to the cartridge housing, and a cartridge unlocked position where the slide causes the tube latch to maintain the longitudinally movable tube in its locked position and unlocks the cartridge latch, thereby permitting the cartridge housing to be removed from the handle housing.

60. The rotational atherectomy device of claim 59 wherein the cartridge latch comprises at least one radially resilient finger which is carried by the cartridge housing and which is removably engageable with a complementary structure carried by the handle housing.

61. The rotational atherectomy device of claim 60 wherein the radially resilient finger has a portion with an outer surface slanting distally radially outwardly, the slide having an abutment surface positioned so that when the slide is moved distally with respect to the radially resilient finger the abutment surface of the slide engages the slanted outer surface of the radially resilient finger to move the finger radially inwardly, thereby disengaging the finger from the complementary structure of the handle housing and permitting the cartridge housing to be removed from the handle housing.

62. The rotational atherectomy device of claim 61 wherein the cartridge latch includes two or more radially resilient fingers carried by the cartridge housing.

63. The rotational atherectomy device of claim 59 further comprising a catch positioned to engage a catch-engaging element of the slide, the catch restricting free movement of the slide between the neutral position and the working position.

64. The rotational atherectomy device of claim 63 wherein the cartridge latch comprises at least one radially resilient finger which is carried by the cartridge housing and which is removably engageable with a complementary structure carried by the handle housing.

65. The rotational atherectomy device of claim 64 wherein the catch comprises a radially outwardly extending shoulder carried by the resilient finger.

66. The rotational atherectomy device of claim 65 wherein the radially outwardly extending shoulder of the finger and the catch engaging element of the slide are sized and positioned so that the slide may be moved between its neutral and working positions without unlocking the cartridge latch.

67. The rotational atherectomy device of claim 65 wherein the catch includes proximal and distal engagement surfaces, the distal engagement surface being slanted proximally radially outwardly so that movement of the slide proximally from its neutral position causes the catch-engaging element to engage the distal engagement surface of the catch to move the catch, together with the radially resilient finger, radially inwardly a distance sufficient to release the catch-engaging element of the slide from the catch, thereby permitting the slide to be manually moved from its neutral position to its working position.

68. The rotational atherectomy device of claim 65 wherein the catch includes proximal and distal engagement surfaces, the proximal engagement surface being slanted distally radially outwardly so that movement of the slide distally from its working position causes the catch-engaging element to engage the proximal engagement surface of the catch to move the catch, together with the radially resilient finger, radially inwardly a distance sufficient to release the catch-engaging element of the slide from the catch, thereby permitting the slide to be manually moved distally out of its working position to and beyond its neutral position.

69. The rotational atherectomy device of claim 65 wherein at least one of the catch and the catch-engaging element has an engagement surface which is slanted proximally radially outwardly so that movement of the slide proximally from its neutral position forces the catch, together with the radially resilient finger, to move radially inwardly a distance sufficient to release the catch-engaging element of the slide from the catch, thereby permitting the slide to be manually moved from its neutral position to its working position.

70. The rotational atherectomy device of claim 65 wherein at least one of the catch and the catch-engaging element has an engagement surface which is slanteddistally radially outwardly so that movement of the slide distally from its working position forces the catch, together with the radially resilient finger, to move radially inwardly a distance sufficient to release the catch-engaging element of the slide from the catch, thereby permitting the slide to be manually moved distally out of its working position to and beyond its neutral position.

71. The rotational atherectomy device of claim 65 further comprising a spring biasing the slide toward its working position, the catch and the catch-engaging element having complementary engagement surfaces which are generally perpendicular to a longitudinal axis of the cartridge housing and which restrict proximal movement of the slide from its neutral position to its working position.

72. The rotational atherectomy device of claim 71 wherein the complementary engagement surfaces are sized and positioned so that they become disengaged when the radially resilient finger is deflected radially inwardly, thereby allowing the spring to move the slide from its neutral position to its working position.

73. The rotational atherectomy device of claim 65 further comprising a spring biasing the slide toward its working position, the catch and the catch-engaging element being sized and positioned so that insertion of the cartridge housing into the handle housing causes the radially resilient finger, together with the catch, to move radially inwardly a distance sufficient to release the catch-engaging element of the slide from the catch, thereby allowing the spring to move the slide from its neutral position to its working position.

74. The rotational atherectomy device of claim 73 wherein the slide biasing spring comprises a coil spring disposed about the cartridge housing.

75. The rotational atherectomy device of claim 73 wherein the slide biasing spring is compressed between opposing spring abutting surfaces of the slide and the cartridge housing.

76. The rotational atherectomy device of claim 59 wherein the handle housing includes a pair of openings sized and positioned so that the slide may be grasped through the openings by a user when the cartridge housing is attached to the handle housing.

77. The rotational atherectomy device of claim 76 wherein the openings are sufficiently long to permit manual movement of the slide between the neutral and working positions when the cartridge housing is attached to the handle housing.

78. The rotational atherectomy device of claim 76 wherein the openings are sufficiently long that a user, by a single movement, may move the slide from the slide's working position to a position where the cartridge housing is at least partially moved out of the handle housing, the single movement including a first phase, where the slide is moved from its working position to its cartridge unlocked position, and a second phase where the slide, together with the cartridge housing, is moved distally with respect to the handle housing.

79. The rotational atherectomy device of claim 76 wherein the openings have a longitudinal length of at least about one inch.

80. A rotational atherectomy device comprising:
    a handle housing;
    a rotatable prime mover carried by a prime mover carriage which is disposed within the handle housing, the prime mover carriage being longitudinally movable with respect to the handle housing;
    an exchangeable drive shaft cartridge including:
        a cartridge housing which is removably attachable to the handle housing;
        a longitudinally movable tube disposed within the cartridge housing and having a proximal end portion which is removably attachable to the prime mover carriage for longitudinal movement therewith;
        a tube latch which selectively locks the longitudinally movable tube against longitudinal movement with respect to the cartridge housing; and
        a rotatable flexible drive shaft having a proximal portion which is disposed within the longitudinally movable tube and a distal portion which includes a tissue removal implement;
    a drive shaft attachment mechanism removably attaching the proximal portion of the drive shaft to the prime mover;
    a cartridge latch removably locking the cartridge housing to the handle housing; and
    a slide which is longitudinally movable with respect to the cartridge housing among at least three positions, a working position where the slide causes the tube latch to unlock the longitudinally movable tube, a neutral position where the slide causes the tube latch to lock the tube against longitudinal movement with respect to the cartridge housing, and a cartridge unlocked position where the slide causes the tube latch to maintain the longitudinally movable tube in its locked position and unlocks the cartridge latch, thereby permitting the cartridge housing to be removed from the handle housing.

81. The rotational atherectomy device of claim 80 wherein the cartridge latch comprises at least one radially resilient finger which is carried by the cartridge housing and which is removably engageable with a complementary structure carried by the handle housing.

82. The rotational atherectomy device of claim 81 wherein the radially resilient finger has a portion with an outer surface slanting distally radially outwardly, the slide having an abutment surface positioned so that when the slide is moved distally with respect to the radially resilient finger the abutment surface of the slide engages the slanted outer surface of the radially resilient finger to move the finger radially inwardly, thereby disengaging the finger from the complementary structure of the handle housing and permitting the cartridge housing to be removed from the handle housing.

83. The rotational atherectomy device of claim 82 wherein the cartridge latch includes two or more radially resilient fingers carried by the cartridge housing.

84. The rotational atherectomy device of claim 81 wherein the radially resilient finger carries a catch positioned to engage a catch-engaging element of the slide, the catch restricting free movement of the slide between the neutral position and the working position.

85. The rotational atherectomy device of claim 84 wherein the catch includes proximal and distal engagement surfaces, the distal engagement surface being slanted proximally radially outwardly so that movement of the slide proximally from its neutral position causes the catch-engaging element to engage the distal engagement surface of the catch to move the catch, together with the radially resilient finger, radially inwardly a distance sufficient to release the catch-engaging element of the slide from the catch, thereby permitting the slide to be manually moved from its neutral position to its working position.

86. The rotational atherectomy device of claim 84 wherein the catch includes proximal and distal engagement surfaces, the proximal engagement surface being slanted distally radially outwardly so that movement of the slide distally from its working position causes the catch-engaging element to engage the proximal engagement surface of the catch to move the catch, together with the radially resilient finger, radially inwardly a distance sufficient to release the catch-engaging element of the slide from the catch, thereby permitting the slide to be manually moved distally out of its working position to and beyond its neutral position.

87. The rotational atherectomy device of claim 84, 85, or 86 wherein the catch of the finger and the catch engaging element of the slide are sized and positioned so that the slide may be moved between its neutral and working positions without unlocking the cartridge latch.

88. The rotational atherectomy device of claim 84 wherein at least one of the catch and the catch-engaging element has an engagement surface which is slanted proximally radially outwardly so that movement of the slide proximally from its neutral position forces the catch, together with the radially resilient finger, to move radially inwardly a distance sufficient to release the catch-engaging element of the slide from the catch, thereby permitting the slide to be manually moved from its neutral position to its working position.

89. The rotational atherectomy device of claim 84 wherein at least one of the catch and the catch-engaging element has an engagement surface which is slanted distally radially outwardly so that movement of the slide distally from its working position forces the catch, together with the radially resilient finger, to move radially inwardly a distance sufficient to release the catch-engaging element of the slide from the catch, thereby permitting the slide to be manually moved distally out of its working position to and beyond its neutral position.

90. The rotational atherectomy device of claim 84 further comprising a spring biasing the slide toward its working position, the catch and the catch-engaging element having complementary engagement surfaces which are generally perpendicular to a longitudinal axis of the cartridge housing and which restrict proximal movement of the slide from its neutral position to its working position.

91. The rotational atherectomy device of claim 90 wherein the complementary engagement surfaces are sized and positioned so that they become disengaged when the radially resilient finger is deflected radially inwardly, thereby allowing the spring to move the slide from its neutral position to its working position.

92. The rotational atherectomy device of claim 84 further comprising a spring biasing the slide toward its working position, the catch and the catch-engaging element being sized and positioned so that insertion of the cartridge housing into the handle housing causes the radially resilient finger, together with the catch, to move radially inwardly a distance sufficient to release the catch-engaging element of the slide from the catch, thereby allowing the spring to move the slide from its neutral position to its working position.

93. The rotational atherectomy device of claim 92 wherein the slide biasing spring comprises a coil spring disposed about the cartridge housing.

94. The rotational atherectomy device of claim 92 wherein the slide biasing spring is compressed between opposing spring abutting surfaces of the slide and the cartridge housing.

95. The rotational atherectomy device of claim 80 wherein the handle housing includes a pair of openings sized and positioned so that the slide may be grasped through the openings by a user when the cartridge housing is attached to the handle housing.

96. The rotational atherectomy device of claim 95 wherein the openings are sufficiently long to permit manual movement of the slide between the neutral and working positions when the cartridge housing is attached to the handle housing.

97. The rotational atherectomy device of claim 95 wherein the openings are sufficiently long that a user, by a single movement, may move the slide from the slide's working position to a position where the cartridge housing is at least partially moved out of the handle housing, the single movement including a first phase, where the slide is moved from its working position to its cartridge unlocked position, and a second phase where the slide, together with the cartridge housing, is moved distally with respect to the handle housing.

98. The rotational atherectomy device of claim 95 wherein the openings have a longitudinal length of at least about one inch.

99. A device comprising:
   a handle housing;
   a carriage which is disposed within the handle housing, the carriage being longitudinally movable with respect to the handle housing;
   an exchangeable cartridge including:
      a cartridge housing which is removably attachable to the handle housing;
      a longitudinally movable tube disposed within the cartridge housing and having a proximal end portion which is removably attachable to the carriage for longitudinal movement therewith;
      a tube latch which selectively locks the longitudinally movable tube against longitudinal movement with respect to the cartridge housing; and
   a cartridge latch removably locking the cartridge housing to the handle housing; and
   a slide which is longitudinally movable with respect to the cartridge housing among at least three positions, a working position where the slide causes the tube latch to unlock the longitudinally movable tube, a neutral position where the slide causes the tube latch to lock the tube against longitudinal movement with respect to the cartridge housing, and a cartridge unlocked position where the slide causes the tube latch to maintain the longitudinally movable tube in its locked position and unlocks the cartridge latch, thereby permitting the cartridge housing to be removed from the handle housing.

100. The device of claim 99 wherein the cartridge latch comprises at least one radially resilient finger which is carried by the cartridge housing and which is removably engageable with a complementary structure carried by the handle housing.

101. The device of claim 100 wherein the radially resilient finger has a portion with an outer surface slanting distally radially outwardly, the slide having an abutment surface positioned so that when the slide is moved distally with respect to the radially resilient finger the abutment surface of the slide engages the slanted outer surface of the radially resilient finger to move the finger radially inwardly, thereby disengaging the finger from the complementary structure of the handle housing and permitting the cartridge housing to be removed from the handle housing.

102. The device of claim 101 wherein the cartridge latch includes two or more radially resilient fingers carried by the cartridge housing.

103. The device of claim 100 wherein the radially resilient finger carries a catch positioned to engage a catch-engaging element of the slide, the catch restricting free movement of the slide between the neutral position and the working position.

104. The device of claim 103 wherein the catch includes proximal and distal engagement surfaces, the distal engagement surface being slanted proximally radially outwardly so that movement of the slide proximally from its neutral position causes the catch-engaging element to engage the distal engagement surface of the catch to move the catch, together with the radially resilient finger, radially inwardly a distance sufficient to release the catch-engaging element of the slide from the catch, thereby permitting the slide to be manually moved from its neutral position to its working position.

105. The device of claim 103 wherein the catch includes proximal and distal engagement surfaces, the proximal engagement surface being slanted distally radially outwardly so that movement of the slide distally from its working position causes the catch-engaging element to engage the proximal engagement surface of the catch to move the catch, together with the radially resilient finger, radially inwardly a distance sufficient to release the catch-engaging element of the slide from the catch, thereby permitting the slide to be manually moved distally out of its working position to and beyond its neutral position.

106. The device of claim 103, 104, or 105 wherein the catch of the finger and the catch engaging element of the slide are sized and positioned so that the slide may be moved between its neutral and working positions without unlocking the cartridge latch.

107. The device of claim 103 wherein at least one of the catch and the catch-engaging element has an engagement surface which is slanted proximally radially outwardly so that movement of the slide proximally from its neutral position forces the catch, together with the radially resilient finger, to move radially inwardly a distance sufficient to release the catch-engaging element of the slide from the catch, thereby permitting the slide to be manually moved from its neutral position to its working position.

108. The device of claim 103 wherein at least one of the catch and the catch-engaging element has an engagement surface which is slanted distally radially outwardly so that movement of the slide distally from its working position forces the catch, together with the radially resilient finger, to move radially inwardly a distance sufficient to release the catch-engaging element of the slide from the catch, thereby permitting the slide to be manually moved distally out of its working position to and beyond its neutral position.

109. The device of claim 103 further comprising a spring biasing the slide toward its working position, the catch and the catch-engaging element having complementary engagement surfaces which are generally perpendicular to a longitudinal axis of the cartridge housing and which restrict proximal movement of the slide from its neutral position to its working position.

110. The device of claim 109 wherein the complementary engagement surfaces are sized and positioned so that they become disengaged when the radially resilient finger is deflected radially inwardly, thereby allowing the spring to move the slide from its neutral position to its working position.

111. The device of claim 103 further comprising a spring biasing the slide toward its working position, the catch and the catch-engaging element being sized and positioned so that insertion of the cartridge housing into the handle housing causes the radially resilient finger, together with the catch, to move radially inwardly a distance sufficient to release the catch-engaging element of the slide from the catch, thereby allowing the spring to move the slide from its neutral position to its working position.

112. The device of claim 111 wherein the slide biasing spring comprises a coil spring disposed about the cartridge housing.

113. The device of claim 111 wherein the slide biasing spring is compressed between opposing spring abutting surfaces of the slide and the cartridge housing.

114. The device of claim 99 wherein the slide is generally tubular in shape.

115. The device of claim 114 wherein the slide is disposed about the cartridge housing.

116. The device of claim 99 wherein the handle housing includes a pair of openings sized and positioned so that the slide may be grasped through the openings by a user when the cartridge housing is attached to the handle housing.

117. The device of claim 116 wherein the openings are sufficiently long to permit manual movement of the slide between the neutral and working positions when the cartridge housing is attached to the handle housing.

118. The device of claim 116 wherein the openings are sufficiently long that a user, by a single movement, may move the slide from the slide's working position to a position where the cartridge housing is at least partially moved out of the handle housing, the single movement including a first phase, where the slide is moved from its working position to its cartridge unlocked position, and a second phase where the slide, together with the cartridge housing, is moved distally with respect to the handle housing.

119. The device of claim 116 wherein the openings have a longitudinal length of at least about one inch.

120. The device of claim 99 wherein the tube latch is capable of selectively locking the slide against longitudinal movement with respect to the cartridge housing.

121. The claim 120 wherein the tube latch is configured and arranged so that whenever the tube is locked against longitudinal movement then the slide is longitudinally movable, and whenever the slide is locked against longitudinal movement then the tube is longitudinally movable.

122. The device of claim 121 wherein the tube latch includes a tube locking element which is radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

123. The device of claim 122 wherein the tube latch includes three or more tube locking elements circumferentially spaced away from each other.

124. The device of claim 122 wherein the tube locking element is disposed within a radial bore in a wall of the cartridge housing.

125. The device of claim 122 wherein the tube locking element comprises a radially movable locking pin.

126. The device of claim 122 wherein the tube locking element comprises a radially movable locking ball.

127. The device of claim 122 wherein the tube latch includes a generally annular recess formed in an outer surface of the longitudinally movable tube, the recess receiving an inner portion of the tube locking element when the tube locking element is moved radially inwardly to its tube locked position.

128. The device of claim 127 wherein the tube latch includes a generally annular recess formed in an inner surface of the slide, the annular recess receiving an outer portion of the tube locking element when the tube locking element is moved radially outwardly to its tube unlocked position.

129. An exchangeable cartridge attachable to a handle housing comprising:

a cartridge housing which is removably attachable to the handle housing;

a longitudinally movable tube disposed within the cartridge housing;

a rotatable drive shaft having a proximal portion which is disposed within the longitudinally movable tube and a distal portion which includes a material removal implement;

a cartridge latch; and a slide which is longitudinally movable with respect to the cartridge housing from a neutral position, where the cartridge latch is locked, to a cartridge unlocked position where the slide unlocks the cartridge latch, thereby permitting the cartridge housing to be removed from the handle housing.

130. The exchangeable cartridge of claim 129 wherein the slide is generally tubular in shape.

131. The exchangeable cartridge of claim 129 wherein the cartridge latch comprises at least one radially resilient finger which is carried by the cartridge housing and which is removably engageable with a complementary structure carried by the handle housing.

132. The exchangeable cartridge of claim 131 wherein the cartridge latch includes two or more radially resilient fingers carried by the cartridge housing.

133. The exchangeable cartridge of claim 131 wherein the radially resilient finger has a portion with an outer surface slanting distally radially outwardly, the slide having an abutment surface positioned so that when the slide is moved distally with respect to the radially resilient finger the abutment surface of the slide engages the slanted outer surface of the radially resilient finger to move the finger radially inwardly, thereby disengaging the finger from the complementary structure of the handle housing and permitting the cartridge housing to be removed from the handle housing.

134. The exchangeable cartridge of claim 133 wherein the abutment surface comprises a distal end of the slide.

135. The exchangeable cartridge of claim 129 further comprising a tube latch for selectively locking the longitudinally movable tube against longitudinal movement with respect to the cartridge housing.

136. The exchangeable cartridge of claim 135 wherein the tube latch is capable of selectively locking the slide against longitudinal movement with respect to the cartridge housing.

137. The exchangeable cartridge of claim 136 wherein the tube latch is configured and arranged so that whenever the tube is locked against longitudinal movement then the slide is longitudinally movable, and whenever the slide is locked against longitudinal movement then the tube is longitudinally movable.

138. The exchangeable cartridge of claim 129 further comprising a tube latch positioned to selectively lock the longitudinally movable tube and the slide against longitudinal movement with respect to the cartridge housing.

139. The exchangeable cartridge of claim 138 wherein the tube latch is configured and arranged so that whenever the tube is locked against longitudinal movement then the slide is longitudinally movable, and whenever the slide is locked against longitudinal movement then the tube is longitudinally movable.

140. The exchangeable cartridge of claim 139 wherein the tube latch includes a tube locking element carried by the cartridge housing, the tube locking element being radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

141. The exchangeable cartridge of claim 140 wherein the tube latch includes three or more tube locking elements circumferentially spaced away from each other.

142. The exchangeable cartridge of claim 140 wherein the tube locking element is disposed within a radial bore in a wall of the cartridge housing.

143. The exchangeable cartridge of claim 140 wherein the tube locking element comprises a radially movable locking pin.

144. The exchangeable cartridge of claim 140 wherein the tube locking element comprises a radially movable locking ball.

145. The exchangeable cartridge of claim 140 wherein the tube latch includes a generally annular recess formed in an outer surface of the longitudinally movable tube, the recess receiving an inner portion of the tube locking element when the tube locking element is moved radially inwardly to its tube locked position.

146. The exchangeable cartridge of claim 145 wherein the tube latch includes a generally annular recess formed in an inner surface of the slide, the annular recess receiving an outer portion of the tube locking element when the tube locking element is moved radially outwardly to its tube unlocked position.

147. The exchangeable cartridge of claim 146 wherein the tube latch permits longitudinal movement of the slide when the annular recess of the longitudinally moveable tube is longitudinally aligned with the tube locking element carried by the cartridge housing.

148. The exchangeable cartridge of claim 129 further comprising at least one tube locking element carried by the cartridge housing and radially movable between at least two positions, a tube locked position, where the tube locking element is moved radially inwardly, thereby restricting longitudinal movement of the tube with respect to the cartridge housing, and a tube unlocked position, where the tube locking element is moved radially outwardly, thereby permitting longitudinal movement of the tube with respect to the cartridge housing.

149. The exchangeable cartridge of claim 148 wherein the tube locking element is disposed within a radial bore in a wall of the cartridge housing.

150. The exchangeable cartridge of claim 148 wherein the slide is generally tubular and includes an inner surface having a generally annular recess which receives an outer portion of the tube locking element when the tube locking element is moved radially outwardly to its tube unlocked position.

151. The exchangeable cartridge of claim 148 wherein an outer surface of the longitudinally movable tube has a generally annular recess which receives an inner portion of the tube locking element when the tube locking element is moved radially inwardly to its tube locked position.

152. The exchangeable cartridge of claim 148 wherein the slide is movable proximally from its neutral position, where the cartridge latch is locked and the tube locking element is in its tube locked position, to a working position where the cartridge latch remains locked while the tube locking element is movable to its tube unlocked position, thereby permitting the longitudinally moveable tube to be moved proximally out of its tube lockable position.

153. The exchangeable cartridge of claim 152 wherein the slide is generally tubular and includes a generally annular recess in its inner surface, the annular recess in the slide being positioned so that movement of the slide to its working position longitudinally aligns the annular recess of the slide with the tube locking element, permitting the tube locking element to move radially outwardly to unlock the longitudinally movable tube.

154. The exchangeable cartridge of claim 153 wherein an annular recess in the outer surface of the longitudinally movable tube is positioned so that whenever the tube is moved proximally out of its tube lockable position the tube locking element is moved radially outwardly so that an outer portion of the tube locking element is moved into the annular recess of the slide, the tube locking element being retained in such position by an outer surface of the longitudinally movable tube, thereby locking the slide in its working position.

155. The exchangeable cartridge of claim 153 wherein the annular recess in the tubular slide is positioned so that whenever the slide is moved distally out of its working position the tube locking element is moved radially inwardly so that an inner portion of the tube locking element is moved into an annular recess in an outer surface of the longitudinally movable tube, the tube locking element being retained in such position by the inner surface of the slide, thereby locking the longitudinally movable tube against longitudinal movement with respect to the cartridge housing.

156. The exchangeable cartridge of claim 152 wherein the cartridge latch comprises at least one radially resilient finger which is carried by the cartridge housing and which is removably engageable with a complementary structure carried by the handle housing.

157. The exchangeable cartridge of claim 156 wherein the radially resilient finger carries a catch positioned to engage a catch-engaging element of the slide, the catch restricting free movement of the slide between the neutral position and the working position.

158. The exchangeable cartridge of claim 157 wherein the catch includes proximal and distal engagement surfaces, the distal engagement surface being slanted proximally radially outwardly so that movement of the slide proximally from its neutral position causes the catch-engaging element to engage the distal engagement surface of the catch to move the catch, together with the radially resilient finger, radially inwardly a distance sufficient to release the catch-engaging element of the slide from the catch, thereby permitting the slide to be manually moved from its neutral position to its working position.

159. The exchangeable cartridge of claim 157 wherein the catch includes proximal and distal engagement surfaces, the proximal engagement surface being slanted distally radially outwardly so that movement of the slide distally from its working position causes the catch-engaging element to engage the proximal engagement surface of the catch to move the catch, together with the radially resilient finger, radially inwardly a distance sufficient to release the catch-engaging element of the slide from the catch, thereby permitting the slide to be manually moved distally out of its working position to and beyond its neutral position.

160. The exchangeable cartridge of claim 157, 158 or 159 wherein the catch of the finger and the catch engaging element of the slide are sized and positioned so that the slide may be moved between its neutral and working positions without unlocking the cartridge latch.

161. The exchangeable cartridge of claim 157 wherein at least one of the catch and the catch-engaging element has an engagement surface which is slanted proximally radially outwardly so that movement of the slide proximally from its neutral position forces the catch, together with the radially resilient finger, to move radially inwardly a distance sufficient to release the catch-engaging element of the slide from the catch, thereby permitting the slide to be manually moved from its neutral position to its working position.

162. The exchangeable cartridge of claim 157 wherein at least one of the catch and the catch-engaging element has an engagement surface which is slanted distally radially outwardly so that movement of the slide distally from its working position forces the catch, together with the radially resilient finger, to move radially inwardly a distance sufficient to release the catch-engaging element of the slide from the catch, thereby permitting the slide to be manually moved distally out of its working position to and beyond its neutral position.

163. The exchangeable cartridge of claim 157 further comprising a spring biasing the slide toward its working position, the catch and the catch-engaging element having complementary engagement surfaces which are generally perpendicular to a longitudinal axis of the cartridge housing and which restrict proximal movement of the slide from its neutral position to its working position.

164. The exchangeable cartridge of claim 163 wherein the complementary engagement surfaces are sized and positioned so that they become disengaged when the radially resilient finger is deflected radially inwardly, thereby allowing the spring to move the slide from its neutral position to its working position.

165. The exchangeable cartridge of claim 157 further comprising a spring biasing the slide toward its working position, the catch and the catch-engaging element being sized and positioned so that insertion of the cartridge housing into the handle housing causes the radially resilient finger, together with the catch, to move radially inwardly a distance sufficient to release the catch-engaging element of the slide from the catch, thereby allowing the spring to move the slide from its neutral position to its working position.

166. The exchangeable cartridge of claim 165 wherein the slide biasing spring comprises a coil spring disposed about the cartridge housing.

167. The exchangeable cartridge of claim 165 wherein the slide biasing spring is compressed between opposing spring abutting surfaces of the slide and the cartridge housing.

* * * * *